US009097707B2

(12) United States Patent
Isacoff et al.

(10) Patent No.: US 9,097,707 B2
(45) Date of Patent: Aug. 4, 2015

(54) PHOTOREACTIVE REGULATOR OF PROTEIN FUNCTION AND METHODS OF USE THEREOF

(71) Applicant: The Regents of the University of California, Oakland, CA (US)

(72) Inventors: Ehud Y. Isacoff, Berkeley, CA (US); Richard H. Kramer, Oakland, CA (US); Dirk Trauner, Munich (DE); Matthew R. Banghart, Oakland, CA (US); Matthew Volgraf, Oakland, CA (US); Pablo Ignacio Gorostiza Langa, Barcelona (ES); Katharine Borges, Centerport, NY (US)

(73) Assignee: The Regents of the University of California, Oakland, CA (US)

( * ) Notice: Subject to any disclaimer, the term of this patent is extended or adjusted under 35 U.S.C. 154(b) by 118 days.

(21) Appl. No.: 13/671,908

(22) Filed: Nov. 8, 2012

(65) Prior Publication Data
US 2013/0137113 A1    May 30, 2013

Related U.S. Application Data

(60) Continuation of application No. 13/364,105, filed on Feb. 1, 2012, now Pat. No. 8,309,350, which is a division of application No. 11/601,591, filed on Nov. 17, 2006, now Pat. No. 8,114,843.

(60) Provisional application No. 60/737,935, filed on Nov. 18, 2005.

(51) Int. Cl.
| C07C 29/56 | (2006.01) |
| G01N 33/53 | (2006.01) |
| C07K 14/705 | (2006.01) |
| A61K 38/00 | (2006.01) |

(52) U.S. Cl.
CPC .......... *G01N 33/53* (2013.01); *C07K 14/70571* (2013.01); *A61K 38/00* (2013.01); *G01N 2500/10* (2013.01)

(58) Field of Classification Search
CPC .................................................. G01N 24/088
See application file for complete search history.

(56) References Cited

U.S. PATENT DOCUMENTS

| 4,589,882 | A | 5/1986 | Urry |
| 5,437,982 | A | 8/1995 | Catterall |
| 5,998,588 | A | 12/1999 | Hoffman et al. |
| 6,376,655 | B1 | 4/2002 | Berg et al. |
| 7,034,014 | B2 | 4/2006 | Hostetler et al. |
| 7,420,044 | B1 | 9/2008 | Harrington et al. |
| 2001/0053849 | A1 | 12/2001 | Kreek et al. |
| 2002/0001842 | A1 | 1/2002 | Chapman |
| 2003/0166840 | A1 | 9/2003 | Urry et al. |
| 2003/0181531 | A1 | 9/2003 | Sherris et al. |
| 2005/0272677 | A1 | 12/2005 | Friesen et al. |
| 2006/0252677 | A1* | 11/2006 | Ohara et al. ............... 514/12 |
| 2007/0191411 | A1 | 8/2007 | Smith |
| 2009/0170901 | A1* | 7/2009 | Borza et al. .............. 514/330 |

FOREIGN PATENT DOCUMENTS

| WO | WO 02/061415 | 8/2002 |
| WO | WO 2007/024290 | 3/2007 |

OTHER PUBLICATIONS

Ichinose et al. (2003) Ca2+-independent, but voltage- and activity-dependent regulation of the NMDA receptor outward K+ current in mouse cortical neurons, vol. 551, pp. 403-417.*
Colledge et al. (2003) Ubiquitination Regulates PSD-95 Degradation and AMPA Receptor Surface Expression, Neuron, vol. 40, No. 3, pp. 595-607.*
Allen, C. "A Molecular Light Switch Turns Off Neural Activity", 2004, Nat. Neurosci., 2004, vol. 7, No. 12, p. 1291.
Banghart et al., "Light Activated Ion Channels for Remote Control of Neuronal Firing", 2004, Nature Neuroscience, vol. 7, No. 12, pp. 1381-1386.
Behrendt, et al., "Photomodulation of Conformational State. Synthesis of Cyclic Peptides with Backbone-Azobenzene Moieties", 1999, J. Pept. Sci., vol. 5, No. 11, pp. 519-529.
Buster et al., "Na-Nuclear Megnetic Resonance Investigation of Gramicidin-Induced Ion Transport Through Membranes Under Equilibrium Conditions", 1988, Biophys. J., vol. 53, No. 2, pp. 145-152.
Chambers et al.. "Light-induced Depolarization of Neurons Using a Modified Shaker (K+) Channel and a Molecular Photoswitch", 2006, J. Neurophysiol. vol. 96, No. 5, pp. 2792-2796.
Essen., et al.. "Ino-Channel Engineering". 2008, Annual Reports Section C, vol. 104, pp. 165-168.
Evans, et al., "Acetylcholine-Activated Single Channel Currents in Cultured/Aplysia Neurons", 1989, Biophy. J., vol. 55, pp. 553a, abstract No. W-Pos257.
Fortin, et al., "Photochemical Control of Endogenous Ion Channels and Cellular Excitability", 2008, Nat. Methods, vol. 5, No. 4, pp. 331-338.
Grigoriev, et al., "Differences in Ion Permeability of an Artificial Bilayer Membrane Caused by Ampullosporin and Bergofungin, New 15-Membered Peptaibol-Type Antibiotics", 1997, Bioelectrochem. Bioeng., vol. 44, pp. 155-158.

(Continued)

*Primary Examiner* — Manjunath Rao
*Assistant Examiner* — Samuel Liu
(74) *Attorney, Agent, or Firm* — Bozicevic, Field & Francis LLP; Paula A. Borden

(57) ABSTRACT

The present invention provides a synthetic regulator of protein function, which regulator is a light-sensitive regulator. The present invention further provides a light-regulated polypeptide that includes a subject synthetic regulator. Also provided are cells and membranes comprising a subject light-regulated polypeptide. The present invention further provides methods of modulating protein function, involving use of light. The present invention further provides methods of identifying agents that modulate protein function.

10 Claims, 34 Drawing Sheets

(56) References Cited

OTHER PUBLICATIONS

Heidmann et al., "Fast Kinetic Studies on the Allosteric Interactions Between Acetylcholine Receptor and Local Anesthetic Binding Sites", 1979, Eur. J. Biochem., vol. 94, pp. 281-206.

Kramer, et al. "Photochemical Tools for Remote Control of Ion Channels in Excitable Cells", 2005, Nat. Chem. Biol., vol. 1, No. 7. pp. 360-365.

Kim, et al., "Synthesis and Characterization of Photochromic Liquid Crystalline Polymer Beads", 2005, Mol. Cryst. Liq. Cryst., vol. 443, pp. 127-135.

Lester, et al., "A Covalently Bound Photisomerizable Agonist", 1980, J. Gen. Physiol., vol. 75, pp. 207-232.

Lien, et al., "Photomodulated Blocking of Gramicidin Ion Channels", 1996, J. Am. Chem. Soc., vol. 118, pp. 12222-12223.

O'Leary, et al., "Mutational Analysis of Ligand-Induced Activation of the Torpedo Acetylcholine Receptor", 1992, J. Biol. Chem., vol. 267, No. 12, pp. 8360-8365.

Powl, et al., "Lipid Interactions with Bacterial Channels: Fluorescence Studies", 2005, Biochem. Soc. Trans., vol. 33, part 5, pp. 905-909.

Sigma, BES Sodium Salt, 2009, www.sigmaaldrich.com/catalog/productdetail.do?N4=B2891%7CSIGMA%N5=SEARCH_CONCAT_PNO%7CBRAND_KEY%F=SPEC, p. 1.

Thompson, et al., "Flashy Science: Controlling Neural Function with Light", 2005, J. Neurosci., vol. 25, No. 45, pp. 10358-10365.

Urman, et al., "The Constrained Amino Acid Beta-ACC Confers Potency and Selectivity to Integrin Ligands", 2007, Agnew Chem Int. Ed. Engl., vol. 46, No. 1, pp. 3976-3978.

Wang, et al., "A Stable Mixed Disulfide Between Thioredoxin Reductase and its Substrate, Thioredoxin: Preparation and Characterization", 1996, Biochemistry, vol. 35, No. 15, pp. 4812-4819.

Wikipedia, "Opioid Receptor", 2010, en.wikipedia.org/wiki/opioid_Receptor, pp. 1-5.

Wikipedia, "Metabotropic Receptor", 2010, en.wikipedia.org/wiki/metabotropic_receptor, pp. 1-2.

Zhu, et al., "Analysis of the Roles of RGD-Binding Integrins, Alpha (4)/Alpha (9) Integrins, and CD9 in the Interaction of the Fertilin Beta (ADAM2) Disintegrin Domain with the Mouse Egg Membrane", 2002, Biol. Reprod., vol. 66, No. 4, pp. 1193-1202.

\* cited by examiner

1: (2S,4R)-4-methyl glutamate

2: (2S,4R)-4-allyl glutamate

3: Tether model

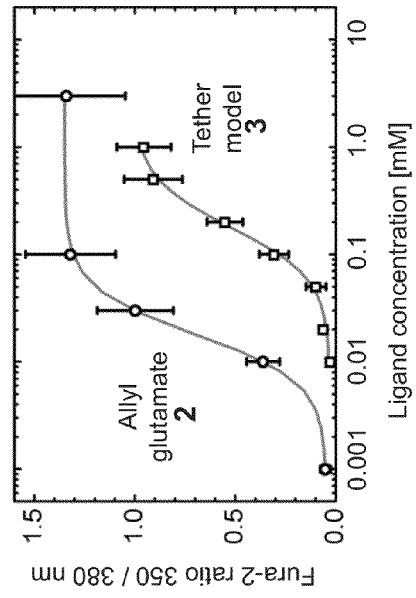
Fig. 7D
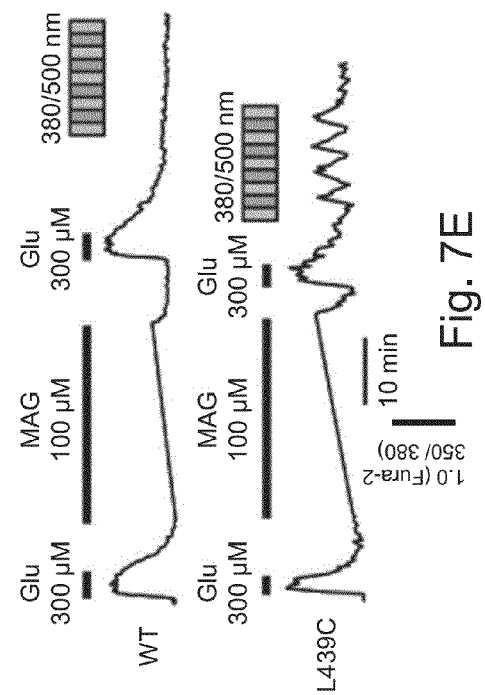
Fig. 7E
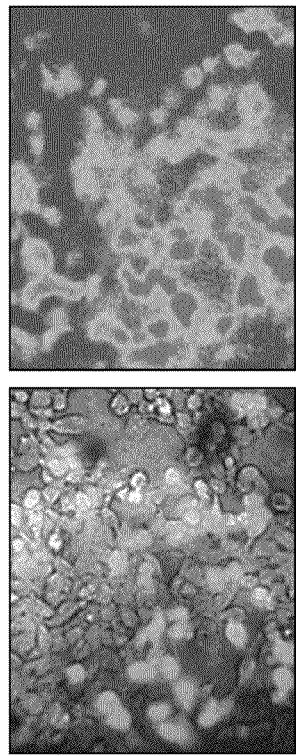
Fig. 7A
Fig. 7B
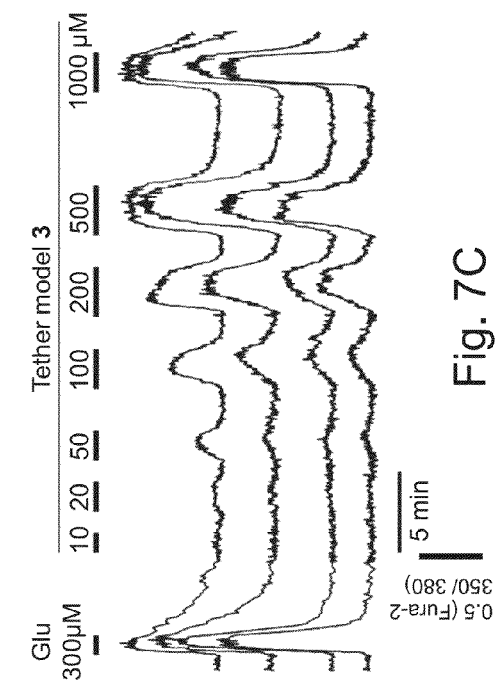
Fig. 7C

SEQUENCE LISTING

<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: synthetic primer

<400> SEQUENCE: 1
gattgttacc accatttgcg aagaaccgta tgttctg     37

<210> SEQ ID NO 2
<211> LENGTH: 38
<212> TYPE: DNA
<213> ORGANISM: Artificial Sequence
<220> FEATURE:
<223> OTHER INFORMATION: synthetic primer

<400> SEQUENCE: 2
cagaacatac ggttcttcgc aaaatggtgg taacaatc     38

US 9,097,707 B2

PHOTOREACTIVE REGULATOR OF PROTEIN FUNCTION AND METHODS OF USE THEREOF

CROSS-REFERENCE

This application claims the benefit of U.S. Provisional Patent Application No. 60/737,935, filed Nov. 18, 2005, which application is incorporated herein by reference in its entirety.

STATEMENT REGARDING FEDERALLY SPONSORED RESEARCH

This invention was made with Government support under contract MH60711 awarded by the National Institutes of Health. The Government has certain rights in this invention.

BACKGROUND OF THE INVENTION

The precise regulation of protein activity is fundamental to life. A mechanism of regulation, found across protein classes, from enzymes, to motors, to signaling proteins, is allosteric control of an active site by a remote regulatory binding site.

Many proteins function like molecular machines that undergo mechanical movements in response to input signals. These signals can consist of changes in voltage, membrane tension, temperature or, most commonly, ligand concentration. Ligands provide information about events in the external world, or about the energetic or biosynthetic state of the cell, and can be as small as a proton or as large as a whole protein. In allostery, ligand binding induces a structural change of a sensor domain, which propagates to a functional domain of the protein and alters its behavior. Such conformational control can operate over long distances, crossing a membrane or passing from one protein to another in a complex.

There is a need in the art for methods of regulating protein function. The present invention addresses this need.

LITERATURE

Lester et al. *J. Gen. Physiol.* 75, 207-232 (1980); Banghart et al. *Nature Neurosci.* 7, 1381-1386 (2004).

SUMMARY OF THE INVENTION

The present invention provides a synthetic regulator of protein function, which regulator is a light-sensitive (photoreactive) regulator. The present invention further provides a light-regulated polypeptide that includes a subject synthetic regulator. Also provided are cells and membranes comprising a subject light-regulated polypeptide. The present invention further provides methods of modulating protein function, involving use of light. The present invention further provides methods of identifying agents that modulate protein function.

BRIEF DESCRIPTION OF THE DRAWINGS

FIGS. 7A-E depict calcium imaging of iGluR6 activity.

DEFINITIONS

Figure 1:
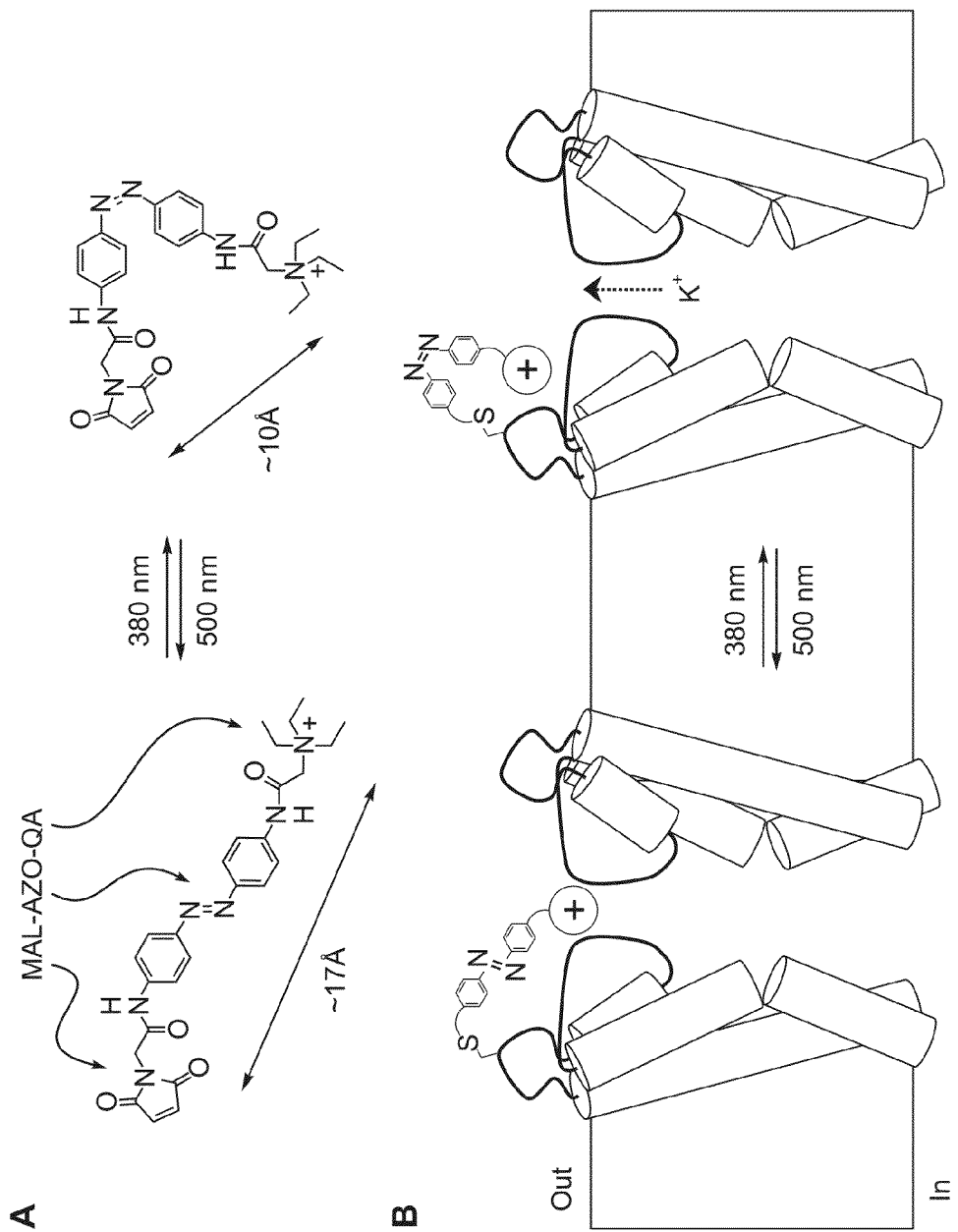
FIGS. 1A and 1B depict photoisomerization of MAL-AZO-QA gates ionic currents through modified Shaker channels.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes polypeptides comprising one or more of a fatty acid moiety, a lipid moiety, a sugar moiety, and a carbohydrate moiety. The term "polypeptides" includes post-translationally modified polypeptides.

The term "naturally-occurring" as used herein as applied to a polypeptide, a cell, or an organism, refers to a polypeptide, cell, or organism that is found in nature. For example, a polypeptide having an amino acid sequence that is present in an organism (including viruses) that can be isolated from a source in nature and which has not been intentionally modified by a human in the laboratory is naturally occurring.

The term "determining" includes any form of measurement, and includes determining if an effect is present or not. The terms "determining", "measuring", "evaluating", "assessing" and "assaying" are used interchangeably and include quantitative and qualitative determinations. Assessing may be relative or absolute. "Determining the effect of" includes determining the degree of an effect, and/or determining whether any effect has occurred. As used herein, the terms "determining," "measuring," and "assessing," and "assaying" are used interchangeably and include both quantitative and qualitative determinations.

A "host cell," or "a cell," as used herein, denotes an in vivo or in vitro prokaryotic cell, an in vivo or in vitro eukaryotic cell, or a cell from a multicellular organism (e.g., a cell line) cultured in vitro as a unicellular entity. A cell includes a cell that comprises a subject light-regulated polypeptide. A "host cell" includes cells that can be, or have been, used as recipients for a subject synthetic regulator. A "host cell" includes cells that can be, or have been, used as recipients for an exogenous nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, in some embodiments a subject host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, particularly humans. Non-human animal models, particularly mammals, e.g. non-human primates, murines, lagomorpha, etc. may be used for experimental investigations.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a synthetic regulator" includes a plurality of such regulators and reference to "the light-regulated polypeptide" includes reference to one or more light-regulated polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides a synthetic regulator of protein function, which regulator is a light-sensitive regulator. The present invention further provides a light-regulated polypeptide that includes a subject synthetic regulator. Also provided are cells and membranes comprising a subject light-regulated polypeptide. The present invention further provides methods of modulating protein function, involving use of light. The present invention further provides methods of identifying agents that modulate protein function.

Synthetic Regulator of Protein Function

The present invention provides a synthetic regulator of protein function, light-regulated polypeptides comprising the regulator, and devices comprising the polypeptides. A subject synthetic protein regulator comprises: a) a linker domain, comprising a moiety that provides for covalent linkage to an amino acid side chain; b) a photoisomerizable group; and c) a ligand that binds to a ligand binding site (e.g., an active site, an allosteric site, a pore of an ion channel, etc.) of a protein. A subject synthetic protein regulator (also referred to as a "synthetic regulator," or "a photoswitch") is suitable for attachment to a variety of polypeptides, including naturally-occurring (native, or endogenous) polypeptides, recombinant polypeptides, synthetic polypeptides, etc.

A subject synthetic regulator can be provided in any number of configurations, including linear and branched. In some embodiments, a subject synthetic regulator has the structure: $(A)_n$-$(B)_m$-$(C)_p$, where A is a linker domain, B is a photoisomerizable group, and C is a ligand, and where each of n, m, and p is independently 1 to 10, e.g., where each of n, m, and p is independently one, two, three, four, five, six, seven, eight, nine, or ten. In some embodiments, each of n, m, and p is 1, e.g., a subject synthetic regulator has the structure A-B-C. In other embodiments, a subject synthetic regulator comprises two or more different linker domains. In other embodiments, a subject synthetic regulator comprises two or more (e.g., 2 to 10, e.g., two, three, four, five, six, seven, eight, nine, or ten) photoisomerizable groups. In some embodiments, where the synthetic regulator comprises two or more photoisomerizable groups, the two or more photoisomerizable groups are arranged in tandem, either directly or separated by a spacer. In some embodiments, a subject synthetic regulator comprises a single linker domain, and two or more photoisomerizable groups, arranged in tandem, either directly or separated by a spacer. In other embodiments, a subject synthetic regulator comprises two or more different ligands.

In other embodiments, a subject synthetic regulator has the structure: C-$X_1$(A)-B-$X_2$(A)-C, where A is a linker domain, B is a photoisomerizable group, and C is a ligand, where $X_1$, when present, is a spacer, where $X_2$, when present, is a spacer, and where X(A) indicates that A branches off of X. Suitable spacers include peptide spacers (e.g., spacers of from about 1 to about 20 amino acids in length; non-peptide spacers, e.g., non-peptide polymers of various numbers of monomeric units, e.g., from one to about 20 units. In these embodiments, B can be present in multiple copies, either directly or in tandem.

Photoisomerizable Group

The photoisomerizable group is one that changes from a first isomeric form to a second isomeric form upon exposure to light of different wavelengths, or upon a change in exposure from dark to light, or from light to dark. For example, in some embodiments, the photoisomerizable group is in a first isomeric form when exposed to light of a first wavelength, and is in a second isomeric form when exposed to light of a second wavelength. Suitable photoisomerizable groups include stereoisomers and constitutional isomers.

The first wavelength and the second wavelength can differ from one another by from about 1 nm to about 2000 nm or more, e.g., from about 1 nm to about 10 nm, from about 10 nm to about 20 nm, from about 20 nm to about 50 nm, from about 50 nm to about 75 nm, from about 75 nm to about 100 nm, from about 100 nm to about 125 nm, from about 125 nm to about 150 nm, or from about 150 nm to about 200 nm, from about 200 nm to about 500 nm, from about 500 nm to about 800 nm, from about 800 nm to about 1000 nm, from about 1000 nm to about 1500 nm, from about 1500 nm to about 2000 nm, or more than 2000 nm.

In other embodiments, the photoisomerizable group is in a first isomeric form when exposed to light of a wavelength $\lambda_1$, and is in a second isomeric form in the absence of light (e.g., in the absence of light, the photoisomerizable group undergoes spontaneous relaxation into the second isomeric form). In these embodiments, the first isomeric form is induced by exposure to light of wavelength $\lambda_1$, and the second isomeric form is induced by not exposing the photoisomerizable group to light, e.g., keeping the photoisomerizable group in darkness. In other embodiments, the photoisomerizable group is in a first isomeric form in the absence of light, e.g., when the photoisomerizable group is in the dark; and the photoisomerizable group is in a second isomeric form when exposed to light of a wavelength $\lambda_1$. In other embodiments, the photoisomerizable group is in a first isomeric form when exposed to light of a first wavelength $\lambda_1$, and the photoisomerizable group is in a second isomeric form when exposed to light of second wavelength $\lambda_2$.

For example, in some embodiments, the photoisomerizable group is in a trans configuration in the absence of light, or when exposed to light of a first wavelength; and the photoisomerizable group is in a cis configuration when exposed to light, or when exposed to light of a second wavelength that is different from the first wavelength. As another example, in some embodiments, the photoisomerizable group is in a cis configuration in the absence of light, or when exposed to light of a first wavelength; and the photoisomerizable group is in a trans configuration when exposed to light, or when exposed to light of a second wavelength that is different from the first wavelength.

The wavelength of light that effects a change from a first isomeric form to a second isomeric form ranges from $10^{-8}$ m to about 1 m, e.g., from about $10^{-8}$ m to about $10^{-7}$ m, from about $10^{-7}$ m to about $10^{-6}$ m, from about $10^{-6}$ m to about $10^{-4}$ m, from about $10^{-4}$ m to about $10^{-2}$ m, or from about $10^{-2}$ m to about 1 m. "Light," as used herein, refers to electromagnetic radiation, including, but not limited to, ultraviolet light, visible light, infrared, and microwave.

The wavelength of light that effects a change from a first isomeric form to a second isomeric form ranges in some embodiments from about 200 nm to about 800 nm, e.g., from about 200 nm to about 250 nm, from about 250 nm to about 300 nm, from about 300 nm to about 350 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, or from about 750 nm to about 800 nm, or greater than 800 nm.

In other embodiments, the wavelength of light that effects a change from a first isomeric form to a second isomeric form ranges from about 800 nm to about 2500 nm, e.g., from about 800 nm to about 900 nm, from about 900 nm to about 1000 nm, from about 1000 nm to about 1200 nm, from about 1200 nm to about 1400 nm, from about 1400 nm to about 1600 nm, from about 1600 nm to about 1800 nm, from about 1800 nm to about 2000 nm, from about 2000 nm to about 2250 nm, or from about 2250 nm to about 2500 nm. In other embodiments, the wavelength of light that effects a change from a first isomeric form to a second isomeric form ranges from about 2 nm to about 200 nm, e.g., from about 2 nm to about 5 nm, from about 5 nm to about 10 nm, from about 10 nm to about 25 nm, from about 25 nm to about 50 nm, from about 50 nm to about 75 nm, from about 75 nm to about 100 nm, from about 100 nm to about 150 nm, or from about 150 nm to about 200 nm.

The difference between the first wavelength and the second wavelength can range from about 1 nm to about 2000 nm or more, as described above. Of course, where the synthetic light regulator is switched from darkness to light, the difference in wavelength is from essentially zero to a second wavelength.

The intensity of the light can vary from about 1 W/m$^2$ to about 50 W/m$^2$, e.g., from about 1 W/m$^2$ to about 5 W/m$^2$, from about 5 W/m$^2$ to about 10 W/m$^2$, from about 10 W/m$^2$, from about 10 W/m$^2$ to about 15 W/m$^2$, from about 15 W/m$^2$ to about 20 W/m$^2$, from about 20 W/m$^2$ to about 30 W/m$^2$, from about 30 W/m$^2$ to about 40 W/m$^2$, or from about 40 W/m$^2$ to about 50 W/m$^2$. The intensity of the light can vary from about 1 µW/cm$^2$ to about 100 µW/cm$^2$, e.g., from about 1 µW/cm$^2$ to about 5 µW/cm$^2$, from about 5 µW/cm$^2$ to about 10 µW/cm$^2$, from about 10 µW/cm$^2$ to about 20 µW/cm$^2$, from about 20 µW/cm$^2$ to about 25 µW/cm$^2$, from about 25 µW/cm$^2$ to about 50 µW/cm$^2$, from about 50 µW/cm$^2$ to about 75 µW/cm$^2$, or from about 75 µW/cm$^2$ to about 100 µW/cm$^2$. In some embodiments, the intensity of light varies from about 1 µW/mm$^2$ to about 1 W/mm$^2$, e.g., from about 1 µW/mm$^2$ to about 50 µW/mm$^2$, from about 50 µW/mm$^2$ to about 100 µW/mm$^2$, from about 100 µW/mm$^2$ to about 500 µW/mm$^2$, from about 500 µW/mm$^2$ to about 1 mW/mm$^2$, from about 1 mW/mm$^2$ to about 250 mW/mm$^2$, from about 250 mW/mm$^2$ to about 500 mW/mm$^2$, or from about 500 mW/mm$^2$ to about 1 W/mm$^2$.

In some embodiments, the change from a first isomeric form to a second isomeric form of the photoisomerizable group is effected using sound, instead of electromagnetic (EM) radiation (light). For example, in some embodiments, the change from a first isomeric form to a second isomeric form of the photoisomerizable group is effected using ultrasound.

Photoisomerizable groups are known in the art, and any known photoisomerizable group can be included in a subject synthetic regulator of protein function. Suitable photoisomerizable groups include, but are not limited to, azobenzene and derivatives thereof; spiropyran and derivatives thereof; triphenyl methane and derivatives thereof; 4,5-epoxy-2-cyclopentene and derivatives thereof; fulgide and derivatives thereof; thioindigo and derivatives thereof; diarylethene and derivatives thereof; diallylethene and derivatives thereof; overcrowded alkenes and derivatives thereof; and anthracene and derivatives thereof.

Suitable spiropyran derivatives include, but are not limited to, 1,3,3-trimethylindolinobenzopyrylospiran; 1,3,3-trimethylindolino-6'-nitrobenzopyrylospiran; 1,3,3-trimethylindolino-6'-bromobenzopyrylospiran; 1-n-decyl-3,3-dimethylindolino-6'-nitrobenzopyrylospiran; 1-n-octadecy-1-3,3-dimethylindolino-6'-nitrobenzopyrylospiran; 3',3'-dimethyl-6-nitro-1'-[2-(phenylcarbamoyl)ethyl]spiro; [2H-1-benzopyran-2,2'-indoline]; 1,3,3-trimethylindolino-8'-methoxybenzopyrylospiran; and 1,3,3-trimethylindolino-β-naphthopyrylospiran. Also suitable for use is a merocyanine form corresponding to spiropyran or a spiropyran derivative.

Suitable triphenylmethane derivatives include, but are not limited to, malachite green derivatives. specifically, there can be mentioned, for example, bis[dimethylamino)phenyl]phenylmethanol, bis[4-(diethylamino)phenyl]phenylmethanol, bis[4-(dibuthylamino)phenyl]phenylmethanol and bis[4-(diethylamino)phenyl]phenylmethane.

Suitable 4,5-epoxy-2-cyclopentene derivatives include, for example, 2,3-diphenyl-1-indenone oxide and 2',3'-dimethyl-2,3-diphenyl-1-indenone oxide.

Suitable azobenzene compounds include, e.g., compounds having azobenzene residues crosslinked to a side chain, e.g., compounds in which 4-carboxyazobenzene is ester bonded to the hydroxyl group of polyvinyl alcohol or 4-carboxyazobenzene is amide bonded to the amino group of polyallylamine. Also suitable are azobenzene compounds having azobenzene residues in the main chain, for example, those formed by ester bonding bis(4-hydroxyphenyl)dimethylmethane (also referred to as bisphenol A) and 4,4'-dicarboxyazobenzene or by ester bonding ethylene glycol and 4,4'-dicarboxyazobenzene.

Suitable fulgide derivatives include, but are not limited to, isopropylidene fulgide and adamantylidene fulgide.

Suitable diallylethene derivatives include, for example, 1,2-dicyano-1,2-bis(2,3,5-trimethyl-4-thienyl)ethane; 2,3-bis(2,3,5-trimethyl-4-thiethyl) maleic anhydride; 1,2-dicyano-1,2-bis(2,3,5-trimethyl-4-selenyl)ethane; 2,3-bis(2,3,5-trimethyl-4-selenyl) maleic anhydride; and 1,2-dicyano-1,2-bis(2-methyl-3-N-methylindole)ethane.

Suitable diarylethene derivatives include but are not limited to, substituted perfluorocylopentene-bis-3-thienyls and bis-3-thienylmaleimides.

Suitable overcrowded alkenes include, but are not limited to, cis-2-nitro-7-(dimethylamino)-9-(2',3'-dihydro-1'H-naphtho[2,1-b]thiopyran-1'-ylidene)-9H-thioxanthene and trans-dimethyl-[1-(2-nitro-thioxanthen-9-ylidene)-2,3-dihydro-1H-benzo[f]thiochromen-8-yl]amine. Overcrowded alkenes are described in the literature. See, e.g., terWiel et al. (2005) Org. Biomol. Chem. 3:28-30; and Geertsema et al. (1999) Agnew CHem. Int. Ed. Engl. 38:2738.

Other suitable photoisomerizable moieties include, e.g., reactive groups commonly used in affinity labeling, including diazoketones, aryl azides, diazerenes, and benzophenones.

Linker Domain

The linker domain is any of a variety of linkers that provide for stable association of the synthetic regulator with a polypeptide. The linker domain includes a binding moiety that provides for stable association with a polypeptide. In some embodiments, the linker domain provides for stable association with an amino acid side chain in a polypeptide. In other embodiments, the linker domain provides for stable association of the synthetic regulator with a sugar residue in the polypeptide. In other embodiments, the linker domain provides for stable association of the synthetic regulator with a moiety other than a sugar residue or an amino acid side chain. In some embodiments, the linked domain comprises a reactive electrophile that provides for stable association with an amino acid in the ligand-binding polypeptide. In some embodiments, the linked domain comprises a reactive electrophile that provides for stable association with an amino acid at or near a ligand-binding site in a ligand-binding protein.

Stable association of the synthetic regulator with a polypeptide includes covalent linkage; as well as non-covalent associations such as ionic interactions, and the like. In general, where the stable association is a non-covalent association, the stable association is a high-affinity association, e.g., the stable association between the synthetic regulator and the polypeptide has an affinity of from about $10^{-9}$ M to about $5 \times 10^{-9}$ M, from about $5 \times 10^{-9}$ M to about $10^{-10}$ M, from about $10^{-10}$ M to about $5 \times 10^{-10}$ M, from about $5 \times 10^{-10}$ M to about $10^{-11}$ M to about $5 \times 10^{-11}$ M to about $10^{-12}$ M, or greater. In some embodiments, e.g., where a subject synthetic regulator comprises two or more linker domains, each of the linker domains may provide for attachment to a polypeptide with an affinity of less than about $10^{-9}$ M, but together the two or more linker domains provide for a binding affinity that is $10^{-9}$ M or greater.

Covalent Linkage to an Amino Acid Residue

In some embodiments, the linker domain provides for stable association, e.g., a covalent linkage, with an amino acid side chain in a polypeptide. Linkage of the synthetic regulator to a polypeptide can be via a tyrosine residue, a tryptophan residue, a serine residue, a threonine residue, cysteine residue, a histidine residue, an arginine residue, a lysine residue, an aspartic acid residue, a glutamic acid residue, or any natural or unnatural amino acid in the polypeptide that is accessible for reacting with the linker domain of the synthetic regulator. Suitable binding moieties include, but are not limited to, a maleimide, an acrylic ester, an acrylic amide (an acrylamide), an α-haloacetamide, an epoxide, an O-succinimidyl ester, a disulfide, and a methanethiosulfonate compound. In some embodiments, the binding moiety is other than a bromomethyl moiety, e.g, in some embodiments, a bromomethyl moiety is specifically excluded. For examples of covalent linkage to an amino acid residue see e.g. Hermanson (1996) Bioconjugate Techniques, Academic Press.

Where the amino acid to which the synthetic regulator is to be linked is a cysteine residue, the linker domain will comprise a moiety such as, e.g, a vinylsulfone group, maleimide; a substituted maleimide, such as maleic anhydride; orthopyridyl-disulfide; a methanethiosulfonate; a disulfide; and the like. Where the amino acid to which the synthetic regulator is to be linked is a lysine residue, the linker domain will in some embodiments comprise a moiety such as, e.g, carbodiimide EDC (1-(3-dimethylaminopropyl)-3-ethylcarbodiimide hydrochloride). Where the amino acid to which the synthetic regulator is to be linked is an arginine residue, the linker domain will comprise, e.g, 2,3-butanedione, phenylglyoxal, or glyoxal.

For example, cysteinyl residues most commonly are reacted with α-haloacetates (and corresponding amides), such as chloroacetic acid or chloroacetamide, to give carboxymethyl or carboxyamidomethyl derivatives. Cysteinyl residues also are reacted with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are reacted with diethylpyrocarbonate at pH 5.5-7.0 because this agent is relatively specific for the histidyl side chain. Para-bromophenacyl bromide also is useful; the reaction is generally performed in 0.1 M sodium cacodylate at pH 6.0. Lysinyl and amino terminal residues are reacted with succinic acid or other carboxylic acid anhydrides. Other suitable reagents for reacting with α-amino-containing residues include imidoesters such as methyl picolinimidate; pyridoxal phosphate; pyridoxal; chloroborohydride; trinitrobenzenesulfonic acid; O-methylisourea; and 2,4-pentanedione. Arginyl residues are reacted with one or several conventional reagents, among them phenylglyoxal, 2,3-butanedione, or 1,2-cyclohexanedione. Carboxyl side groups (aspartyl or glutamyl) are reacted with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide.

The binding moiety of the linker domain will in some embodiments include an alkylating agent, acylating agent, ketone, aldehyde, sulphonate or a phosphorylating agent. Examples of particular binding moieties include, but are not limited to fluorophosphonyl, fluorophosphoryl, fluorosulfonyl, alpha-haloketones or aldehydes or their ketals or acetals, respectively, alpha-haloacyls, nitriles, sulfonated alkyl or aryl thiols, iodoacetylamide group, maleimides, sulfonyl halides and esters, isocyanates, isothiocyanantes, tetrafluorophenyl esters, N-hydroxysuccinimidyl esters, acid halides, acid anhydrides, unsaturated carbonyls, alkynes, hydroxamates, alpha-halomethylhydroxamates, aziridines, epoxides, or arsenates and their oxides. Suitable sulfonyl groups include sulfonates, sulfates, sulfinates, sulfamates, etc., in effect, any reactive functionality having a sulfur group bonded to two oxygen atoms. Suitable epoxides include aliphatic, aralkyl, cycloaliphatic and spiro epoxides.

Non-Covalent Stable Association

In some embodiments, the stable association between the synthetic regulator and the polypeptide is a non-covalent association. Non-covalent associations include, e.g., biotin-avidin linkages, where the polypeptide comprises a biotin moiety and the synthetic linker includes a linker domain comprising an avidin moiety. Non-covalent associations further include metal ion-binding associations; and arsenic-binding associations. For example, in some embodiments, the ligand-binding polypeptide comprises two or more histidine residues positioned such that they bind a metal such as $Ni^{+2}$, $Co^{+2}$, $Fe^{+3}$, $Al^{+3}$, $Zn^{+2}$ or $Cu^{+2}$; and the linker domain of the synthetic regulator includes a binding moiety that coordinates the metal ion. For metal-chelating amino acid sequences, see, e.g., U.S. Pat. No. 5,284,933; U.S. Pat. No. 5,310,663; U.S. Pat. No. 4,569,794; U.S. Pat. No. 5,594,115; and U.S. Patent Publication No. US2002/0164718. Metal-chelating amino acid sequences include, but are not limited to, $(His)_6$. As another non-limiting example, in some embodiments the ligand-binding polypeptide comprises a tetra-cysteine motif; and the linker domain of the synthetic regulator includes a binding moiety that contains arsenic. See, e.g., U.S. Pat. No. 6,831,160.

Other means of forming a stable association between a synthetic regulator and a ligand-binding polypeptide include tyrosine and tryptophan derivatization chemistry; click chemistry; benzyl guanine transferase; and the like.

The binding moiety of the linker domain will in some embodiments include a functional group commonly used in photoaffinity labeling, such as benzophenones, aryl azides, diazonium ions, diazo compounds, and diazirines. See e.g. Hermanson (1996) Bioconjugate Techniques, Academic Press.

Ligand

As used herein, the term "ligand" refers to a molecule (e.g., a small molecule, a peptide, or a protein) that binds to a polypeptide and effects a change in an activity of the polypeptide, and/or effects a change in conformation of the polypeptide, and/or affects binding of another polypeptide to the polypeptide. Ligands include agonists, partial agonists, inverse agonists, antagonists, allosteric modulators, and blockers.

In some embodiments, the ligand is a naturally-occurring ligand. In other embodiments, the ligand is a synthetic ligand. In other embodiments, the ligand is an endogenous ligand. In some embodiments, the ligand is an agonist. In other embodiments, the ligand is an inverse agonist. In other embodiments, the ligand is a partial agonist. In other embodiments, the ligand is an antagonist. In other embodiments, the ligand is an allosteric modulator. In other embodiments, the ligand is a blocker. The term "antagonist" generally refers to an agent that binds to a ligand-binding polypeptide and inhibits an activity of the ligand-binding polypeptide. An "antagonist" may be an agent that binds to an allosteric site but does not activate the ligand-binding polypeptide; instead, the antagonist generally excludes binding by an agonist and thus prevents or hinders activation. The term "blocker" refers to an agent that acts directly on the active site, pore, or allosteric site. Ligands suitable for use herein bind reversibly to a ligand-binding site of a ligand-binding polypeptide.

The ligand is selected based in part on the activity of the polypeptide to which the synthetic regulator will be attached. For example, a ligand for a hormone-binding transcription factor is a hormone, or a synthetic analog of the hormone. A ligand for a tetracycline transactivator is tetracycline or a synthetic analog thereof. A ligand for an enzyme will in some embodiments be a synthetic agonist or antagonist of the enzyme. In some embodiments, a ligand will block the ligand-binding site. A ligand for a ligand-gated ion channel will in some embodiments be a naturally-occurring ligand, or a synthetic version of the ligand, e.g., a synthetic analog of the ligand. In some embodiments, the ligand is other than an acetylcholine receptor ligand. In some embodiments, the ligand is other than trimethylammonium.

In some embodiments, a ligand is a small molecule ligand. Small molecule ligands generally have a molecular weight in a range of from about 50 daltons to about 3000 daltons, e.g., from about 50 daltons to about 75 daltons, from about 75 daltons to about 100 daltons, from about 100 daltons to about 250 daltons, from about 250 daltons to about 500 daltons, from about 500 daltons to about 750 daltons, from about 750 daltons to about 1000 daltons, from about 1000 daltons to about 1250 daltons, from about 1250 daltons to about 1500 daltons, from about 1500 daltons to about 2000 daltons, from about 2000 daltons to about 2500 daltons, or from about 2500 daltons to about 3000 daltons.

In other embodiments, a ligand is a peptide ligand. Peptide ligands can have a molecular weight in a range of from about 1 kDa to about 20 kDa, e.g., from about 1 kDa to about 2 kDa, from about 2 kDa to about 5 kDa, from about 5 kDa to about 7 kDa, from about 7 kDa to about 10 kDa, from about 10 kDa to about 12 kDa, from about 12 kDa to about 15 kDa, or from about 15 kDa to about 20 kDa.

Suitable ligands include, but are not limited to, ligands that block or activate the function of a ligand-binding protein, where ligand-binding proteins include channels; receptors (including, but not limited to, ionotropic receptors that bind transmitters; ionotropic receptors that bind hormones; metabotropic receptors; receptor tyrosine kinases; growth factor receptors; and other membrane receptors that signal by binding to soluble or membrane-bound or extracellular matrix-bound small molecules or proteins); transporters (including but not limited to ion transporters, organic molecule transporters, peptide transporters, and protein transporters); enzymes (including but not limited to kinases; phosphatases; ubiquitin ligases; acetylases; oxo-reductases; lipases; enzymes that add lipid moieties to proteins or remove them; proteases; and enzymes that modify nucleic acids, including but not limited to ligases, helicases, topoisomerases, and telomerases); motor proteins (including kinesins, dyenins and other microtubule-based motors, myosins and other actin-based motors, DNA and RNA polymerases and other motors that track along polynucleotides); scaffolding proteins; adaptor proteins; cytoskeletal proteins; and other proteins that localize or organize protein domains and superstructures within cells.

Suitable ligands include, but are not limited to, ligands that function as general anesthetics; ligands that function as local anesthetics; ligands that function as analgesics; synthetic and semi-synthetic opioid analgesics (e.g., phenanthrenes, phenylheptylamines, phenylpiperidines, morphinans, and benzomorphans) where exemplary opioid analgesics include morphine, oxycodone, fentanyl, pentazocine, hydromorphone, meperidine, methadone, levorphanol, oxymorphone, levallorphan, codeine, dihydrocodeine, hydrocodone, propoxyphene, nalmefene, nalorphine, naloxone, naltrexone, buprenorphine, butorphanol, nalbuphine, and pentazocine; ionotropic glutamate receptor agonists and antagonists, e.g., N-methyl-D-aspartate (NMDA) receptor agonists and antagonists, kainate (KA) receptor agonists and antagonists, and α-amino-3-hydroxy-5-methylisoxazole-4-propionic acid (AMPA) receptor agonists and antagonists; non-opioid analgesics, e.g., acetylsalicylic acid, choline magnesium trisalicylate, acetaminophen, ibuprofen, fenoprofen, diflusinal, and naproxen; muscarinic receptor agonists; muscarinic receptor antagonists; acetylcholine receptor agonists; acetylcholine receptor antagonists; serotonin receptor agonists; serotonin receptor antagonists; enzyme inhibitors; a benzodiazepine, e.g. chlordiazepoxide, clorazepate, diazepam, flurazepam, lorazepam, oxazepam, temazepam or triazolam; a barbiturate sedative, e.g. amobarbital, aprobarbital, butabarbital, butabital, mephobarbital, metharbital, methohexital, pentobarbital, phenobartital, secobarbital, talbutal, theamylal, or thiopental; an $H_1$ antagonist having a sedative action, e.g. diphenhydramine, pyrilamine, promethazine, chlorpheniramine, or chlorcyclizine; an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, topiramate, neramexane, or perzinfotel; an alpha-adrenergic, e.g. doxazosin, tamsulosin, clonidine, guanfacine, dexmetatomidine, modafinil, phentolamine, terazasin, prazasin or 4-amino-6,7-dimethoxy-2-(5-methane-sulfonamido-1,2,3,4-tetrahydroisoquino-1-2-yl)-5-(2-pyridyl) quinazoline; a tricyclic antidepressant, e.g. desipramine, imipramine, amitriptyline, or nortriptyline; an anticonvulsant, e.g. carbamazepine, lamotrigine, topiratmate, or valproate; a tachykinin (NK) antagonist, particularly an NK-3, NK-2 or NK-1 antagonist, e.g. (αR,9R)-7-[3,5-bis(trifluoromethyl) benzyl]-8,9,10,11-tetrahydro-9-m-ethyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis (trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S); a muscarinic antagonist, e.g oxybutynin, tolterodine, propiverine, tropsium chloride, darifenacin, solifenacin, temiverine, or ipratropium; a cyclooxygenase-2 (COX-2) selective inhibitor, e.g. celecoxib, rofecoxib, parecoxib, valdecoxib, deracoxib, etoricoxib, or lumiracoxib; a vanilloid receptor agonist (e.g. resinferatoxin) or antagonist (e.g. capsazepine); a beta-adrenergic such as propranolol; a 5-HT receptor agonist or antagonist, e.g., a $5\text{-}HT_{1B/1D}$ agonist such as eletriptan, sumatriptan, naratriptan, zolmitriptan or rizatriptan; a $5\text{-}HT_{2A}$ receptor antagonist such as R(+)-α-(2, 3-dimethoxy-phenyl)-1-[2-(4-fluorophenylethyl)]-4-piperidin-emethanol (MDL-100907); and the like.

Other suitable ligands include, but are not limited to, lidocaine, novocaine, xylocalne, lignocaine, novocaine, carbocaine, etidocaine, procaine, prontocaine, prilocalne, bupivacaine, cinchocaine, mepivacaine, quinidine, flecamide, procaine, N-[[2'-(aminosulfonyl)biphenyl-4-yl]methyl]-N'-(2,2'-bithien-5-ylmethyl)succinamide (BPBTS), QX-314, saxitoxin, tetrodotoxin, and a type III conotoxin.

Suitable ligands for $K^+$ channels include, but are not limited to, quaternary ammonium (e.g., tetraethyl ammonium, tetrabutylammonium, tetrapentylammonium), 4-aminopyridine, sulfonylurea, Glibenclamide; Tolbutamide; Phentolamine, qiunine, qunidine, peptide toxins (e.g., charybdotoxin, agitoxin-2, apamin, dendrotoxin, VSTX1, hanatoxin-1, hanatoxin-2, and Tityus toxin K-α. Suitable ligands for $Na^+$ channels include, but are not limited to, tetrodotoxin, saxitoxin, guanidinium, polyamines (e.g. spermine, cadaverine, putrescine, μ-conotoxin, and δ-conotoxin.

Suitable ligands for cyclic nucleotide gated (CNG) and hyperpolarization-activated cyclic nucleotide-modulated (HCN) channels include, but are not limited to, 1-cis diltiazem and ZD7288. Suitable ligands for glycine receptors include, but are not limited to, strychnine and picrotoxin. Suitable ligands for nicotinic acetylcholine receptors include, but are not limited to, (+)tubocurarine, Methyllycaconitine, gallamine, Nicotine; Anatoxin A, epibatidine, ABT-94, Lophotoxin, Cytisine, Hexamethonium, Mecamylamine, and Dihydro-β erythroidine.

Suitable ligands for GABA receptors include, but are not limited to, Muscimol, THIP, Procabide, bicuculine, picrotoxin, gabazine, gabapentin, diazepam, clonazepam, flumazenil, a β-carboline carboxylate ethyl ester, baclofen, faclofen, and a barbiturate.

Many suitable ligands will be known to those skilled in the art; and the choice of ligand will depend, in part, on the target (e.g., receptor, ion channel, enzyme, etc.) to which the ligand binds.

Exemplary Synthetic Regulators

Non-limiting examples of synthetic regulators are depicted below. Those skilled in the art will appreciate that changes can be made to the exemplary synthetic regulators, e.g., changes in the length, stiffness, charge distribution, or bend angle of the photoisomerizable group, and/or changes in the linker moiety, and/or changes in the ligand can be made, according to the particular use of the synthetic regulator, according to the protein to which the synthetic regulator is targeted, etc.

Exemplary synthetic regulator 1 comprises a maleimide moiety for attachment to a cysteine residue in a protein; an azobenzene as a photoisomerizable moiety; and a quaternary ammonium group as the ligand (e.g., a ligand that blocks an ion channel). This synthetic regulator is referred to as MAL-AZO-QA in Example 1, and has the following structure:

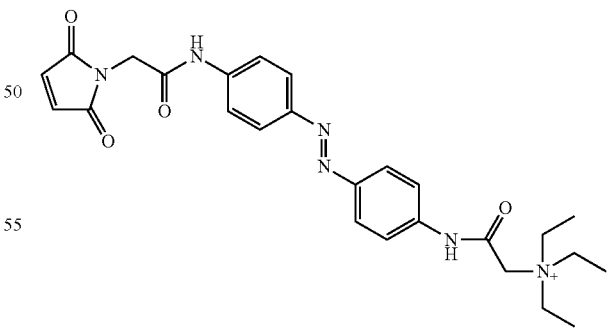

Exemplary synthetic regulator 2 is referred to as MAG-1 in Example 2. Exemplary synthetic regulator-2 comprises a maleimide moiety for attachment to a cysteine residue in a protein; an azobenzene as a photoisomerizable moiety; and a glutamate moiety as ligand agonist. Exemplary synthetic regulator 2 has the following structure:

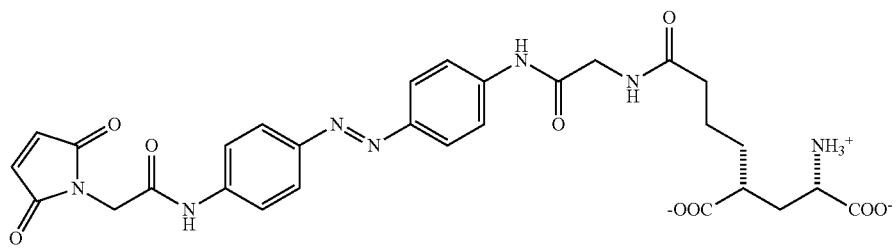

Exemplary synthetic regulator 3 is referred to as MAG-2 in Example 3. Exemplary synthetic regulator 3 comprises a maleimide moiety for attachment to a cysteine residue in a protein; an azobenzene as a photoisomerizable moiety; and a glutamate analog as the ligand moiety. MAG-2 differs from MAG-1 in that the photoisomerizable group in MAG-2 is longer than the photoisomerizable group in MAG-1. Exemplary synthetic regulator 3 has the following structure:

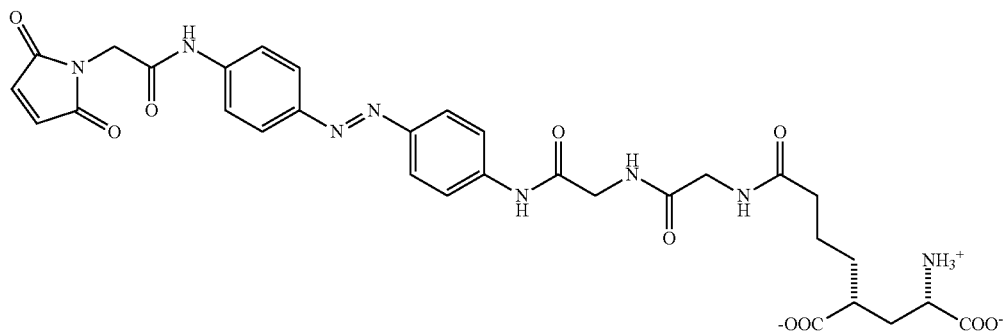

Exemplary synthetic regulator 4 is referred to as AAQ in Example 4. Exemplary synthetic regulator 4 comprises the reactive electrophile acrylamide for attachment to an amino acid residue in a target protein; an azobenzene as a photoisomerizable moiety; and a quaternary ammonium group as the ligand. Exemplary synthetic regulator 4 has the following structure:

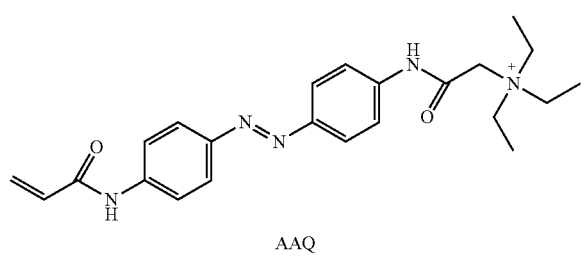

AAQ

Exemplary synthetic regulator 5 is referred to as CAQ in Example 4. Exemplary synthetic regulator 5 comprises the reactive electrophile chloroacetamide for attachment to an amino acid residue in a target protein; an azobenzene as a photoisomerizable moiety; and a quaternary ammonium group as the ligand. Exemplary synthetic regulator 5 has the following structure:

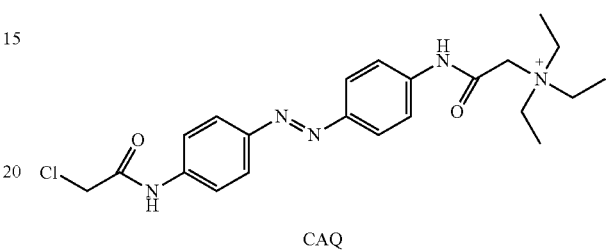

CAQ

Compositions

The present invention further provides compositions comprising a synthetic regulator. Compositions comprising a subject synthetic regulator will in many embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, Nonidet-P40, etc.; a protease inhibitor; and the like. In some embodiments, a subject composition comprising a subject synthetic regulator is a pharmaceutical composition, as described in more detail below.

Light-Regulated Polypeptides

The present invention further provides a light-regulated polypeptide, where a subject light-regulated polypeptide comprises a ligand-binding polypeptide and a subject synthetic regulator of protein function in stable association with the ligand-binding polypeptide. The synthetic regulator of protein function is stably associated with the ligand-binding polypeptide at or near a ligand binding site of the ligand-binding polypeptide. In some embodiments, a subject light-regulated polypeptide is isolated, e.g., free of other polypeptides or other macromolecules. In other embodiments, a subject light-regulated polypeptide is membrane-associated and is present in vitro. In other embodiments, a subject light-regulated polypeptide is present in a living cell in vitro or in vivo. In other embodiments, a subject light-regulated polypeptide is present in a membrane of a living cell in vitro or in vivo. In other embodiments, a subject light-regulated polypeptide is present in a living cell in a tissue in vitro or in vivo. In other embodiments, a subject light-regulated polypeptide is present in a living cell in a multicellular organism.

The synthetic regulator is stably associated with the ligand-binding polypeptide or near a ligand binding site of a ligand-binding polypeptide. For example, the synthetic regulator is stably associated with an amino acid side chain or other linkage group (e.g., a sugar moiety, a high affinity moiety such as biotin, etc.) in the ligand-binding polypeptide such that, in one configuration, the ligand binds to the ligand binding site and effects a change in an activity of the polypeptide. In some embodiments, the synthetic regulator is stably associated with a linkage group that is from about 1 Å to about 50 Å away from the ligand binding site, e.g., the synthetic regulator is covalently linked to a site that is from about 1 Å to about 5 Å, from about 5 Å to about 7 Å, from about 7 Å to about 10 Å, from about 10 Å to about 15 Å, from about 15 Å to about 20 Å, from about 20 Å to about 25 Å, from about 25 Å to about 30 Å, from about 30 Å to about 35 Å, from about 35 Å to about 40 Å, from about 40 Å to about 45 Å, or from about 45 Å to about 50 Å from the ligand binding site.

A change in the wavelength and/or intensity of light ($\Delta\lambda$) to which the light-regulated polypeptide is exposed results in a change in ligand binding to a ligand-binding site of the light-regulated polypeptide, e.g., results in a change in binding of the ligand portion of the synthetic regulated to the ligand-binding site of the light-regulated polypeptide. A "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. Repetitive changing from $\lambda_1$ to $\lambda_2$, then from $\lambda_2$ to $\lambda_1$, and back, e.g., switching from a first wavelength to a second wavelength, and back again repeatedly, is also contemplated. Repetitive changing from light to darkness, from darkness to light, etc., is also contemplated.

In some embodiments, the change in wavelength (from $\lambda_1$ to $\lambda_2$; from light to darkness; or from darkness to light) results in a change in binding of the ligand to a ligand-binding site. As used herein, a "change in binding of a ligand to a ligand-binding site" includes increased binding and decreased binding. As used herein, "increased binding" includes one or more of: an increased probability of binding of the ligand to the ligand-binding site; an increased binding affinity of the ligand for the ligand-binding site; an increased local concentration of the ligand at the ligand-binding site; and an increased occupancy of the ligand in the ligand-binding site. As used herein, "decreased binding" includes one or more of: a decreased probability of binding of the ligand to the ligand-binding site; a decreased binding affinity of the ligand for the ligand-binding site; a decreased local concentration of the ligand at the ligand-binding site; and a decreased occupancy of the ligand in the ligand-binding site. As used herein, the term "change in wavelength" to which a synthetic regulator is exposed, or to which a ligand-binding polypeptide/synthetic light regulator complex is exposed, refers to a change in wavelength from $\lambda_1$ to $\lambda_2$; a change from light to darkness; or a change from darkness to light. An increase in binding includes an increase of from about 10% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some embodiments, the ligand has a first probability of binding to the ligand site at a first wavelength of light; the ligand has a second probability of binding to the ligand binding site at a second wavelength of light; and the second probability is lower than the first probability. In other embodiments, the ligand has a first probability of binding to the ligand site at a first wavelength of light; the ligand has a second probability of binding to the ligand binding site at a second wavelength of light; and the second probability is higher than the first probability. In other embodiments, ligand has a first probability of binding to the ligand site when exposed to light; the ligand has a second probability of binding to the ligand binding site in the absence of light (e.g., in darkness); and the second probability is lower than the first probability. In other embodiments, the ligand has a first probability of binding to the ligand site when exposed to light; the ligand has a second probability of binding to the ligand binding site in the absence of light and the second probability is higher than the first probability.

The local concentration of the ligand portion of the synthetic regulator at the ligand binding site in a subject light-regulated polypeptide is high. For example, the local concentration of the ligand portion of the synthetic regulator at the ligand binding site in a subject light-regulated polypeptide ranges from about 500 nM to about 50 mM, e.g., from about 500 nM to about 750 nM, from about 750 nM to about 1 mM, from about 1 mM to about 5 mM, from about 5 mM to about 10 mM, from about 10 mM to about 20 mM, from about 20 mM to about 30 mM, or from about 30 mM to about 50 mM.

Change in Wavelength Resulting in Binding of the Ligand to the Ligand-Binding Site or Higher Affinity Ligand Binding to Ligand-Binding Site In some embodiments, a change in the wavelength of light to which the light-regulated polypeptide is exposed results in an increase in binding affinity of the ligand portion of a subject synthetic regulator for a ligand-binding site of the light-regulated polypeptide. For example, in some embodiments, a change in wavelength of light to which the light-regulated polypeptide is exposed results in an at least about 10%, at least about 20%, at least about 30%, at least about 50%, at least about 75%, at least about 2-fold, at least about 5-fold, at least about 10-fold, at least about 25-fold, at least about 50-fold, at least about 100-fold, at least about 250-fold, at least about 500-fold, at least about $10^3$-fold, at least about $5\times10^3$-fold, at least about $10^4$-fold, at least about $5\times10^4$-fold, or greater, increase in binding affinity.

Where the ligand is an agonist, the change in wavelength will in some embodiments result in activation of the light-regulated polypeptide. Where the ligand is an agonist, the change in wavelength will in some embodiments result in desensitization of the light-regulated polypeptide. Conversely, where the ligand is an antagonist, the change in wavelength results in a block of activation of the light-regulated polypeptide, e.g., block of the ability to activate the light-regulated polypeptide with free agonist. Where the ligand is a blocker (e.g., a pore blocker of an ion channel, an active site blocker of an enzyme, or an interaction domain that binds to other biological macromolecules such as polypeptides or nucleic acids), the change in wavelength results in block of polypeptide activity.

Expressed another way, where the ligand is an agonist, and where a change in the wavelength of light to which the light-regulated polypeptide is exposed results in a higher binding affinity of the ligand moiety of the synthetic regulator to the ligand-binding site of the light-regulated polypeptide, the change in wavelength results in transition from an inactive state to an active state, or to a desensitized state. Where the ligand is an antagonist, the change in wavelength results in transition from a responsive state to an unresponsive state. Where the ligand is a blocker, the change in wavelength results in transition from an active state to an inactive state.

Change in Wavelength Resulting in Removal of Ligand from Ligand-Binding Site, or Reduced Binding Affinity In some embodiments, a change in the wavelength of light to which the light-regulated polypeptide is exposed results in removal of the ligand portion of a subject synthetic regulator from a ligand-binding site of the light-regulated polypeptide, e.g., the ligand is not bound to the ligand-binding site. In some embodiments, a change in the wavelength of light to which the light-regulated polypeptide is exposed results in reduced binding affinity of the ligand portion of a subject synthetic regulator for a ligand-binding site of the light-regulated polypeptide, e.g., the ligand has reduced binding affinity for he ligand-binding site. For example, in some embodiments, a change in the wavelength of light to which the light-regulated polypeptide is exposed results in a reduction of binding affinity of at least about 10%, at least about 20%, at least about 25%, at least about 30%, at least about 40%, at least about 50%, at least about 60%, at least about 70%, at least about 80%, at least about 90%, at least about 95%, or more.

Where the ligand is an agonist, the change in wavelength will in some embodiments result in deactivation of the light-regulated polypeptide. Where the ligand is an agonist, the change in wavelength will in some embodiments result in recovery from desensitization of the light-regulated polypeptide. Conversely, where the ligand is an antagonist, the change in wavelength results in activation of the light-regulated polypeptide, or results in removal of a blocker from the light-regulated polypeptide. Where the ligand is a blocker (e.g., a pore blocker of an ion channel, an active site blocker of an enzyme, or an interaction domain that binds to other biological macromolecules such as polypeptides or nucleic acids), the change in wavelength results in relief of a block in polypeptide activity and permits the polypeptide to function normally.

Expressed another way, where the ligand is an agonist, and where a change in the wavelength of light to which the light-regulated polypeptide is exposed results in removal (or non-binding) of the ligand moiety of the synthetic regulator from the ligand-binding site of the light-regulated polypeptide, the change in wavelength results in transition from an active state to an inactive state, or from a desensitized state to a responsive state. Where the ligand is an antagonist, the change in wavelength results in transition from an unresponsive state to a responsive state. Where the ligand is a blocker, the change in wavelength results in transition from an inactive state to an active state.

In some embodiments, the polypeptide is an enzyme, and the ligand binding site is a catalytic active site. In other embodiments, the ligand binding site is an allosteric site of the polypeptide. In other embodiments, the ligand binding site is a pore of an ion channel. In other embodiments, the ligand binding site is an interaction motif or domain through which the polypeptide interacts with other molecules (e.g., polypeptides; nucleic acids).

Ligand-Binding Polypeptides

Suitable ligand-binding polypeptides include any polypeptide having a ligand binding site. Suitable polypeptides include, but are not limited to, enzymes; ion channels; transporters; receptors; motor proteins; scaffolding proteins; adaptors; membrane trafficking proteins; cytoskeleton proteins; and transcription factors. Exemplary, non-limiting ligand-binding polypeptides include ligand-gated ion channels, receptor tyrosine kinases, G-protein coupled receptors, ion pumps; amino acid transporters; proteins involved in secretion; and the like. In some embodiments, the ligand-binding polypeptide is other than an acetylcholine receptor.

Enzymes include, but are not limited to, lipases; synthases; epoxidases; phosphorylases; kinases; oxidoreductases, e.g., oxidases, dehydrogenases, reductases, peroxidases, hydroxylases, and oxygenases; acylases; hydrolases, e.g., esterases, phosphatases, glycosidases, proteases, and peptidases; lyases, e.g., decarboxylases, aldolases, and dehydratases; transferases, e.g., sulfotransferases, aminotransferases, and transpeptidases; isomerases, e.g., racemases, epimerases, cis-trans isomerases, intramolecular oxidoreductases, and intramolecular transferases; ligases, e.g., DNA ligases, amino acid-RNA ligases, acid-thiol ligases, amide synthetases, peptide synthetases, and cyclo-ligases; and the like. In some embodiments, the ligand-binding protein is an enzyme chosen from lipases, esterases, proteases, glycosidases, glycosyl transferases, phosphatases, kinases, mono- and dioxygenases, haloperoxidazes, lignin peroxidases, diarylpropane peroxidazes, epozide hydrolazes, nitrile hydratases, nitrilases, transaminases, amidases, acylases, helicases, topoisomerases, polymerases, and synthetases.

Ion channels include, but are not limited to, cation channels; sodium ion channels; potassium ion channels (where potassium channels include, e.g., a Kv1 potassium channel; a Kv2 potassium channel; a Kv3 potassium channel; a Kv4 potassium channel; an HCN potassium channel, e.g., HCN1, HCN2; a HERG potassium channel; an EAG potassium channel; calcium ion channels; chloride ion channels; cyclic nucleotide-gated channels; 2-transmembrane domain channels, including channels selective for potassium, and less selective cation channels; water and glycerol channels; proton channels; and the like. In some embodiments, a cation channel is a voltage-gated cation channel, e.g., a voltage-gated sodium channel (e.g., Nav), a voltage-gated calcium channel (e.g., Cav), a voltage-gated potassium channel (e.g., Kv), or a proton channel (Hv). In some embodiments, an ion channel is an inward rectifier potassium channel (e.g., a member of the Kir family). In some embodiments, the ion channel is a ligand-gated ion channel. A variety of ligand-gated ion channels are known in the art. Suitable ion channels include pentameric receptors, e.g., nicotinic acetylcholine receptors; gamma aminobutyric acid (GABA) receptors; glycine receptors; and 5-hydroxytryptamine (5-HT) receptors. Other ligand-gated ion channels include a Ptxr channer, a glycine receptor (GlyR), ASIC, etc. Suitable ion channels also include tetrameric receptors, e.g., glutamate receptors, including N-methyl-D-aspartate (NMDA) receptors, non-NMDA receptors, α-amino-3-hydroxy-5-methylisoxazole-4-propionic acid (AMPA) receptors, an inotropic glutamate receptor (e.g., iGluR6), and kainate (KA) receptors; purinergic receptors, e.g., P1 receptors, P2 receptors; and the like. For a description of various potassium channels, see, e.g., Doyle et al. ((1998) *Science* 280:69-77) and references cited therein. In some embodiments, an ion channel is a G protein-coupled receptor (GPCR), e.g., a muscarinic GPCR, a dopaminergic GPCR, a serotonergic GPCR, an adrenergic GPCR, an opiate GPCR, a glutamate GPCR, a cannabanoid GPCR, a peptidergic GPCR, an olfactory GPCR, a gustatory GPCR, etc.

Transcription factors include, but are not limited to, ligand-binding proteins that control transcription and that are inducible by the ligand. Such proteins include, but are not limited to, an ecdysone receptor (see, e.g., Koelle et al. *Cell* 67:59 (1991); Christianson and Kafatos, *Biochem. Biophys. Res. Comm.* 193:1318 (1993); Henrich et al., *Nucleic Acids Res.* 18:4143 (1990); and U.S. Pat. No. 6,958,236); a retinoic acid receptor; a glucocorticoid receptor (see, e.g., Picard et al. (1988) *Cell* 54: 1073-1080); a tetracycline-transactivator protein (tTA) or a tet repressor (tetR) protein of the tetracycline repressor/activator system (see, e.g., WO 94/29442; WO 96/40892; and WO 96/01313). Suitable transcription factors also include proteins that enhance or repress transcription in a manner regulated by binding to other proteins or small ligands, e.g., CREB, and helix-loop-helix proteins.

Receptors include, but are not limited to, G-protein coupled receptors, e.g., opioid receptors (e.g., δ-opioid receptors, μ-opioid receptors, κ-opioid receptors), peptide hormone receptors, neurotransmitter receptors, odorant receptors, nicotinic acetylcholine receptors, a dopamine receptor, a muscarinic receptor, a serotonin receptor, and the like.

Also suitable is the ligand-binding domain of any of the aforementioned proteins. For example, in some embodiments, a subject light-regulated polypeptide comprises the ligand-binding domain of a ligand-binding polypeptide; and a subject synthetic regulator in stable association with the ligand-binding domain. In some embodiments, the ligand-binding polypeptide comprises the ligand-binding domain of a ligand-binding protein, fused to a heterologous protein. In some embodiments, the ligand-binding polypeptide is an isolated ligand-binding domain of a ligand-binding protein, e.g., lacking any other domains that may be present in the native polypeptide, such as regulatory domains, transmembrane domains, and the like.

In some embodiments, the ligand-binding protein is a wild-type polypeptide, e.g., the polypeptide has a wild-type or natives amino acid sequence, e.g., an amino acid sequence that has not been altered by recombinant methods. In other embodiments, the ligand-binding protein is a recombinant polypeptide. In some embodiments, the ligand-binding protein is a synthetic polypeptide. Recombinant polypeptides include variant polypeptides that have been engineered such that the amino acid sequence differs from a wild-type or naturally-occurring polypeptide. Variant polypeptides include polypeptides comprising an amino acid sequence that differs from the amino acid sequence of a corresponding wild-type or naturally-occurring polypeptide by one to 15 amino acids, e.g., where the amino acid sequence has been altered to include an amino acid that provides for attachment to the binding moiety of the linker domain of the synthetic regulator.

In some embodiments, the ligand-binding protein comprises one or more amino acid substitutions and/or insertions and/or deletions compared to the amino acid sequence of a naturally-occurring polypeptide. In some of these embodiments, the ligand-binding protein is a variant ligand-binding protein that comprises one or more amino acid substitutions, compared to a naturally-occurring protein, such that the variant ligand-binding protein comprises a moiety for stable association of synthetic regulator. For example, in some embodiments, an amino acid in a ligand-binding protein is substituted with a cysteine, and the synthetic regulator is covalently linked to the cysteine residue.

In some embodiments, the ligand-binding protein is a fusion protein, where the fusion protein includes the ligand-binding protein fused in-frame to a heterologous protein, e.g., a protein other than the ligand-binding protein, where the heterologous protein is also referred to as a "fusion partner." In some embodiments, the fusion partner is linked to the ligand-binding protein at the N-terminus of the ligand-binding protein. In other embodiments, the fusion partner is linked at the C-terminus of the ligand-binding protein. In other embodiments, the fusion partner is internal to the ligand-binding protein.

Suitable fusion partners include, but are not limited to, epitope tags; solubilization domains; polypeptides that provide for insertion into a biological membrane; polypeptides that provide for uptake into a cell, e.g., polypeptides that provide for uptake into the cytoplasm or into an intracellular compartment; polypeptides that selectively bind to native proteins, including at essential protein interaction interfaces; polypeptides that provide for subcellular localization; polypeptides that provide a detectable signal (e.g., fluorescent proteins; chromogenic proteins; enzymes that generate luminescent, fluorescent, or chromogenic products; and the like).

Suitable fusion partners include, but are not limited to, luciferase (e.g., firefly luciferase and derivatives thereof; *Renilla* luciferase and derivatives thereof); β-galactosidase; chloramphenicol acetyl transferase; glutathione S transferase; a green fluorescent protein (GFP), including, but not limited to, a GFP derived from *Aequoria victoria* or a derivative thereof, a number of which are commercially available; a GFP from a species such as *Renilla reniformis, Renilla mulleri,* or *Ptilosarcus guernyi*, as described in, e.g., WO 99/49019 and Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; a red fluorescent protein; a yellow fluorescent protein; a Lumio™ tag (e.g., a peptide of the sequence Cys-Cys-Xaa-Xaa-Cys-Cys, where Xaa is any amino acid other than cysteine, e.g., where Xaa-Xaa is Pro-Gly, which peptide is specifically bound by a fluorescein derivative having two As(III) substituents, e.g., 4',5'-bis(1,3,2-dithioarsolan-2-yl) fluorescein; see, e.g., Griffin et al. (1998) *Science* 281:269; Griffin et al. (2000) *Methods Enzymol.* 327:565; and Adams et al. (2002) *J. Am. Chem. Soc.* 124:6063); and the like.

Compositions

The present invention further provides compositions comprising a subject light-regulated polypeptide. Compositions comprising a subject light-regulated polypeptide will in many embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Methods of Generating a Light-Regulated Polypeptide

In some embodiments, a light-regulated polypeptide is generated by reacting a ligand-binding polypeptide with a subject synthetic regulator in a cell-free in vitro reaction. In other embodiments, a light-regulated polypeptide is generated by affinity labeling a ligand-binding polypeptide with a subject synthetic regulator, where the ligand-binding polypeptide is a wild-type, native, or endogenous polypeptide. In some embodiments, the ligand-binding polypeptide is associated with a living cell (in vitro or in vivo), the cell that comprises the ligand-binding polypeptide is contacted with the synthetic regulator, where the synthetic regulator binds to the ligand-binding polypeptide.

In some embodiments, the amino acid sequence of a polypeptide is modified to include an attachment amino acid at or near the ligand-binding site, where the attachment amino acid provides an attachment site for the binding moiety of the ligand domain of the synthetic regulator. For example, a single amino acid substitution is carried out to introduce a cysteine residue into a polypeptide, where the introduced cysteine residue provides a site for attachment of a synthetic regulator, e.g., where the linker domain includes a maleimide moiety.

As noted above, in some embodiments, a light-regulated polypeptide is generated by reacting a ligand-binding polypeptide with a subject synthetic regulator, where the ligand portion of the synthetic regulator binds to a ligand-binding site of the ligand-binding polypeptide, and the binding moiety of the linker domain is thus favored to form a stable association with any of a number of different amino acid residues near the ligand binding site. This method is referred to as "affinity labeling." This method is suitable for labeling isolated polypeptides in vitro; and is also suitable for labeling a polypeptide present in a living cell, either in vitro or in vivo. For example, this method is suitable for labeling an endogenous polypeptide present in a living cell, either in vitro or in vivo. Thus, the present invention provides a method of conferring light regulation on a polypeptide (e.g., a recombinant polypeptide, an endogenous polypeptide, a native polypeptide, a wild-type polypeptide), the method generally involving contacting a polypeptide comprising a ligand binding site with a subject synthetic regulator, where the ligand moiety of the synthetic regulator binds to the ligand-binding site of the polypeptide, where the synthetic regulator comprises a linker domain comprising a reactive electrophilic moiety, and where, after binding of the ligand to the ligand-binding site, the reactive electrophilic moiety binds to an amino acid side chain of the polypeptide, thereby conferring light regulation on the polypeptide, such that a light-regulated polypeptide is generated.

Cells

The present invention further provides a cell comprising a subject light-regulated polypeptide. A subject cell finds use in a variety of applications, e.g., screening applications, such as identification of agents that modulate the activity of a polypeptide; and research applications such as examination of a metabolic pathway, or other physiological event. Where the cell is used in a screening assay, the cell can be referred to as a "test cell."

In some embodiments, the cell is a eukaryotic cell in in vitro cell culture, and is grown as an adherent monolayer, or in suspension. In other embodiments, the cell is a eukaryotic cell and is part of a tissue or organ, either in vivo or in vitro. In other embodiments, the cell is a eukaryotic cell and is part of a living multicellular organism, e.g., a protozoan, an amphibian, a reptile, a plant, an avian organism, a mammal, a fungus, an algae, a yeast, a marine microorganism, a marine invertebrate, an arthropod, an isopod, an insect, an arachnid, etc. In other embodiments, the cell is a prokaryotic cell.

In other embodiments, the cell is a member of archaea, e.g., an archaebacterium. Archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicicum, Methanothermus fervidus, Archaeoglobus fulgidus, Thermoplasma acidophilum, Haloferax volcanni, Methanosarcina barkeri, Methanosaeta concilli, Methanospririllum hungatei, Methanomicrobium mobile*), and Korarchaeota.

In some embodiments, the cell is of a particular tissue or cell type. For example, where the organism is a plant, the cell is part of the xylem, the phloem, the cambium layer, leaves, roots, etc. Where the organism is an animal, the cell will in some embodiments be from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

A subject cell is in many embodiments a unicellular organism, or is grown in culture as a single cell suspension, or as monolayer. In some embodiments, a subject cell is a eukaryotic cell. Suitable eukaryotic cells include, but are not limited to, yeast cells, insect cells, plant cells, fungal cells, mammalian cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. In some embodiments, the neuronal cell is a primary cell isolated from an animal. In some embodiments, the neuronal cell or neuronal-liked cell is an immortalized cell line. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In other embodiments, the host cell is a plant cell. Plant cells include cells of monocotyledons ("monocots") and dicotyledons ("dicots"). Guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

Suitable prokaryotic cells include bacteria (e.g., Eubacteria) and archaebacteria. Suitable archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicicum, Methanothermus fervidus, Archaeoglobus fulgidus, Thermoplasma acidophilum, Haloferax volcanni, Methanosarcina barkeri, Methanosaeta concilli, Methanospririllum hungatei, Methanomicrobium mobile*), and Korarchaeota. Suitable eubacteria include, but are not limited to, any member of Hydrogenobacteria, Thermotogales, Green nonsulfphur bacteria, Denococcus Group, Cyanobacteria, Purple bacteria, Planctomyces, Spirochetes, Green Sulphur bacteria, Cytophagas, and Gram positive bacteria (e.g., *Mycobacterium* sp., *Micrococcus* sp., *Streptomyces* sp., *Lactobacillus* sp., *Helicobacterium* sp., *Clostridium* sp., *Mycoplasma* sp., *Bacillus* sp., etc.).

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the cell is *Escherichia coli*.

Membranes

The present invention further provides a membrane comprising a subject light-regulated polypeptide. In some embodiments, the membrane is a biological membrane (e.g., a lipid bilayer surrounding a biological compartment such as a cell, including artificial cells, or a membrane vesicle or sheet). In some embodiments, the membrane is part of a living cell, as described above. In other embodiments, the membrane is an artificial (synthetic) membrane, e.g., a planar membrane, a liposome, etc.

In some embodiments, the artificial membrane is a lipid bilayer. In other embodiments, the artificial membrane is a lipid monolayer. In some embodiments, the artificial membrane is part of a liposome. Liposomes include unilamellar vesicles composed of a single membrane or lipid bilayer, and multilamellar vesicles (MLVs) composed of many concentric membranes (or lipid bilayers).

Artificial membranes, and methods of making same, have been described in the art. See, e.g., U.S. Pat. No. 6,861,260; Kansy et al. (1998) *J. Med. Chem.* 41(7):1007-10; and Yang et al. (1996) *Advanced Drug Delivery Reviews* 23:229-256.

A subject artificial membrane will in some embodiments, include one or more phospholipids. In some embodiments, the artificial membrane comprises a mixture of phospholipids containing saturated or unsaturated mono or disubstituted fatty acids and a combination thereof. These phospholipids are in some embodiments selected from dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, and palmiticlinoleoylphosphatidic acid. Suitable phospholipids also include the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in such lysophosphatidyl derivatives will in some embodiments be palimtoyl, oleoyl, palmitoleoyl, linoleoyl myristoyl or myristoleoyl.

Methods of Modulating Protein Activity

The present invention provides methods of modulating protein activity. In certain aspects, the present invention provides methods of modulating activity of a subject light-regulated polypeptide, where the method generally involves changing the wavelength of light to which the light-regulated polypeptide is exposed. In certain aspects, the present invention provides methods of modulating activity of a ligand-binding polypeptide, where the method generally involves: a) contacting the ligand-binding polypeptide with a subject synthetic regulator, where the synthetic regulator binds to the ligand-binding polypeptide by affinity labeling, thereby generating a light-regulated polypeptide; and b) changing the wavelength of light to which the light-regulated polypeptide is exposed.

As noted above, a "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. In certain aspects, the present invention provides methods of modulating activity of a native (wild-type) polypeptide, where the method generally involves: a) contacting a polypeptide with a subject synthetic regulator, where the subject synthetic regulator binds to the polypeptide, forming a synthetic regulator/polypeptide complex; and b) changing the wavelength of light to which the synthetic regulator/polypeptide complex is exposed. As noted above, a "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. The synthetic regulator/polypeptide complex is also referred to as a "light-regulated polypeptide." In some embodiments, the synthetic regulator/polypeptide complex is generated by affinity labeling, as described above.

In some embodiments, the ligand-binding polypeptide or the light-regulated polypeptide is present in a cell-free in vitro system, e.g, the ligand-binding polypeptide or the light-regulated polypeptide is not associated with a cell. In other embodiments, the ligand-binding polypeptide or the light-regulated polypeptide is associated with a cell, e.g., the ligand-binding polypeptide or the light-regulated polypeptide is integrated into a cell membrane in a cell, the ligand-binding polypeptide or the light-regulated polypeptide is in the cytosol of a cell, the ligand-binding polypeptide or the light-regulated polypeptide is in an intracellular organelle, etc. In other embodiments, the ligand-binding polypeptide or the light-regulated polypeptide is in a synthetic membrane, e.g., in a planar synthetic membrane, in a liposome, in a membrane of an artificial cell, etc. In some embodiments, the cell-associated ligand-binding polypeptide or the cell-associated light-regulated polypeptide is in a cell in vitro, e.g., in a cell in a monolayer, in a cell in suspension, in an in vitro tissue, etc. In other embodiments, the cell-associated ligand-binding polypeptide or the cell-associated light-regulated polypeptide is in a cell in vivo, e.g., in a cell of an organism, e.g., a living organism.

In some embodiments, the change in wavelength (from $\lambda_1$ to $\lambda_2$; from light to darkness; or from darkness to light) results in a change in binding of the ligand to a ligand-binding site. As used herein, a "change in binding of a ligand to a ligand-binding site" includes increased binding and decreased binding. As used herein, "increased binding" includes one or more of: an increased probability of binding of the ligand to the ligand-binding site; an increased binding affinity of the ligand for the ligand-binding site; an increased local concentration of the ligand at the ligand-binding site; and an increased occupancy of the ligand in the ligand-binding site. As used herein, "decreased binding" includes one or more of: a decreased probability of binding of the ligand to the ligand-binding site; a decreased binding affinity of the ligand for the ligand-binding site; a decreased local concentration of the ligand at the ligand-binding site; and a decreased occupancy of the ligand in the ligand-binding site. As used herein, the term "change in wavelength" to which a synthetic regulator is exposed, or to which a ligand-binding polypeptide/synthetic light regulator complex is exposed, refers to a change in wavelength from $\lambda_1$ to $\lambda_2$; a change from light to darkness; or a change from darkness to light. An increase in binding includes an increase of from about 10% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some embodiments, the ligand has a first probability of binding to the ligand site at a first wavelength of light; the ligand has a second probability of binding to the ligand binding site at a second wavelength of light; and the second probability is lower than the first probability. In other embodiments, the ligand has a first probability of binding to the ligand site at a first wavelength of light; the ligand has a second probability of binding to the ligand binding site at a second wavelength of light; and the second probability is higher than the first probability. In other embodiments, ligand has a first probability of binding to the ligand site when exposed to light; the ligand has a second probability of binding to the ligand binding site in the absence of light (e.g., in darkness); and the second probability is lower than the first probability. In other embodiments, the ligand has a first probability of binding to the ligand site when exposed to light; the ligand has a second probability of binding to the ligand binding site in the absence of light and the second probability is higher than the first probability.

A change in wavelength can result in a change in activity of the light-regulated protein. "Activity" will depend, in part, on the ligand-binding polypeptide, and can include enzymatic activity (for enzymes); activity of an ion channel; activity of a receptor in transmitting a signal; etc.

In some embodiments, the change in wavelength results in binding of the ligand to the ligand-binding site of the light-regulated polypeptide. In some embodiments, the change in wavelength results in increased binding affinity of the ligand to the ligand-binding site for the light-regulated polypeptide. In these embodiments, where the ligand is an agonist, and the change results in activation of said light-regulated polypeptide; and where the ligand is an antagonist, the change results in block of activation of the light-regulated polypeptide; and where the ligand is an active site or pore blocker, the change results in inhibition of the light-regulated polypeptide; and where the ligand is a blocker of a site of interaction with other macromolecules, the change interferes with that interaction. In some embodiments, prolonged binding of an agonist to the ligand-binding site results in desensitization or inactivation of the light-regulated polypeptide. In other embodiments, binding of an antagonist blocks activation of the light-regulated polypeptide.

In other embodiments, the change in wavelength results in lack of binding of the ligand to the ligand-binding site, e.g., removal of the ligand from the ligand-binding site of the light-regulated polypeptide. In other embodiments, the change in wavelength results in reduced binding affinity of the ligand for the ligand-binding site, e.g., reduced binding affinity of ligand for the ligand-binding site of the light-regulated polypeptide.

In these embodiments, where the ligand is an antagonist, the change results in activation of said light-regulated polypeptide; and where the ligand is an agonist, the change results in deactivation of light-regulated polypeptide, or recovery from desensitization or inactivation.

In some embodiments, the light-regulated polypeptide is exposed to light of a first wavelength, where exposure to light of the first wavelength ($\lambda_1$) results in binding of the ligand to the ligand-binding site (or increased binding affinity of the ligand for the ligand-binding site); and the polypeptide is subsequently exposed to light of a second wavelength ($\lambda_2$), where exposure to light of the second wavelength results in removal of the ligand from the ligand-binding site (or reduced binding affinity of the ligand for the ligand-binding site). This change in wavelength from a first wavelength to a second wavelength ($\lambda_2$) can be repeated numerous times, such that the light is switched back and forth between $\lambda_1$ and $\lambda_2$. Switching between $\lambda_1$ and $\lambda_2$ results in switching or transition from a ligand-bound state to a ligand-unbound state.

In some embodiments, the light-regulated polypeptide is exposed to light of a first wavelength, where exposure to light of the first wavelength ($\lambda_1$) results in binding of the ligand to the ligand-binding site (or increased binding affinity of the ligand for the ligand-binding site); and the light is subsequently turned off, e.g., the polypeptide is in darkness, where keeping the polypeptide in darkness results in removal of the ligand from the ligand-binding site (or reduced binding affinity of the ligand for the ligand-binding site). This change from $\lambda_1$ to darkness can be reversed, e.g., from darkness to $\lambda_1$; and repeated any number of times, as described above. In other embodiments, a subject polypeptide is exposed to light of a first wavelength, where exposure to light of the first wavelength ($\lambda_1$) results in lack of binding of the ligand to the ligand-binding site (or reduced binding affinity of the ligand for the ligand-binding site); and the light is subsequently turned off, e.g., the polypeptide is in darkness, where keeping the polypeptide in darkness results in binding of the ligand to the ligand-binding site (or increased binding affinity of the ligand for the ligand-binding site). This change from $\lambda_1$ to darkness can be reversed, e.g., from darkness to $\lambda_1$; and repeated any number of times, as described above.

As noted above, the change in wavelength can be repeated any number of times, e.g., from $\lambda_1$ to $\lambda_2$ and from $\lambda_2$ to $\lambda_1$; or from $\lambda_1$ to darkness and from darkness to $\lambda_1$. Thus, a subject method provides for inducing a transition or switch from a ligand-bound state of a protein to a ligand-unbound state of the light-regulated protein, or from a high affinity state to a low affinity state. Depending on whether the ligand is an agonist or an antagonist, the protein will in some embodiments be switched from an active state to an inactive (or deactivated) state, or from an inactive (or deactivated) state to an active state.

The wavelength of light to which the light-regulated polypeptide is exposed ranges from $10^{-8}$ m to about 1 m, e.g., from about $10^{-8}$ m to about $10^{-7}$ m, from about $10^{-7}$ m to about $10^{-6}$ m, from about $10^{-6}$ m to about $10^{-4}$ m, from about $10^{-4}$ m to about $10^{-2}$ m, or from about $10^{-2}$ m to about 1 m. "Light," as used herein, refers to electromagnetic radiation, including, but not limited to, ultraviolet light, visible light, infrared, and microwave.

The wavelength of light to which the light-regulated polypeptide is exposed ranges in some embodiments from about 200 nm to about 800 nm, e.g., from about 200 nm to about 250 nm, from about 250 nm to about 300 nm, from about 300 nm to about 350 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, or from about 750 nm to about 800 nm, or greater than 800 nm.

In other embodiments, the wavelength of light to which the light-regulated polypeptide is exposed ranges from about 800 nm to about 2500 nm, e.g., from about 800 nm to about 900 nm, from about 900 nm to about 1000 nm, from about 1000 nm to about 1200 nm, from about 1200 nm to about 1400 nm, from about 1400 nm to about 1600 nm, from about 1600 nm to about 1800 nm, from about 1800 nm to about 2000 nm, from about 2000 nm to about 2250 nm, or from about 2250 nm to about 2500 nm. In other embodiments, the wavelength of light to which the light-regulated polypeptide is exposed ranges from about 2 nm to about 200 nm, e.g., from about 2 nm to about 5 nm, from about 5 nm to about 10 nm, from about 10 nm to about 25 nm, from about 25 nm to about 50 nm, from about 50 nm to about 75 nm, from about 100 nm, from about 100 nm to about 150 nm, or from about 150 nm to about 200 nm.

The difference between the first wavelength and the second wavelength can range from about 10 nm to about 800 nm or more, e.g., from about 10 nm to about 25 nm, from about 25 nm to about 50 nm, from about 50 nm to about 100 nm, from about 100 nm to about 200 nm, from about 200 nm to about 250 nm, from about 250 nm to about 500 nm, or from about 500 nm to about 800 nm. Of course, where the light-regulated polypeptide is switched from darkness to light, the difference in wavelength is from essentially zero to a second wavelength.

The intensity of the light can vary from about 1 W/m$^2$ to about 50 W/m$^2$, e.g., from about 1 W/m$^2$ to about 5 W/m$^2$, from about 5 W/m$^2$ to about 10 W/m$^2$, from about 10 W/m$^2$, from about 10 W/m$^2$ to about 15 W/m$^2$, from about 15 W/m$^2$ to about 20 W/m$^2$, from about 20 W/m$^2$ to about 30 W/m$^2$, from about 30 W/m$^2$ to about 40 W/m$^2$, or from about 40 W/m$^2$ to about 50 W/m$^2$. The intensity of the light can vary from about 1 µW/cm$^2$ to about 100 µW/cm$^2$, e.g., from about 1 µW/cm$^2$ to about 5 µW/cm$^2$, from about 5 µW/cm$^2$ to about 10 µW/cm$^2$, from about 10 µW/cm$^2$ to about 20 µW/cm$^2$, from about 20 µW/cm$^2$ to about 25 µW/cm$^2$, from about 25 µW/cm$^2$ to about 50 µW/cm$^2$, from about 50 µW/cm$^2$ to about 75 µW/cm$^2$, or from about 75 µW/cm$^2$ to about 100 µW/cm$^2$. In some embodiments, the intensity of light varies from about 1 µW/mm$^2$ to about 1 W/mm$^2$, e.g., from about 1 µW/mm$^2$ to about 50 µW/mm$^2$, from about 50 µW/mm$^2$ to about 100 µW/mm$^2$, from about 100 µW/mm$^2$ to about 500 µW/mm$^2$, from about 500 µW/mm$^2$ to about 1 mW/mm$^2$, from about 1 mW/mm$^2$ to about 250 mW/mm$^2$, from about 250 mW/mm$^2$ to about 500 mW/mm$^2$, or from about 500 mW/mm$^2$ to about 1 W/mm$^2$.

In some embodiments, the light-regulated polypeptide is regulated using sound, instead of electromagnetic (EM) radiation (light). For example, in some embodiments, the light-regulated polypeptide is regulated using ultrasound to effect a change from a first isomeric form to a second isomeric form.

The duration of exposure of the light-regulated protein to light can vary from about 1 µsecond (µs) to about 60 seconds (s) or more, e.g., from about 1 µs to about 5 µs, from about 5 µs to about 10 µs, from about 10 µs to about 25 µs, from about 25 µs to about 50 µs, from about 50 µs to about 100 µs, from about 100 µs to about 250 µs, from about 250 µs to about 500 µs, from about 500 µs to about 1 millisecond (ms), from about 1 ms to about 10 ms, from about 10 ms to about 50 ms, from about 50 ms to about 100 ms, from about 100 ms to about 500 ms, from about 500 ms to about 1 second, from about 1 second to about 5 seconds, from about 5 seconds to about 10 seconds, from about 10 seconds to about 15 seconds, from about 15 seconds to about 30 seconds, from about 30 seconds to about 45 seconds, or from about 45 seconds to about 60 seconds, or more than 60 seconds. In some embodiments, the duration of exposure of the light-regulated polypeptide to light varies from about 60 seconds to about 10 hours, e.g., from about 60 seconds to about 15 minutes, from about 15 minutes to about 30 minutes, from about 30 minutes to about 60 minutes, from about 60 minutes to about 1 hour, from about 1 hour to about 4 hours, from about 4 hours to about 6 hours, from about 6 hours to about 8 hours, or from about 8 hours to about 10 hours, or longer.

The duration of binding of the ligand portion of the synthetic regulator to the ligand-binding site can vary from less than one second to days. For example, in some embodiments, the duration of binding of the ligand portion of the synthetic regulator to the ligand-binding site varies from about 0.5 second to about 1 second, from about 1 second to about 5 seconds, from about 5 seconds to about 15 seconds, from about 15 seconds to about 30 seconds, from about 30 seconds to about 60 seconds, from about 1 minute to about 5 minutes, from about 5 minutes to about 15 minutes, from about 15 minutes to about 30 minutes, or from about 30 minutes to about 60 minutes. In other embodiments, the duration of binding of the ligand portion of the synthetic regulator to the ligand-binding site varies from about 60 minutes to about 2 hours, from about 2 hours to about 4 hours, from about 4 hours to about 8 hours, from about 8 hours to about 12 hours, from about 12 hours to about 18 hours, from about 18 hours to about 24 hours, from about 24 hours to about 36 hours, from about 36 hours to about 48 hours, from about 48 hours to about 60 hours, from about 60 hours to about 72 hours, from about 3 days to about 4 days, from about 4 days to about 5 days, or from about 5 days to about 7 days, or longer.

Modulating Activity of a Second, Non-Light-Regulated Polypeptide

In some embodiments, modulating the activity of a light-regulated polypeptide results in modulating the activity of a polypeptide other than the light-regulated polypeptide. Thus, in other aspects, the present invention provides methods of modulating activity of a polypeptide whose activity is modulated by modulating the activity of a light-regulated polypeptide. In some aspects, the present invention provides methods of modulating the activity of a non light-regulated polypeptide in a cell. The methods generally involve modulating an activity of a light-regulated polypeptide in the cell, where modulation of the activity of the light-regulated polypeptide in the cell modulates the activity of the non-light-regulated polypeptide.

A non-light-regulated polypeptide whose activity is modulated by modulating the activity of a light-regulated polypeptide includes a polypeptide whose activity is modulated by a change in voltage of a biological membrane, a polypeptide whose activity is modulated by depolarization of a biological membrane; a polypeptide whose activity is modulated by a change in intracellular concentration of an ion (e.g., a monovalent or divalent ion, e.g., a monovalent or divalent cation); a polypeptide whose activity is modulated by phosphorylation; and the like. As one non-limiting example, a light-regulated polypeptide comprises a glutamate receptor (ligand-gated ion channel) as the ligand-binding polypeptide, where the light-regulated polypeptide is in the plasma membrane of a cell. Light activation of the light-regulated glutamate receptor in the cell opens the channel, resulting in influx of ion and depolarization of the plasma membrane. Depolarization of the plasma membrane activates a voltage-gated ion channel, such as a calcium channel. Activation of the calcium channels is readily detected by standard methods, e.g., use of an indicator dye, etc.). As another non-limiting example, the light-regulated polypeptide comprises a GPCR as the ligand-binding polypeptide. Activation of the light-regulated GPCR activates an ion channel or an enzyme. Activation of the ion channel or enzyme is readily detected using standard methods, e.g., use of an indicator dye for the permeating ion, or a colorimetric, fluorimetric, or luminescence assay for the product of the enzyme. As another non-limiting example, the light-regulated polypeptide comprises a receptor tyrosine kinase (RTK); and activation of the light-regulated RTK results in phosphorylation of a downstream protein, e.g., a transcription factor. Activation of the transcription factor is readily detected by, e.g., detecting a transcript. As another non-limiting example, the light-regulated polypeptide comprises an opioid receptor. Modulation of the opioid receptor by exposure to light (or removal of light) can modulate a potassium ion channel; and modulation of a potassium ion channel is readily detected using standard methods, e.g., use of a dye for potassium ions.

Utility

A subject synthetic regulator, a subject light-regulated polypeptide, a subject cell, and a subject method of modulating protein function, are useful in a wide variety of research applications, pharmaceutical applications, screening assays, therapeutic applications, and the like.

Research Applications

In some embodiments, a subject synthetic regulator or a subject light-regulated polypeptide, is useful in studies of cell function, in studies of physiology of whole organisms, and the like. In some aspects, a subject synthetic regulator or a subject light-regulated polypeptide finds use in controlling gene expression.

For example, a subject synthetic regulator will in some embodiments include a ligand that binds to the ligand-binding site of a transcriptional regulator protein. A transcriptional regulator protein that includes such a synthetic regulator in stable association with the protein will be light regulated, e.g., will be a light-regulated transcription factor. Thus, gene expression can be controlled by changing the wavelength of light to which the light-regulated transcription factor is exposed.

In physiological studies, changing light exposure of a tissue, organ, or whole organism (or a part of a whole organism) that includes a light-regulated protein provides a method of regulating a function in the tissue, organ, or whole organism. For example, where the light-regulated protein comprises a ligand-binding protein that is a ligand-gated ion channel, and the synthetic regulator comprises the ligand for the ligand-gated ion channel, changing the wavelength of light to which the light-regulated protein is exposed will result in opening or closing of the ion channel, thereby altering ion concentration in cells in a manner that alters their activity (e.g., hormone or neurotransmitter secretion) or state (e.g., transcriptional or translational or metabolic state) or electrical firing, etc.

Screening Methods

The present invention provides methods of identifying an agent that modulates a function (e.g., an activity) of a polypeptide. The methods generally involve contacting a light-regulated polypeptide with a test agent; and determining the effect, if any, of the test agent on the activity of the light-regulated polypeptide (or on the activity of a polypeptide that is regulated by the light-regulated polypeptide). The effect, if any, of the test agent on the activity of the light-regulated polypeptide is determined by exposing the light-regulated polypeptide to light of a first wavelength. In the absence of the test agent, exposure of the light-regulated polypeptide to light of a first wavelength induces a transition from a ligand-unbound state to a ligand-bound state. In the presence of a test agent that affects binding of the ligand to the ligand-binding site, the transition from the ligand-unbound state to a ligand-bound state is inhibited.

In some embodiments, the light-regulated polypeptide is in vitro in solution (e.g., free of cells or membranes); and the assay is carried out in vitro. In other embodiments, the light-regulated polypeptide is in a membrane (e.g., a synthetic membrane) in the absence of a living cell (e.g., in a cell-free system); and the assay is carried out in vitro. In other embodiments, the light-regulated polypeptide is in a cell, e.g., a living cell in vitro or in vivo; and in some embodiments, the assay is carried out in vitro, and in other embodiments, the assay is carried out in vivo.

In some aspects, the present invention provides methods for identifying an agent that modulates a function (e.g., an activity) of a non-light-regulated polypeptide in the same solution, membrane, or cell, where the activity of the non-light-regulated polypeptide is modulated by modulating the activity of a light-regulated polypeptide. The methods generally involve contacting a light-regulated polypeptide (where the light-regulated polypeptide is in a solution, membrane, or cell) with a test agent; and determining the effect, if any, of the test agent on the activity of the non-light-regulated polypeptide (where the non-light regulated polypeptide is in the same solution, membrane, or cell as the light-regulated polypeptide), where the activity of the non-light-regulated polypeptide is modulated by changing the wavelength of light to which the cell is exposed. Whether the activity of the non-light regulated polypeptide is modulated is determined using an assay appropriate to the activity of the non-light-regulated polypeptide. For example, where the non-light-regulated polypeptide is a calcium channel, a calcium-sensitive dye, such as a Fura-2 dye, will in some embodiments be used to detect an effect of the test agent on the activity of the calcium channel. For example, where the non-light-regulated polypeptide is a sodium channel, a sodium-sensitive dye such as sodium-binding benzofuran isophthalate (SBFI) will in some embodiments be used to detect an effect of the test agent on the activity of the sodium channel.

In some embodiments, the light-regulated polypeptide is in a cell (e.g., is integrated into the plasma membrane, is in the cytosol of the cell, is in a subcellular organelle, is in the nucleus of the cell, or is integrated into a membrane of a subcellular organelle). In these embodiments, the cell comprising the light-regulated polypeptide is a "test cell." The methods generally involve contacting the test cell with a test agent; and determining the effect, if any, of the test agent on the activity of the light-regulated polypeptide.

In some embodiments, the test agent is one that inhibits induction of a transition from a first, ligand-bound state to a second, ligand-unbound state. For example, in some embodiments, a test agent of interest is one that inhibits induction of a transition from a first, ligand-unbound state to a second, ligand-bound state by at least about 5%, at least about 10%, at least about 15%, at least about 20%, at least about 25%, at least about 30%, at least about 40%, at least about 50%, at least about 60%, at least about 70%, or at least about 80%, or more, compared to the induction in the absence of the test agent.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising a subject polypeptide in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

The screening methods may be designed a number of different ways, where a variety of assay configurations and protocols may be employed, as are known in the art. The above components of the method may be combined at substantially the same time or at different times. In some embodiments, a subject method will include one or more washing steps.

In some embodiments, the ligand-binding, light regulated polypeptide is assayed in a membrane-free, cell free assay. In other embodiments, the ligand-binding, light regulated polypeptide is integrated into an artificial membrane. In other embodiments, the ligand-binding, light regulated polypeptide is integrated into a biological membrane. In other embodiments, the ligand-binding, light regulated is in a living cell, e.g., in the cytosol, in the nucleus, in an intracellular organelle, in the plasma membrane, or in an intracellular membrane of the cell.

Biological cells which are suitable for use in a subject screening assay include, but are not limited to, primary cultures of mammalian cells, transgenic (non-human) organisms and mammalian tissue. Cells in screening assays may be dissociated either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like.

Biological cells which are suitable for use in a subject screening assay include cultured cell lines (e.g., immortalized cell lines). Representative suitable cultured cell lines derived from humans and other mammals include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In some embodiments, the readout for an effect on the activity of the ligand-binding, light regulated polypeptide is a direct measure of the activity of the ligand-binding, light regulated polypeptide. A direct effect on the ligand-binding, light regulated polypeptide is detected using an assay appropriate to the particular protein. For example, where the ligand-binding, light regulated is an enzyme, any of a variety of assays can be used to detect enzymatic activity, and therefore to detect an effect of the test agent on enzymatic activity. As another example, where the ligand-binding, light regulated polypeptide is an ion channel, the effect, if any, of the test agent on the activity of the ion channel is in some embodiments detected by detecting a change in the intracellular concentration of an ion. A change in the intracellular concentration of an ion can be detected using an indicator appropriate to the ion whose influx is controlled by the channel. For example, where the ion channel is a potassium ion channel, a potassium-detecting dye is used; where the ion channel is a calcium ion channel, a calcium-detecting dye is used; etc.

In other embodiments, the readout for an effect on the activity of the ligand-binding, light regulated polypeptide is an effect on a second polypeptide whose activity is affected by the ligand-binding, light regulated polypeptide. For example, where the ligand-binding, light regulated polypeptide is an ion channel that controls influx of potassium into the cell, where an influx of potassium into the cell generates a voltage across the membrane, the effect of a test agent on activity of the ligand-binding, light regulated polypeptide can be detected by detecting a voltage generated across the membrane. In some embodiments, where the ligand-binding, light regulated polypeptide is an ion channel that controls influx of potassium into the cell, the ion channel controls opening of a calcium channel. In these embodiments, a calcium-sensitive dye is used to detect an effect of the test agent on the activity of the ligand-binding, light regulated ion channel.

Suitable voltage-sensitive dyes include, but are not limited to, merocyanine-oxazolone dyes (e.g., NK2367); merocyanine-rhodanine dyes (e.g., NK2495, NK2761, NK2776, NK3224, and NK3225); oxonol dyes (e.g., RH155, RH479, RH482, RH1691, RH1692, and RH1838); styryl dyes (e.g., RH237, RH414, RH421, RH437, RH461, RH795, JPW1063, JPW3028, di-4-ANEPPS, di-9-ANEPPS, di-2-ANEPEQ, di-12-ANEPEQ, di-8-ANEPPQ, and di-12-ANEPPQ); and the like.

Suitable intracellular $K^+$ ion-detecting dyes include, but are not limited to, $K^+$-binding benzofuran isophthalate and the like.

Suitable intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., *Methods in Cell Biology, Volume* 40: *A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999); *Calcium Signaling Protocols* (Methods in Molecular Biology), 2005, D. G. Lamber, ed., Humana Press.).

In particular embodiments of interest, a subject screening method is useful for identifying agents that reduce or relieve pain, e.g., agents that bind an opioid receptor, where the screening method involves detecting an effect, if any, of the test agent on the activity of a potassium channel or calcium channel that is regulated by the opioid receptor. In other embodiments, a subject screening method is useful for identifying agents that are selective for a particular receptor type or subtype, where the screening method involves determining the effect of the agent on a first subtype and a second subtype, where an effect on the first subtype, and a reduced effect (or substantially no effect) on the second subtype indicates selectivity of the test agent for the first subtype.

Therapeutic Applications

A subject synthetic regulator of protein function is suitable for use in a variety of therapeutic applications, which are also provided. In some embodiments, a subject synthetic regulator of protein function is useful in restoring light sensitivity to a retina that has reduced light sensitivity. In other embodiments, a subject synthetic regulator of protein function is useful as a local anesthetic. In other embodiments, a subject synthetic regulator is useful as an anti-convulsant, e.g., in the treatment of epilepsy.

Restoring Light Sensitivity to a Retina

The present invention provides a method for restoring light sensitivity to a retina, or conferring light sensitivity to a cell in the eye, the method generally involving administering to an individual in need thereof an effective amount of a subject synthetic regulator of protein function locally, e.g., in or around the eye.

A subject synthetic regulator that is suitable for this application comprises a ligand that confers light sensitivity on one or more cells in the eye, e.g., retinal pigment epithelial cells; and cells disposed in the neurosensory retina, for example, photoreceptor cells and Mueller cells. A pharmaceutical composition comprising a subject synthetic regulator is administered in or around the eye; the synthetic regulator attaches to a protein in a cell in the eye, and confers light sensitivity to the cell. Suitable pharmaceutical compositions are described in detail below. For example, the synthetic regulator can confer light sensitivity on a retinal ganglion.

A pharmaceutical composition comprising a subject synthetic regulator that confers light sensitivity on a cell can be delivered to the eye through a variety of routes. A subject pharmaceutical composition may be delivered intraocularly, by topical application to the eye or by intraocular injection into, for example the vitreous or subretinal (interphotoreceptor) space. Alternatively, a subject pharmaceutical composition may be delivered locally by insertion or injection into the tissue surrounding the eye. A subject pharmaceutical composition may be delivered systemically through an oral route or by subcutaneous, intravenous or intramuscular injection. Alternatively, a subject pharmaceutical composition may be delivered by means of a catheter or by means of an implant, wherein such an implant is made of a porous, non-porous or gelatinous material, including membranes such as silastic membranes or fibers, biodegradable polymers, or proteinaceous material. A subject pharmaceutical composition can be administered prior to the onset of the condition, to prevent its occurrence, for example, during surgery on the eye, or immediately after the onset of the pathological condition or during the occurrence of an acute or protracted condition.

The effects of therapy for an ocular disorder as described herein can be assessed in a variety of ways, using methods known in the art. For example, the subject's vision can be tested according to conventional methods. Such conventional methods include, but are not necessarily limited to, electroretinogram (ERG), focal ERG, tests for visual fields, tests for visual acuity, ocular coherence tomography (OCT), Fundus photography, Visual Evoked Potentials (VEP) and Pupillometry. In general, the invention provides for maintenance of a subject's vision (e.g., prevention or inhibition of vision loss of further vision loss due to photoreceptor degeneration), slows progression of vision loss, or in some embodiments, provides for improved vision relative to the subject's vision prior to therapy.

Exemplary conditions of particular interest which are amenable to treatment according to the methods of the invention include, but are not necessarily limited to, diabetic retinopathy, age-related macular degeneration (AMD or ARMD) (wet form); dry AMD; retinopathy of prematurity; retinitis pigmentosa (RP); diabetic retinopathy; and glaucoma, including open-angle glaucoma (e.g., primary open-angle glaucoma), angle-closure glaucoma, and secondary glaucomas (e.g., pigmentary glaucoma, pseudoexfoliative glaucoma, and glaucomas resulting from trauma and inflammatory diseases).

Further exemplary conditions amenable to treatment according to the invention include, but are not necessarily limited to, retinal detachment, age-related or other maculopathies, photic retinopathies, surgery-induced retinopathies, toxic retinopathies, retinopathy of prematurity, retinopathies due to trauma or penetrating lesions of the eye, inherited retinal degenerations, surgery-induced retinopathies, toxic retinopathies, retinopathies due to trauma or penetrating lesions of the eye.

Specific exemplary inherited conditions of interest for treatment according to the invention include, but are not necessarily limited to, Bardet-Biedl syndrome (autosomal recessive); Congenital amaurosis (autosomal recessive); Cone or cone-rod dystrophy (autosomal dominant and X-linked forms); Congenital stationary night blindness (autosomal dominant, autosomal recessive and X-linked forms); Macular degeneration (autosomal dominant and autosomal recessive forms); Optic atrophy, autosomal dominant and X-linked forms); Retinitis pigmentosa (autosomal dominant, autosomal recessive and X-linked forms); Syndromic or systemic retinopathy (autosomal dominant, autosomal recessive and X-linked forms); and Usher syndrome (autosomal recessive).

Local Anesthetic

The present invention provides a method of reducing or preventing pain in an individual, the method generally involving: a) administering to an individual in need thereof an effective amount of a subject synthetic regulator of protein function, where the synthetic regulator of protein function comprises a ligand that blocks a pain response or a pain signal, where the synthetic regulator binds to receptor or a channel, forming complex between the synthetic regulator and the receptor or channel; and b) exposing the receptor/regulator complex or channel/regulatory complex to a wavelength of light that provides for binding of the ligand to the receptor or channel. For example, in some embodiments, the protein is a cation channel, and the synthetic regulator binds to the cation channel, forming a cation channel/regulator complex, where the channel/regulator complex is exposed to a wavelength of light that provides for blocking of the channel, e.g., a $Na^+$ channel, an N-type $Ca^{2+}$ channel, etc.

An "effective amount" of a subject synthetic regulator is an amount that is effective to reduce pain by at least 30%, 40%, 60%, 70%, 80%, 90% or 100% for a period of time of from about 15 minutes to 5 days, e.g., from about 15 minutes to about 30 minutes, from about 30 minutes to about 60 minutes, from about 1 hour to about 4 hours, from about 4 hours to about 8 hours, from about 8 hours to about 16 hours, from about 16 hours to about 24 hours, from about 24 hours to about 36 hours, from about 36 hours to about 48 hours, from about 48 hours to about 3 days, or from about 3 days to about 5 days. The effectiveness of a subject synthetic regulator in treating nociceptive pain can be determined by observing one or more clinical symptoms or physiological indicators associated with nociceptive pain.

In these embodiments, a suitable synthetic regulator includes one that comprises, as a ligand, an opioid analgesic. Suitable ligands include, but are not limited to, morphine, oxycodone, fentanyl, pentazocine, hydromorphone, meperidine, methadone, levorphanol, oxymorphone, levallorphan, codeine, dihydrocodeine, hydrocodone, propoxyphene, nalmefene, nalorphine, naloxone, naltrexone, buprenorphine, butorphanol, nalbuphine, and pentazocine. In other embodiments, a suitable synthetic regulator comprises a ligand moiety selected from lidocaine, novocaine, xylocalne, lignocaine, novocaine, carbocaine, etidocaine, tetracaine, procaine, prontocaine, prilocalne, bupivacaine, cinchocaine, mepivacaine, quinidine, flecamide, procaine, N—[[2'-(aminosulfonyl)biphenyl-4-yl]methyl]-N'-(2,2'-bithien-5-ylm-ethyl)succinamide (BPBTS), QX-314, saxitoxin, tetrodotoxin, and a type III conotoxin.

The present invention provides pharmaceutical compositions comprising a subject synthetic regulator. In some embodiments, the pharmaceutical composition is suitable for administering to an individual in need of a local anesthetic. Individuals in need of a local anesthetic include an individual who is about to undergo a surgical procedure, and an individual who has undergone a surgical procedure within the last 5 minutes to within the last 72 hours. Individuals in need of a local anesthetic further include individuals having a wound, e.g., a superficial wound.

A pharmaceutical composition comprising a subject synthetic regulator may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A pharmaceutical composition comprising a subject synthetic regulator can optionally include a pharmaceutically acceptable carrier(s) that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, 7th ed. 1999); "Remington: The Science and Practice of Pharmacy" (Alfonso R. Gennaro ed., Lippincott, Williams & Wilkins, 20th 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, 4th edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Routes of administration suitable for the methods of the invention include both systemic and local administration. In some embodiments, a subject pharmaceutical composition comprising a subject synthetic regulator is administered locally. As non-limiting examples, a pharmaceutical composition useful for treating nociceptive pain can be administered orally; by subcutaneous pump; by dermal patch; by intravenous, subcutaneous or intramuscular injection; by topical drops, creams, gels, sprays, or ointments; as an implanted or injected extended release formulation; as a bioerodable or non-bioerodable delivery system; by subcutaneous minipump or other implanted device; by intrathecal pump or injection; or by epidural injection. In some embodiments, a subject pharmaceutical composition comprising a subject synthetic regulator is administered sublingually. In some embodiments, a subject pharmaceutical composition comprising a subject synthetic regulator is administered topically to gum tissue. In some embodiments, a subject pharmaceutical composition comprising a subject synthetic regulator is injected into gum tissue. In some embodiments, a subject pharmaceutical composition comprising a subject synthetic regulator is administered topically to the skin. In some embodiments, a subject pharmaceutical composition comprising a subject synthetic regulator is administered at or near a site of a surgical incision. In some embodiments, a subject pharmaceutical composition comprising a subject synthetic regulator is administered intramuscularly at the site of a surgical incision. For example, in some embodiments, a subject pharmaceutical composition comprising a subject synthetic regulator is administered at a surgical site, and before the surgical wound is closed, the synthetic regulator/target protein complex is exposed to light of a wavelength that induces binding of the ligand to the protein. In some embodiments, a subject pharmaceutical composition is administered (e.g., injected) at or near a nerve. Thus, in some embodiments, a subject pharmaceutical composition is formulated for injection at or near a nerve. For example, for oral surgery, a subject pharmaceutical composition is injected at or near a nerve in gum tissue.

In some embodiments, a subject pharmaceutical composition comprising a subject synthetic regulator is administered just before surgery, e.g., from about 1 minute to about 2 hours before surgery, e.g., from about 1 minute to about 5 minutes, from about 5 minutes to about 15 minutes from about 15 minutes to about 30 minutes, from about 30

A subject synthetic regulator comprising a ligand that provides for pain prevention is suitable for preventing or reducing pain in an individual in need thereof. Individuals in need of treatment with a subject synthetic regulator comprising a ligand that provides for pain prevention include individuals who are about to undergo surgery, e.g., individuals who are scheduled to undergo a surgical procedure in the next 5 minutes to 72 hours; individuals who are undergoing a surgical procedure; and individuals who have undergone a surgical procedure within the previous 5 minutes to 1 hour. Thus, individuals suffering from post-operative pain are suitable for treatment. A subject synthetic regulator comprising a ligand that provides for pain prevention is also suitable for preventing or reducing pain in an individual having a wound, e.g., a superficial wound.

Anti-Convulsant Applications

In some embodiments, a subject synthetic regulator comprises, as a ligand, a ligand for a sodium channel, a potassium channel, or a GABA receptor, where the ligand functions as an anti-convulsant. In some embodiments, the synthetic regulator is administered in a pharmaceutical composition, as described supra and infra.

Pharmaceutical Compositions

A subject synthetic regulator can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical 57-th ed., Dosage Forms and Drug Delivery Systems (1999) H. C. Ansel et al., eds. Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public In the subject methods, a subject synthetic regulator may be administered to the host using any convenient means capable of resulting in the desired reduction in disease condition or symptom. Thus, a subject synthetic regulator can be incorporated into a variety of formulations for therapeutic administration. More particularly, a subject synthetic regulator can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

A subject synthetic regulator can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject synthetic regulator can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

A subject synthetic regulator can be utilized in aerosol formulation to be administered via inhalation. A subject synthetic regulator can be formulated into pressurized acceptable propellants such as dichlorodifluoromethane, propane, nitrogen and the like.

Furthermore, a subject synthetic regulator can be made into suppositories by mixing with a variety of bases such as emulsifying bases or water-soluble bases. A subject synthetic regulator can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject synthetic regulator in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject synthetic regulator calculated in an amount sufficient to produce the desired effect in association with a pharmaceutically acceptable diluent, carrier or vehicle. The specifications for a subject synthetic regulator depend on the particular compound employed and the effect to be achieved, and the pharmacodynamics associated with each compound in the host.

A subject synthetic regulator can be administered as injectables. Injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a subject synthetic regulator is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a subject synthetic regulator can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, a subject synthetic regulator is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the synthetic regulator adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Ophthalmic Formulations

In some embodiments, a subject pharmaceutical composition comprises a subject synthetic regulator formulated for ophthalmic application. For ophthalmic application, solutions or medicaments are often prepared using a physiological saline solution as a major vehicle. Ophthalmic solutions should be maintained at a comfortable pH with an appropriate buffer system. The formulations may also contain conventional, pharmaceutically acceptable preservatives, stabilizers and surfactants.

Preservatives that may be used in a subject pharmaceutical composition include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

An ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which can be included in the ophthalmic preparations are chelating agents. A useful chelating agent is edetate disodium (ethylenediamine tetraacetate disodium; EDTA-disodium), although other chelating agents may also be used in place or in conjunction with it.

Dosages

In general, a subject synthetic regulator is administered in an amount of from about 10 ng to about 10 mg per dose, e.g., from about 10 ng to about 20 ng, from about 20 ng to about 25 ng, from about 25 ng to about 50 ng, from about 50 ng to about 75 mg, from about 75 ng to about 100 ng, from about 100 ng to about 125 ng, from about 125 ng to about 150 ng, from about 150 ng to about 175 ng, from about 175 ng to about 200 ng, from about 200 ng to about 225 ng, from about 225 ng to about 250 ng, from about 250 ng to about 300 ng, from about 300 ng to about 350 ng, from about 350 ng to about 400 ng, from about 400 ng to about 450 ng, from about 450 ng to about 500 ng, from about 500 ng to about 750 ng, from about 750 ng to about 1 mg, from about 1 mg to about 5 mg, or from about 5 mg to about 10 mg per dose. In some embodiments, the amount of a subject synthetic regulator per dose is determined on a per body weight basis.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, multiple doses of a subject synthetic regulator are administered. The frequency of administration of a subject synthetic regulator can vary depending on any of a variety of factors, e.g., severity of the symptoms, etc. For example, in some embodiments, a subject synthetic regulator is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in some embodiments, a subject synthetic regulator is administered continuously.

The duration of administration of a subject synthetic regulator, e.g., the period of time over which a subject synthetic regulator is administer, can vary, depending on any of a variety of factors, e.g., patient response, etc. For example, a subject synthetic regulator can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

A subject synthetic regulator is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. The subject synthetic regulator can be administered in a single dose or in multiple doses.

A subject synthetic regulator can be administered to a host using any available conventional methods and routes suitable for delivery of conventional drugs, including systemic or localized routes. In general, routes of administration contemplated by the invention include, but are not necessarily limited to, enteral, parenteral, topical, intraorbital, and intravitreous routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the subject synthetic regulator. Where systemic delivery is desired, administration typically involves invasive or systemically absorbed topical or mucosal administration of pharmaceutical preparations.

A subject synthetic regulator can also be delivered to the subject by enteral administration. Enteral routes of administration include, but are not necessarily limited to, oral and rectal (e.g., using a suppository) delivery.

Methods of administration of the subject synthetic regulator through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Kits

Also provided are kits that find use in practicing the subject methods, as described above. For example, in some embodiments, kits for practicing the subject methods include at least a synthetic regulator, as described above. In other embodiments, kits for practicing the subject methods include at least a light-regulated polypeptide as described above. In some embodiments, a subject kit includes a polypeptide and a subject synthetic regulator. In other embodiments, a subject kit includes a polypeptide with a subject synthetic regulator in stable association with the polypeptide. In other embodiments, kits for practicing the subject methods include at least a test cell as described above, or elements for constructing the same, e.g., expression vectors, etc. In some embodiments, a subject kit includes a cell (e.g., a eukaryotic cell or a prokaryotic cell), where the cell produces a protein to be controlled, directly or indirectly, by a subject synthetic regulator; and a subject synthetic regulator. Furthermore, additional reagents that are required or desired in the protocol to be practiced with the kit components may be present, which additional reagents include, but are not limited to: aqueous media, culture media, and the like. The kits may also include reference or control elements, e.g., that provide calibration signals or values for use in assessing the observed signal generated by an assay performed with the kit components. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, digital versatile disc, compact disk, etc., on which the information has been recorded. Yet another means that may be present is a website address which may be used via the internet to access the information at a removed site. Any convenient means may be present in the kits.

Systems

Also provided are systems that find use in practicing the subject methods, as described above. For example, in some embodiments, systems for practicing the subject methods include at least synthetic regulator as described above. In other embodiments, systems for practicing the subject methods include at least a light-regulated polypeptide as described above. In other embodiments, systems for practicing the subject methods include at least a test cell as described above. Furthermore, additional reagents that are required or desired in the protocol to be practiced with the system components may be present, which additional reagents include, but are not limited to: aqueous mediums, culture mediums, and the like. The systems may also include reference or control elements, e.g., that provide calibration signals or values for use in assessing the observed signal generated by an assay performed with the system components. The systems generally also include one or more candidate agents.

Devices

Also provided are high throughput (HT) devices that find use in practicing the subject methods, particularly HT embodiments thereof. The high throughput devices may have any convenient configuration, and generally include a plurality of two or more fluid containment elements in which assays can take place, agent administration elements and signal detection elements. For example, representative HT devices of the subject invention include a plate or substrate having a plurality of fluid-containing wells, reagent-adding equipment responsive to a computer for adding reagent, e.g., candidate agent, to the wells, measurement equipment for measuring at least one attribute of the sample or cells contained by the wells (e.g., for phenotype evaluation), a light source for providing light of different wavelengths to the contents of the wells, and moving equipment which is responsive to the computer for aligning one of the wells first with the reagent-adding component, then with the measurement device. See, e.g., U.S. Pat. No. 6,127,133. Also of interest are the devices described in U.S. Pat. Nos. 6,468,736 and 5,989,835. A feature of the HT devices of the present invention is that they include in at least one fluid containment element containing a test polypeptide, a test cell, or a test membrane as described above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Light-Activated Ion Channel

Methods
Synthesis of MAL-AZO-QA
MAL-AZO-QA was synthesized in a two-step coupling procedure from the commercially available 4,4'-azodianiline and the respective acid chlorides of the maleimide and quaternary ammonium components.
Patch Recordings from Oocytes
*Xenopus* oocytes were injected with 12.5-100 μg of mRNA encoding Shaker H4, with the following mutations: Δ6-46, E422C, T449V. We found that the effects of light on channel activity were largest for the TEA binding site mutant T449V as compared to the wild-type channel (T449) and two other mutants (T449Y, T449F). Devitillenized oocytes were recorded from 2-10 days post-injection using standard patch-clamp methods. For outside-out patches, glass patch pipettes (2-4 MΩ) were filled with a solution containing (in mM) 100 KCl, 10 HEPES, 0.1 $CaCl_2$, 0.5 $MgCl_2$, and 10 EGTA, while the bath contained 10 KCl, 90 NaCl, 10 HEPES, 0.1 $CaCl_2$, 0.5 $MgCl_2$, and 10 EGTA. For inside-out patches, patch pipettes and bath both contained 100 KCl, 10 HEPES, 0.1 $CaCl_2$, 0.5 $MgCl_2$, and 10 EGTA. The pH of all solutions was 7.1. Solid MAL-AZO-QA was dissolved as a concentrated stock solution in DMSO and stored at −20° C. until the day of use. Stocks were diluted into oocyte bath solution to final concentrations of 10 μM or 100 μM. The concentration of DMSO in the bath did not exceed 0.1%. Pulse protocols and measurements were performed with pCLAMP software, a DigiData 1200 series interface, and a PC-505 amplifier (Warner Instruments). Samples were taken at 10 kHz and the data was filtered at 1 kHz. Patches were held at −90 mV, pulsed to −100 mV for 60 msec to monitor leak, and pulsed to −20 mV for 30-100 msec at 1 Hz to elicit Shaker currents. The peak of the Shaker currents was measured to minimize the contribution of slow inactivation. Patches with a leak conductance >100 pS were not included in analysis.

Illumination of patches was achieved with a TILL Photonics Polychrome II monochrometer (Applied Scientific Instrumentation, Inc.) containing a 75 watt xenon short arc lamp with an output of 250-690 nm, a quartz fiber optic cable, and an epifluorescence condenser with an achromatic lens. Discrete wavelengths of light (+/−10 nm) were focused on patches through a quartz coverslip with a Fluor 20X, 0.5 NA objective lens (Nikon). Output intensity was measured for wavelengths between 300 and 600 nm. The measured output intensities for wavelengths between 340-600 nm ranged from 0.324e-8 to 6.23e-8 $W/cm^2$. Differences in light intensities at different wavelengths were taken into account when determining action spectra for channel block and unblock.
Recordings from Hippocamal Neurons
Primary dissociated hippocampal cultures were prepared from E18-19 Sprague-Dewey rat embryos and grown on glass cover slips in serum-containing media and incubated in 7% $CO_2$ in air at 37° C. Cells were co-transfected with GFP along with the modified Shaker channel described above with additional L366A and V454L mutations. Transfections with Lipofectamine 2000™ were performed at 12-14 DIV. About 10% of the cultured neurons appeared GFP-positive at 2-3 days after transfection. Coverslips containing the neurons were treated at 37° C. for 15 min with 300 μM MAL-AZO-QA in an extracellular recording solution containing (in mM) 135 NaCl, 5 KCl, 1.2 $MgCl_2$, 5 HEPES, 2.5 $CaCl_2$, and 10 glucose at pH 7.4. Patch pipettes (7-10 MΩ) were filled with 10 NaCl, 135 K-gluconate, 10 HEPES, 2 $MgCl_2$, 2 Mg-ATP, and 1 EGTA at pH 7.4. After washout of MAL-AZO-QA with extracellular solution, membrane potential was recorded at room temperature under whole-cell current clamp with an AXOPATCH 200A amplifier (Axon Instruments) and filtered at 10 kHz. Initial recordings were made at resting potential to evaluate the effects of light on spontaneous activity. In experiments where we wanted to quantify the effect of light on firing (e.g. FIG. 4b), cultures were treated with 6-cyano-7-nitroquinoxaline-2,3-dione (CNQX) (1 μM) and bicuculline (10 μM) to silence synaptic activity. Baseline currents were adjusted to set the membrane potential at −50 mV before depolarizing current steps ranging from 0.01-0.03 nA were applied to evoke action potentials. Cells were irradiated with a Lambda-LS illuminator containing a 125 watt xenon arc lamp (Sutter Instruments Company), equipped with narrow bandpass (+/− 10 nm) filters through a Fluor 20X, 0.5 NA objective lens (Nikon). Variability among data is expressed as mean+/− SEM, unless noted otherwise.
Results
As a starting point for engineering a light-activated channel, the Shaker $K^+$ channel was used because of the availability of structural and molecular information. Sigworth, F. *Quart. Rev. Biophys.* 27, 1-40 (1993); Laine, et al. *FEBS Lett.* 564, 257-263 (2004). Voltage-gated $K^+$ channels, including Shaker, are blocked by the binding of quaternary ammonium (QA) ions, such as tetraethylammonium (TEA), to a site in the pore-lining domain. MacKinnon & Yellen, *Science* 250, 276-279 (1990); Heginbotham, MacKinnon, *Neuron* 8, 483-491 (1992). Amino acid E422 is estimated to be 15-18 Å from the TEA binding site. Blaustein, et al. *Nature Struct. Biol.* 7, 309-311 (2000); Doyle, et al. *Science* 280, 69-77 (1998); Jiang, et al. *Nature* 423, 33-41 (2003). Tethering of a series of QA-containing compounds to position 422 shows that the degree of block is critically dependent on tether length, with a 5 Å difference in length making the difference between effective and ineffective block. Blaustein et al. (2000) supra. This information was used in designing and synthesizing a photoswitchable blocker that can be tethered onto the outside of modified Shaker channels. The molecule, MAL-AZO-QA, consists of a maleimide (MAL), for cysteine tethering; a QA group, to block the channel; and an AZO group in between (FIG. 1a). Previous studies show that the rigid AZO moiety shortens by ~7 Å when photoisomerized from the trans to the cis configuration. Knoll, H. Photoisomerism of Azobenzenes. in *CRC Handbook of Organic Photochemistry and Photobiology*, $2^{nd}$ ed. (eds. Horspool, W. & Lenci, F.) 89.1-89.16 (CRC Press, Boca Raton, Fla., 2004). It was reasoned that coupling MAL-AZO-QA to a cysteine introduced at residue 422 (mutant E422C) would block channels when the compound is in the long trans form, whereas photoconversion to the cis configuration would make the tether too short to permit block (FIG. 1b). Hence, the tethering of MAL-AZO-QA to Shaker should introduce a new extracellular gate that can be opened and closed with appropriate wavelengths of light.

FIGS. 1A and 1B Photoisomerization of MAL-AZO-QA gates ionic currents through modified Shaker channels. (1a) The rigid core of MAL-AZO-QA (between the a carbons flanking the AZO moiety) changes by ~7 Å upon photoisomerization. (1b) MAL-AZO-QA blocks ion flow in the trans configuration but is too short to block effectively after photoisomerization to the cis configuration. Diagram shows a model of the inner helices of the Shaker K$^+$ channel, derived from the crystal structure of the bacterial K$^+$ channel MthK[12], with the dimensions of MAL-AZO-QA drawn to scale.

The effects of MAL-AZO-QA were tested on Shaker channels expressed in *Xenopus* oocytes. To observe the time course of channel modification, MAL-AZO-QA was applied onto the extracellular surface of the channels in outside-out membrane patches. MAZ-AZO-QA application reduced the voltage-gated Shaker current by >60% over 4 min (FIG. 2a), but the limited survival time of excised patches made it difficult to assess the full magnitude of block. Channel block developed slowly and persisted after washout (FIG. 2b), consistent with covalent attachment to the channels. Subsequent exposure to ultraviolet light partly relieved channel block and exposure to visible light restored block. In contrast, light had no effect on channels in patches that had not been treated with MAL-AZO-QA.

Figure 2:
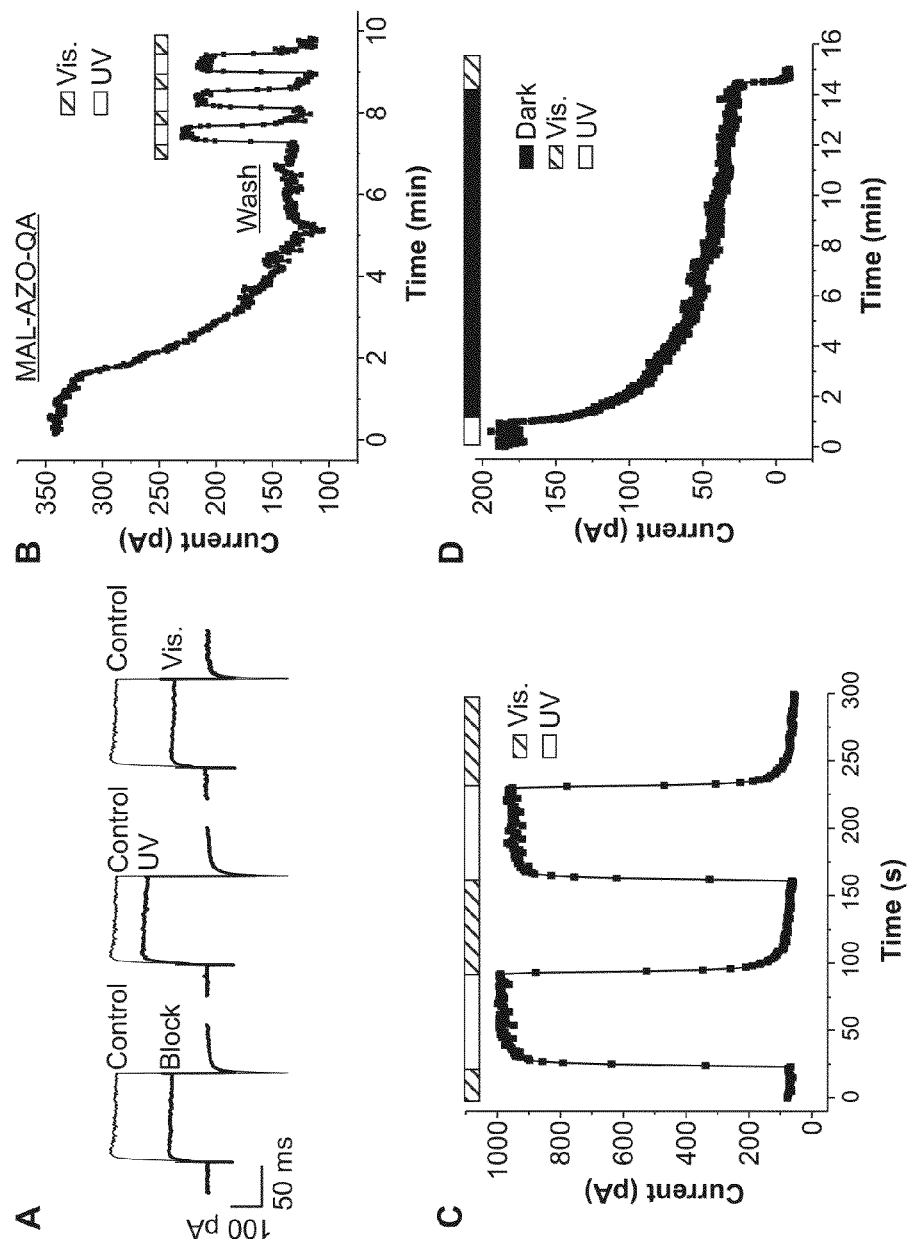
FIGS. 2A-D depict photocontrol of MAL-AZO-QA-modified Shaker channels in *Xenopus* oocytes.

To achieve more complete block of the channels, intact oocytes were treated with a higher concentration of MAL-AZO-QA for 30 min and then recorded from inside-out patches (FIG. 2c). In this situation, ultraviolet light unblocked as much as 1 nA of current, visible light re-blocked the channels almost completely, and both effects nearly reached steady-state within 5 sec under standard epifluorescence illumination. With steady ultraviolet illumination, the channels remained unblocked. However, in the dark unblocked channels slowly (>5 min) returned to the blocked state (FIG. 2D), consistent with thermal relaxation of the AZO moiety to the more stable trans configuration in the absence of light. Knoll, H. Photoisomerism of Azobenzenes. in *CRC Handbook of Organic Photochemistry and Photobiology*, 2$^{nd}$ ed. (eds. Horspool, W. & Lenci, F.) 89.1-89.16 (CRC Press, Boca Raton, Fla., 2004). Current block in the dark followed a bi-exponential time course, suggesting that a second process was involved. This may be a decrease in slow inactivation as the channels become re-blocked by QA. Choi, et al. *Proc. Natl. Acad. Sci. USA* 88, 5092-5095 (1991).

FIGS. 2A-D. Photocontrol of MAL-AZO-QA-modified Shaker channels in *Xenopus* oocytes. (a) Raw Shaker K$^+$ current traces recorded from an outside-out patch before and after treatment with MAL-AZO-QA. Scale bars: 100 pA (vertical) and 50 msec (horizontal). The top trace in each panel shows the current before MAL-AZO-QA application. Bottom traces represent current after 4 min application of 10 µM MAL-AZO-QA and 2 min washout (left panel), after 1 min exposure to ultraviolet (380 nm) light (middle panel), and after 1 min exposure to visible (500 nm) light (right panel). The patch was held at −90 mV and currents were elicited by 100 msec steps to −20 mV at 1 Hz. (b) K$^+$ current amplitudes from the same outside-out patch during perfusion with MAL-AZO-QA, during washout, and during alternating illumination with 380 and 500 nm light. (C) Inside-out patch from an oocyte treated with 100 µM MAL-AZO-QA for 30 min. The patch shows a large Shaker current in 380 nm light and almost complete block in 500 nm light. Pulse protocol same as above, except pulse duration was 30 msec. (D) Current block in dark follows a biexponential timecourse with $\tau_1$=0.49 min and $\tau_2$=4.79 min.

Figure 3:
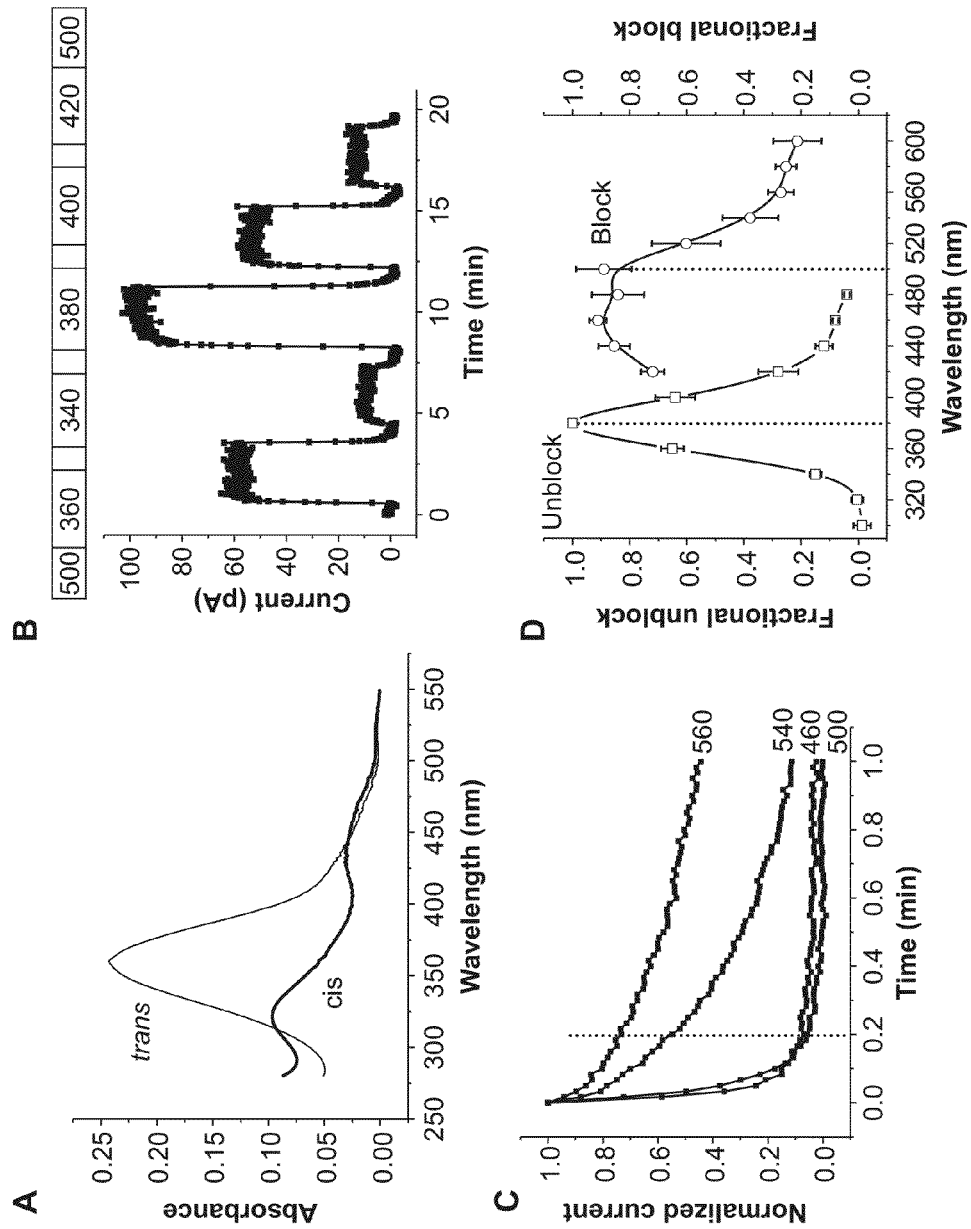
FIGS. 3A-D depict absorbance and action spectra of MAL-AZO-QA.

Which wavelengths are best for opening and closing MAL-AZO-QA-modified channels? To address this question, the absorbance spectra of MAL-AZO-QA was measured in solution as a glutathione adduct (FIG. 3a). The trans configuration of MAL-AZO-QA exhibits a large absorbance peak at 360 nm and small shoulder at ~440 nm, as reported previously for other AZO derivatives. Knoll, supra. Maximal photoisomerization to the cis configuration considerably decreased the 360 nm peak and slightly increased absorbance between 440 and 540 nm. Although the spectra indicate the wavelengths of maximum absorbance for the trans and cis isomers, the spectral overlap between isomers suggests that these may not be the optimal wavelengths for maximal photoconversion. In addition, coupling of MAL-AZO-QA to the channel protein could affect the absorbance spectra. The optimal wavelengths were determined empirically by measuring the action spectrum of each isomer (FIG. 3b-d).

To determine the wavelength that results in maximal recovery of K$^+$ currents, inside-out patches were initially exposed to long wavelength light (500 nm) from a Xenon lamp for at least 1 min to maximize occupancy of the blocked state. The patch was then irradiated with a discrete wavelength between 300-480 nm for 1 min, and the peak current at steady-state was measured to determine the degree of unblock (FIG. 3b). The resulting action spectrum shows that 380 nm is most effective in unblocking MAL-AZO-QA-modified Shaker channels (FIG. 3d. The action spectrum for channel unblock should reflect the steady-state ratio of trans and cis isomers (the photostationary state) at each wavelength.

To determine the complementary action spectrum for channel re-block, patches were exposed to 380 nm for 1 min to maximize occupancy of the cis state. Subsequent exposure to discrete wavelengths between 420 and 600 nm caused re-block of the channels at different rates (FIG. 3c). In this case, rate of re-block is the most relevant parameter, since many wavelengths will eventually result in complete block. Thus we measured the degree of block at a fixed time (0.2 min) for each wavelength. The broad peak of this action spectrum (FIG. 3d) suggests that wavelengths from 460 to 500 nm cause the fastest re-block of channels.

FIGS. 3A-D. Absorbance and action spectra of MAL-AZO-QA. (a) The UV/VIS spectrum of a MAL-AZO-QA-glutathione adduct (10 µM) in oocyte bath solution. To maximize the trans and cis isomers, the solution was exposed to visible and ultraviolet light, respectively, for 3 minutes. To generate the adduct, MAL-AZO-QA (1 M) was treated with reduced glutathione (1.5 M) in for 12 hrs at 21° C. (b) Unblock of Shaker channels at different wavelengths. Currents are from an inside-out patch alternately exposed to various wavelengths between 300-480 nm to unblock the channels, and 500 nm light to re-block the channels. (c) Re-block of Shaker channels at different wavelengths. The timecourse of block at various wavelengths of visible light. Each trial is preceded by 1 min irradiation at 380 nm to unblock the channels. Traces are superimposed for comparison. Normalized current amplitudes were measured at 0.2 min after onset of block. (D) Action spectra for unblock (left curve) and block (right curve) of Shaker K$^+$ channels (n=3-8 patches for each wavelength). Unblock (left axis): Current unblocked at each wavelength divided by current at 380 nm. Currents were compared within each patch. Block (right axis): Fraction of normalized current blocked at 0.2 min after illumination with visible light (n=2-7 patches for each wavelength).

It was determined whether light-activated channels could be used to control neuronal excitability. First, the voltage-dependence of the channel was modified, so that the photoswitch is the primary regulator of gating. Normally, Shaker K+ channels make only a minor contribution to the membrane conductance at typical resting potentials (−40 to −70 mV). The channels also display voltage-dependent inactivation, further limiting their contribution. Mutations were therefore introduced to eliminate rapid inactivation (46-46; Hoshi, et al. *Science* 250, 533-538 (1990)), reduce slow inactivation (T449V; Lopez-Barneo, et al. *Receptors Channels* 1, 61-71 (1993)), and shift voltage-dependent activation to hyperpolarized potentials (L366A; Lopez, et al. *Neuron* 7, 327-336 (1991)), as confirmed by expression in oocytes. Expression of voltage-gated K+ channels with these modifications should result in a high resting K+ conductance and silencing of spontaneous activity.

Figure 4:
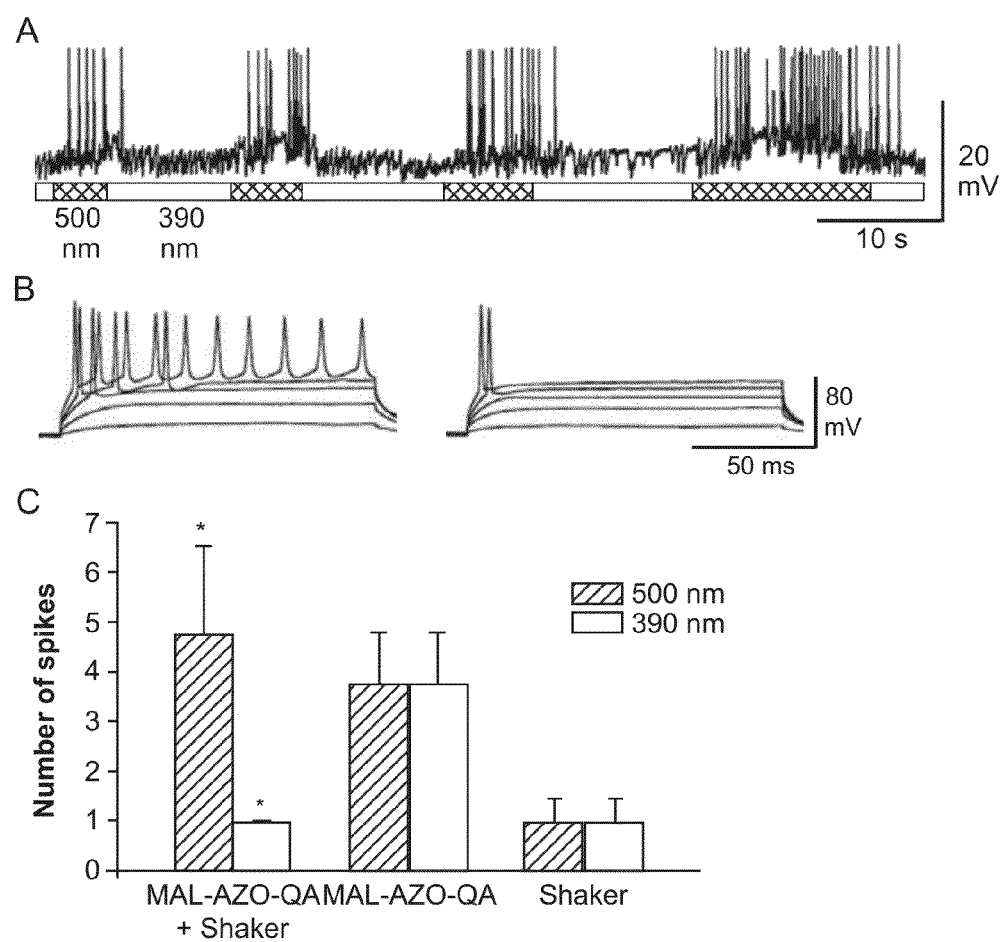
FIGS. 4A-C depict expression of light-activated channels confers light-sensitivity on hippocampal pyramidal neurons.

This multiply-mutated Shaker channel was expressed in cultured hippocampal neurons, which were subsequently treated with MAL-AZO-QA for 15 min in the dark, followed by thorough washout. Current clamp recordings from transfected pyramidal cells, identified by co-expression of GFP, showed that exposure to 390 nm light silenced spontaneous action potentials within 3 sec and exposure to 500 nm light restored activity also within seconds (FIG. 4a). Similar results were obtained in 5 cells. Activity could also be restored simply by leaving neurons in the dark after silencing, but the onset was slow (>30 sec), in accord with the slow re-block of ionic current observed in oocyte patches in the dark. Hence a 5 sec pulse of 390 nm light should produce relatively sustained silencing. Prolonged depolarizing current steps caused repetitive firing in 500 nm light (FIG. 4b, left). In contrast, in 390 nm light the same steps elicited rapidly accommodating responses (usually a single action potential, even with depolarization well above threshold) (FIG. 4b, right). On average, 390 nm light decreased the number of action potentials elicited by a depolarizing step by 79% (n=4) (FIG. 4c).

Light had no effect on MAL-AZO-QA-treated neurons that expressed GFP without the multiply-mutated Shaker channels (n=4), nor on channel-transfected neurons without MAL-AZO-QA treatment (n=5). Hence, it seems that native K+ channels are not susceptible to light-regulated block by tethered MAL-AZO-QA, even though many of these channels can be blocked by TEA. The observation that only Shaker-transfected neurons are light sensitive suggests that MAL-AZO-QA selectively attaches to the introduced cysteine, which is facilitated by the high effective local concentration of the cysteine-reactive maleimide when the quaternary ammonium binds to the pore. Blaustein, *J. Gen. Physiol.* 120, 203-216 (2002). Non-selective attachment of MAL-AZO-QA to extracellular cysteines on other membrane proteins may have no detectable effects on cellular electrophysiology, since other channels and receptors are unlikely to have a TEA-binding site positioned at the appropriate distance from a modifiable cysteine.

FIGS. 4A-C. Expression of light-activated channels confers light-sensitivity on hippocampal pyramidal neurons. (a) Spontaneous action potentials are silenced and revived by exposure to 390 and 500 nm light respectively. The neuron, transfected with the multiply-mutated Shaker channel, was treated for 15 min with MAL-AZO-QA before recording. The frequency of spontaneous synaptic potentials generated by untransfected neurons is not affected by light. (b) Depolarizing current steps elicit repetitive firing in 500 nm light (left) but only single action potentials in 390 nm light (right). Neurons were held under current clamp at ~−55 mV and depolarized up to ~−15 mV. (c) Summary of repetitive firing data. Number of spikes resulting from a suprathreshold depolarization to −15 mV is significantly modulated by light in the multiply mutated Shaker-transfected neurons treated with MAL-AZO-QA (*: $p<0.01$). Neurons expressing the channel without MAL-AZO-QA treatment, or treated with MAL-AZO-QA without channel expression, were unaffected by light.

Example 2

Light-Regulated Ionotropic Glutamate Receptor (iGluR)

The iGluR family members mediate the major excitatory currents in the central nervous system[8]. Structurally, they are tetrameric protein assemblies whose subunits consist of an extracellular N-terminal domain (NTD), an extracellular ligand binding domain (LBD), and a transmembrane domain (TMD) that forms the pore (FIG. 5b)[9]. The LBD closes like a clamshell as it binds the agonist glutamate. This reversible binding and closure is allosterically coupled, in an as yet unknown way, to the opening of the pore. The detailed structures of the LBD of several iGluR's in their apo state or in complex with agonists (e.g. glutamate, kainate, AMPA or domoic acid) have been solved by X-ray crystallography[10-12]. These structures provide a vivid picture of how the LBD closes when the agonist binds.

Figure 5A:
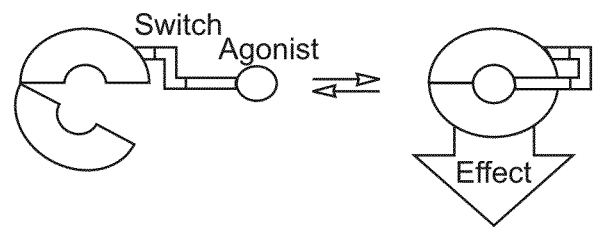
FIGS. 5A-C schematically depict a design of an allosteric photoswitch.
Figure 5B:
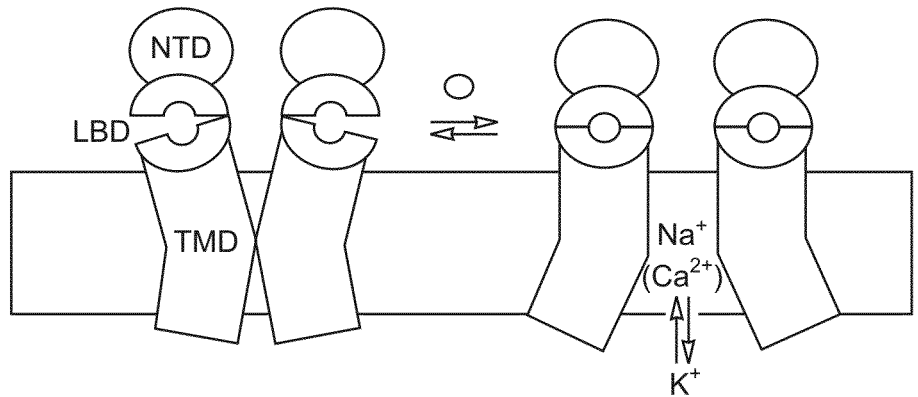
Figure 5C:
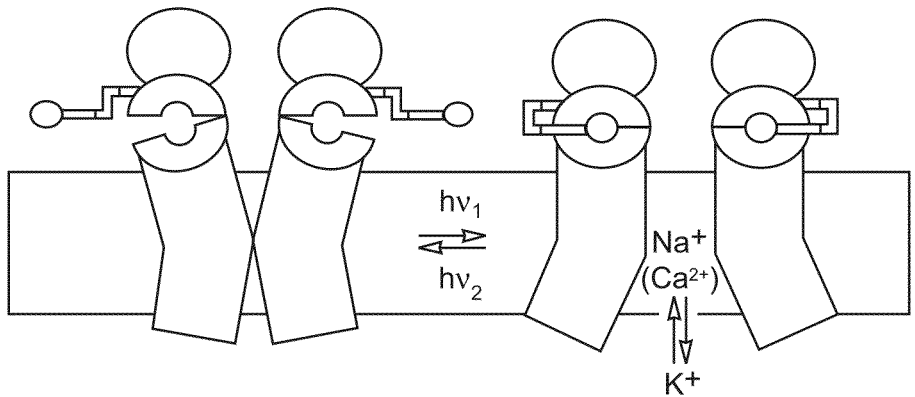

The approach to engineering LiGluR was to site-specifically attach a tethered analogue of glutamate containing a photoisomerizable azobenzene moiety to a "lip" of the LBD clamshell (FIG. 5c). In one state of the azobenzene, the LBD would not bind the tethered agonist and therefore remain open. Only after isomerization would the tether present the agonist to the binding site and thus effect closure. Overall, the reversible switching of an azobenzene would allosterically trigger the opening and closing of the entire ion channel, mediated by the clamshell-like movement of the LBD.

FIGS. 5A-C Design of an allosteric photoswitch. (a) An agonist (orange) is tethered to a LBD through an optical switch (red) via linkers (black). In one state of the switch, the ligand cannot reach the binding pocket, whereas in the other state the ligand docks and stabilizes the activated (closed) conformation of the LBD. (b) Schematic representation of the operating mode of iGluRs. Binding of an agonist (orange) stabilizes the activated (closed) conformation of the LBD and allosterically opens the pore, allowing flow of $Na^+$, $Ca^{2+}$ and NBD=N-terminal domain. TMD=transmembrane domain. (c) The principle of LiGluR. Reversible optical switching of a tethered agonist on the LBD opens and closes the pore.

Methods
Synthetic Protocols.
General Information

All non-aqueous reactions were performed using flame- or oven-dried glassware under an atmosphere of dry nitrogen. Commercial reagents were used as received. Non-aqueous reagents were transferred under nitrogen with a syringe or cannula. Solutions were concentrated in vacuo on a Buchi rotary evaporator. Diisopropylethylamine (DIPEA) was distilled from calcium hydride prior to use. Tetrahydrofuran (THF) and methylene chloride ($CH_2Cl_2$) were passed through a column of activated alumina under $N_2$-pressure prior to use. N,N-Dimethyl formamide (DMF) was degassed with a stream of $N_2$, dried over molecular sieves, and used without further purification. Chromatographic purification of products was accomplished using flash column chromatography on ICN 60 32-64 mesh silica gel 63 (normal phase) or Waters Preparative C18 125 Å 55-105 µm silica gel (reversed phase), as indicated. Thin layer chromatography (TLC) was performed on EM Reagents 0.25 mm silica gel 60-$F_{254}$ plates. Visualization of the developed chromatogram was performed using fluorescence quenching, $KMnO_4$, ceric ammonium molybdate (CAM), or iodine stains. IR spectra were measured with a Genesis FT-IR spectrometer by thin film or Avatar 370 FT-IR by attenuated total reflectance accessory. Optical rotations were measured using a Perkin-Elmer 241 Polarimeter at 25° C. and 589 nm. $^1H$ and $^{13}C$ NMR spectra were recorded in deuterated solvents on Bruker AVB-400, AVQ-400, or DRX-500 spectrometers and calibrated to the residual solvent peak. Multiplicities are abbreviated as follows: s=singlet, d=doublet, t=triplet, q=quartet, m=multiplet, app=apparent, br=broad.

added directly to solid Grubbs' $2^{nd}$ generation catalyst (43 mg, 0.025 mmol). The mixture was heated to reflux for 12 h. The reaction mixture was then concentrated and purified by normal phase chromatography (8.5:1.5 $CH_2Cl_2$:EtOAc with 1% AcOH) to yield S4 (317 mg, 92%) as a tan oil. Data for S4: $R_f$ 0.15 (5:4 hexanes:EtOAc with 1% AcOH); $[\alpha]_D$=−21.8 (c 1.0, in $CH_2Cl_2$); IR: 2981, 2937, 1788, 1742, 1717, 1653 $cm^{-1}$; $^1H$ NMR ($CDCl_3$, 400 MHz) δ 6.98 (m, 1H), 5.90 (d, 1H, J=15 Hz), 4.57 (d, 1H, J=9 Hz), 4.24 (q, 2H, J=7 Hz), 2.82 (m, 2H), 2.34 (m, 1H), 2.25 (m, 1H), 1.97 (m, 1H), 1.51 (s, 9H), 1.27 (t, 3H, J=7 Hz); $^{13}C$ NMR ($CDCl_3$, 100 MHz) δ 173.4, 171.0, 149.2, 147.2, 123.3, 83.8, 61.8, 57.0, 40.6, 32.8, 28.1, 27.8, 20.7, 14.1; LRMS (ESI) Calc for $C_{16}H_{22}NO_7$ (M-H)$^-$: 340.1. Found: 340.1.

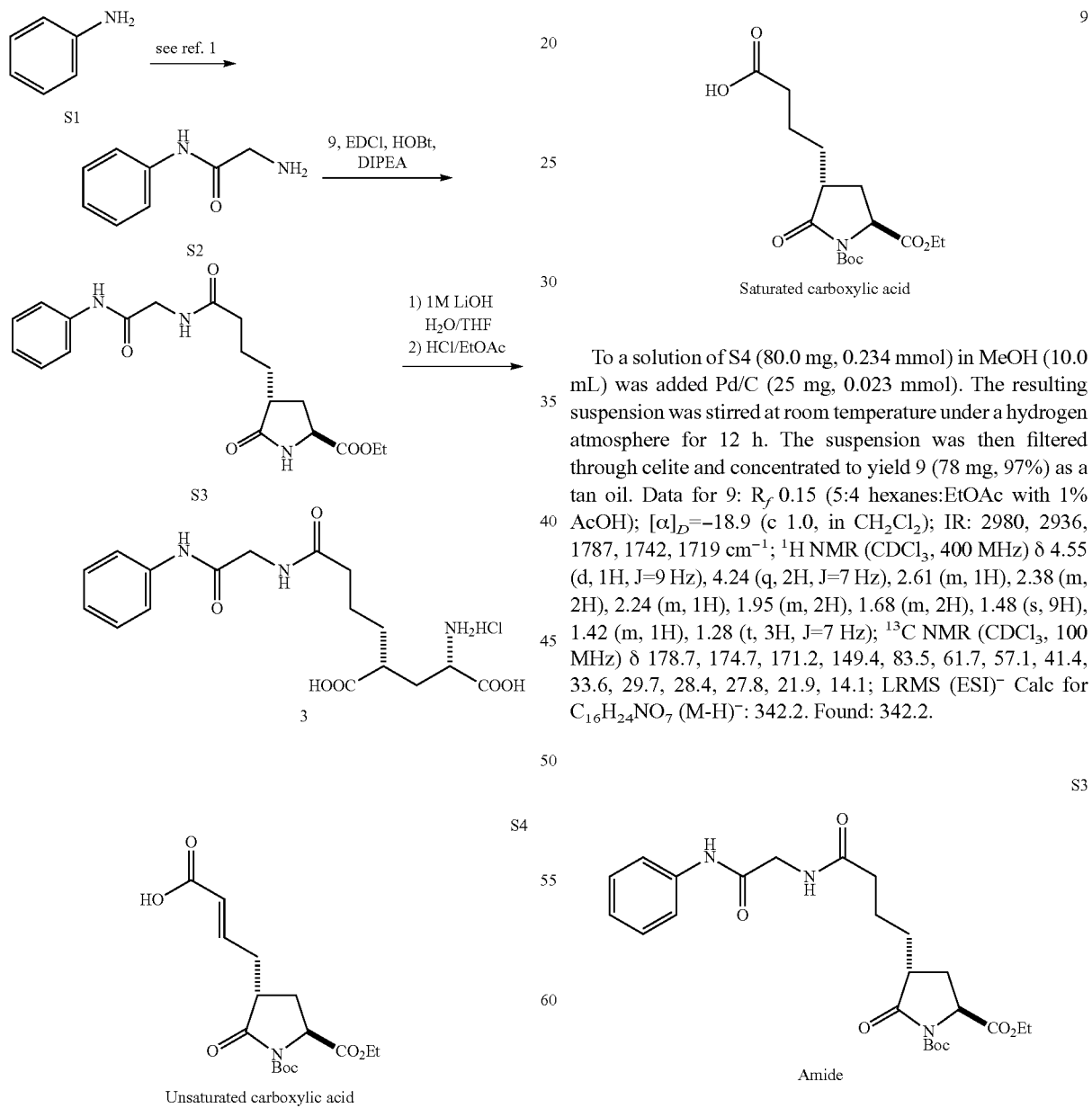

To a solution of S4 (80.0 mg, 0.234 mmol) in MeOH (10.0 mL) was added Pd/C (25 mg, 0.023 mmol). The resulting suspension was stirred at room temperature under a hydrogen atmosphere for 12 h. The suspension was then filtered through celite and concentrated to yield 9 (78 mg, 97%) as a tan oil. Data for 9: $R_f$ 0.15 (5:4 hexanes:EtOAc with 1% AcOH); $[\alpha]_D$=−18.9 (c 1.0, in $CH_2Cl_2$); IR: 2980, 2936, 1787, 1742, 1719 $cm^{-1}$; $^1H$ NMR ($CDCl_3$, 400 MHz) δ 4.55 (d, 1H, J=9 Hz), 4.24 (q, 2H, J=7 Hz), 2.61 (m, 1H), 2.38 (m, 2H), 2.24 (m, 1H), 1.95 (m, 2H), 1.68 (m, 2H), 1.48 (s, 9H), 1.42 (m, 1H), 1.28 (t, 3H, J=7 Hz); $^{13}C$ NMR ($CDCl_3$, 100 MHz) δ 178.7, 174.7, 171.2, 149.4, 83.5, 61.7, 57.1, 41.4, 33.6, 29.7, 28.4, 27.8, 21.9, 14.1; LRMS (ESI)$^-$ Calc for $C_{16}H_{24}NO_7$ (M-H)$^-$: 342.2. Found: 342.2.

A solution of 2 (321 mg, 1.07 mmol) and freshly distilled acrylic acid (231 mg, 3.21 mmol) in $CH_2Cl_2$ (5.0 mL) was To a solution of S2 (83.7 mg, 0.316 mmol), 1-Hydroxybenzotriazole hydrate (HOBt) (64.3 mg, 0.475 mmol), DIPEA (441 μL, 2.53 mmol), and N-Ethyl-N'-(3-dimethyl-diaminopropyl)-carbodiimide.HCl (EDCI) (79.0 mg, 0.412 mmol) in CH$_2$Cl$_2$ (12.0 mL) was added a solution of 9 (130 mg, 0.380 mmol) in CH$_2$Cl$_2$ (5.0 mL). The mixture was stirred at room temperature for 12 h. The mixture was diluted with CH$_2$Cl$_2$ (60 mL) and washed with a saturated NaHCO$_3$ solution (2×100 mL) and brine (2×100 mL). The organic layer was dried over Na$_2$SO$_4$, filtered, and concentrated. Purification by normal phase chromatography (95:5 CH$_2$Cl$_2$: MeOH) gave S3 (97 mg, 65%) as a white solid. Data for S3: R$_f$ 0.29 (95:5 CH$_2$Cl$_2$: MeOH); mp 57-59° C.; [α]$_D$=−14.4 (c 1.0, in CH$_2$Cl$_2$); IR: 3324, 2980, 2936, 2359, 2251, 1784, 1744, 1716, 1653, 1601, 1547 cm$^{-1}$; $^1$H NMR (CDCl$_3$, 500 MHz) δ 8.83 (s, 1H), 7.50 (d, 2H, J=8 Hz), 7.28 (t, 2H, J=8 Hz), 7.06 (t, 2H, J=7 Hz), 4.87 (d, 1H, 9 Hz), 4.20 (q, 2H, J=7 Hz), 4.08 (t, 2H, J=5 Hz), 2.59 (m, 1H), 2.31 (m, 2H), 2.18 (m, 1H), 1.89 (m, 2H), 1.70 (m, 2H), 1.44 (s, 9H), 1.39 (m, 1H), 1.26 (t, 3H, J=7 Hz); $^{13}$C NMR (CDCl$_3$, 125 MHz) δ 175.3, 173.7, 171.2, 167.5, 149.3, 137.8, 128.9, 124.3, 120.0, 83.7, 61.7, 57.2, 44.4, 41.4, 35.7, 29.7, 28.3, 27.8, 22.8, 14.2; HRMS (FAB) Calc for C$_{24}$H$_{33}$N$_3$O$_7$ (M)$^+$: 475.231851. Found: 475.23200.

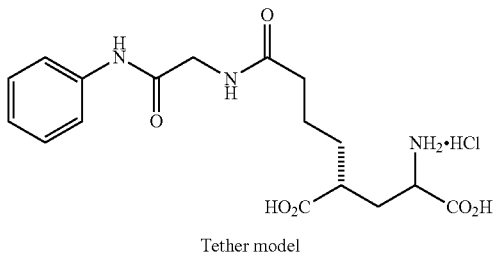

Tether model

To a solution of S3 (96.0 mg, 0.200 mmol) in THF (2.0 mL) was added a 1.0 M aqueous solution of LiOH (2.0 mL). The mixture was stirred at 0° C. for 1 h and then acidified to pH 2 with a 1.0 M HCl solution and extracted with EtOAc (3×20 mL). The combined organic layers were dried over Na$_2$SO$_4$, filtered, and concentrated to give an oily residue that was reacted with a saturated HCl solution in EtOAc for 2 h at room temperature. The resulting white solid was triturated with ethyl ether (3×20 mL) to yield 3 (68.5 mg, 85%). Data for 3: mp 154-156° C.; [α]$_D$=−11.4 (c 0.7, in H$_2$O); IR: 2933, 1709, 1598, 1544 cm$^{-1}$; $^1$H NMR (D$_2$O, 500 MHz) δ 7.30 (m, 4H), 7.13 (m, 1H), 3.92 (s, 2H), 3.87 (m, 1H), 2.58 (m, 1H), 2.26 (m, 2H), 2.21 (m, 1H), 1.85 (m, 1H), 1.55 (m, 4H); $^{13}$C NMR (DMSO-d$_6$, 125 MHz) δ 175.6, 172.4, 170.8, 167.9, 139.0, 128.7, 123.1, 119.1, 50.8, 42.7, 40.4, 35.0, 34.2, 31.2, 22.5; LRMS (ESI)$^-$ Calc for C$_{17}$H$_{22}$N$_3$O$_6$ (M-H)$^-$: 364.2. Found: 364.1.

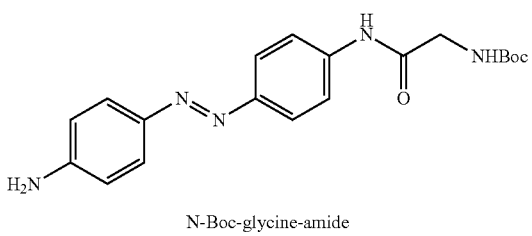

N-Boc-glycine-amide

To a solution of azodianiline 5 (750 mg, 3.50 mmol), HOBt (135 mg, 5.25 mmol), DIPEA (2.40 mL, 14.0 mmol), and EDCI (872 mg, 4.55 mmol) in CH$_2$Cl$_2$ (100 mL) was added a solution of Boc-Gly-OH (674.0 mg, 3.85 mmol) in CH$_2$Cl$_2$ (20 mL). The mixture was stirred at room temperature for 12 h. The mixture was diluted with CH$_2$Cl$_2$ (400 mL) and washed with a saturated NaHCO$_3$ solution (2×400 mL) and brine (2×400 mL). The organic layer was dried over Na$_2$SO$_4$, filtered, and concentrated. Purification by normal phase chromatography (dry loaded, 10:0→7:3 CH$_2$Cl$_2$:EtOAc) gave S5 (581 mg, 66%) as an orange solid. Data for S5: R$_f$ 0.21 (95:5 CH$_2$Cl$_2$: MeOH); mp 184-185° C.; UV λ$_{max}$ (MeOH): 391 nm; IR: 3306, 2424, 1705, 1673, 1602, 1531, 1501 cm$^{-1}$; $^1$H NMR (MeOH-d$_4$, 400 MHz) δ 7.75 (d, 2H, J=9 Hz), 7.68 (d, 4H, J=9 Hz), 6.72 (d, 2H, J=9 Hz), 3.88 (s, 2H), 1.46 (s, 9H); $^{13}$C NMR (DMSO-d$_6$, 125 MHz) δ 168.5, 156.0, 152.4, 148.0, 142.8, 140.2, 124.8, 122.5, 119.3, 113.4, 78.1, 43.9, 28.2; HRMS (FAB) Calc for C$_{19}$H$_{24}$N$_5$O$_3$ (MH)$^+$: 370.187915. Found: 370.187140.

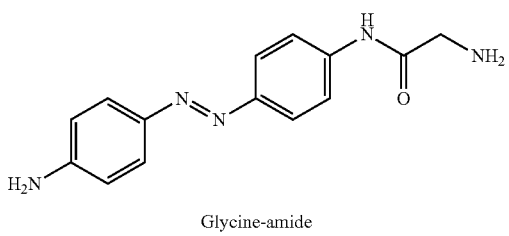

Glycine-amide

To a solution of S5 (565 mg, 1.53 mmol) in a 9:1 mixture of CH$_2$Cl$_2$:MeOH (50 mL) was added trifluoroacetic acid (50 mL). The mixture was stirred for 4 h at room temperature, concentrated, and triturated with diethyl ether (2×100 mL) to yield 6 (695 mg, 98%) as a purple solid. Data for 6: mp>180° C. dec; UV λ$_{max}$ (MeOH): 394 nm; IR: 2879, 2637, 1673, 1621, 1601, 1542, 1502 cm$^{-1}$; $^1$H NMR (MeOH-d$_4$, 400 MHz) δ 7.81 (d, 2H, J=9 Hz), 7.73 (m, 4H), 6.84 (d, 2H, J=9 Hz), 3.89 (s, 2H); $^{13}$C NMR (DMSO-d$_6$, 125 MHz) δ 165.6, 150.4, 149.5, 147.3, 140.9, 126.1, 124.1, 121.1, 117.5, 42.3; HRMS (FAB) Calc for C$_{14}$H$_{16}$N$_5$O (MH)$^+$: 270.135485. Found: 270.135930.

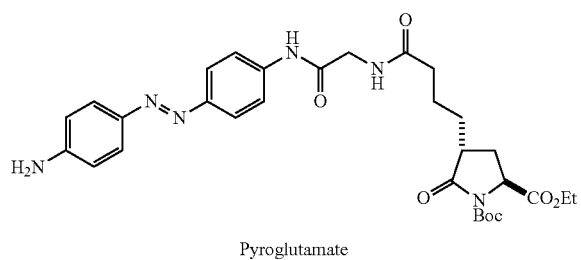

Pyroglutamate

To a solution of 6 (180 mg, 0.387 mmol), HOBt (78.6 mg, 0.581 mmol), DIPEA (269 μL, 1.55 mmol), and EDCI (96.4 mg, 0.503 mmol) in CH$_2$Cl$_2$ (20 mL) was added a solution of 9 (159 mg, 0.465 mmol) in CH$_2$Cl$_2$ (5.0 mL). The mixture was stirred at room temperature for 12 h. The mixture was diluted with CH$_2$Cl$_2$ (250 mL) and washed with a saturated NaHCO$_3$ solution (2×200 mL) and brine (2×200 mL). The organic layer was dried over Na$_2$SO$_4$, filtered, and concentrated. Purification by normal phase chromatography (97:3→95:5 CH$_2$Cl$_2$:MeOH) gave S6 (223 mg, 97%) as an orange solid. Data for S6: R$_f$ 0.32 (95:5 CH$_2$Cl$_2$: MeOH); mp 115-117° C.; [α]$_D$=−9.8 (c 1.0, in CH$_2$Cl$_2$); UV λ$_{max}$ (CHCl$_3$): 382 nm; IR: 3358, 2361, 1781, 1741, 1697, 1651, 1598, 1540 cm$^{-1}$; $^1$H NMR (CDCl$_3$, 400 MHz) δ 8.97 (s, 1H), 7.80 (d, 2H, J=9 Hz), 7.76 (d, 2H, J=9 Hz), 7.66 (d, 2H, J=9

Hz), 7.03 (m, 1H), 6.72 (d, 2H, J=9 Hz), 4.52 (dd, 1H, J=9 Hz), 4.21 (q, 2H, J=7 Hz), 4.12 (m, 2H), 4.07 (s-br, 2H), 2.67 (m, 1H), 2.33 (s, 2H), 2.26 (m, 1H), 1.94 (m, 2H), 1.74 (m, 3H), 1.46 (s, 9H), 1.27 (t, 3H, J=7 Hz); $^{13}$C NMR (CDCl$_3$, 100 MHz) δ 175.6, 173.7, 171.1, 167.6, 149.6, 149.2, 145.2, 139.3, 124.8, 123.1, 119.9, 114.5, 83.7, 61.7, 57.2, 44.3, 41.3, 35.6, 29.7, 28.1, 27.7, 22.7, 14.1; HRMS (FAB) Calc for C$_{30}$H$_{38}$N$_6$O$_7$ (M)$^+$: 594.280198. Found: 594.280490.

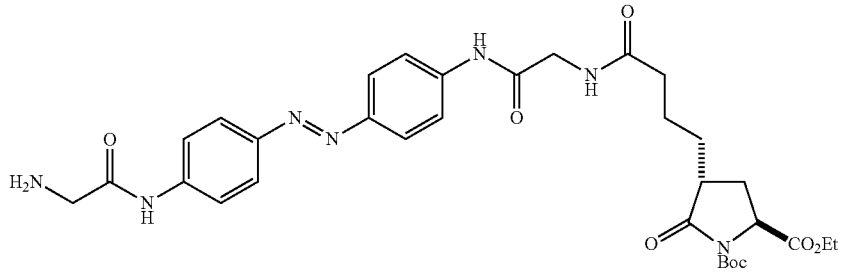

Amine

To a solution of Fmoc-Gly-OH (600 mg, 2.02 mmol) and oxalyl chloride (1.2 mL of 2.0 M solution in THF, 2.4 mmol) in CH$_2$Cl$_2$ (6.0 mL) was added one drop of DMF. After stirring for 1 h at room temperature the mixture was concentrated. The resulting acid chloride was redissolved in THF (11.0 mL) and added via cannula to a solution of S6 (400 mg, 0.672 mmol), DIPEA (586 µL, 3.36 mmol), and 4-(Dimethylamino)-pyridine (DMAP) (8.2 mg, 0.067 mmol) in THF (26.0 mL). After stirring 10 min at 0° C., the mixture was warmed to room temperature and stirred an additional 3 h. The mixture was then diluted with CH$_2$Cl$_2$ (150 mL) and washed with a saturated solution of NaHCO$_3$ (2×150 mL) and brine (2×150 mL). The organic layer was dried over Na$_2$SO$_4$, filtered, and concentrated. Purification by normal phase chromatography (90:10:0.6:0.6 CH$_2$Cl$_2$:MeOH:AcOH:H$_2$O) gave the Fmoc-glycine adduct as an orange solid that was sufficiently pure for further reaction. To a solution of this compound in DMF (20.0 mL) was added piperidine (200 µL, 2.02 mmol). After stirring for 6 h at room temperature, the mixture was concentrated and purified by reversed phase chromatography (4:1→2:3 0.1% formic acid in H$_2$O:MeCN) to yield 10 (186 mg, 43%) as an orange solid. Data for 10: mp>210° C. dec; [α]$_D$=−15.5 (c 0.3, in MeOH); UV λ$_{max}$ (MeOH): 365 nm; IR: 3280, 2981, 1781, 1690, 1593, 1546 cm$^{-1}$; $^1$H NMR (MeOH-d$_4$, 500 MHz) δ 7.88 (m, 4H), 7.76 (m, 4H), 4.63 (d, 1H, J=9 Hz), 4.24 (m, 2H), 4.03 (s, 2H), 3.85 (s, 2H), 2.64 (m, 1H), 2.34 (m, 2H), 2.28 (m, 1H), 2.08 (m, 1H), 1.89 (m, 1H), 1.72 (m, 2H), 1.47 (s, 9H), 1.42 (m, 1H), 1.29 (t, 3H, J=7 Hz); $^{13}$C NMR (MeOH-d$_4$, 100 MHz) δ 178.0, 176.5, 173.2, 170.1, 169.5, 151.0, 150.6, 150.3, 142.6, 141.9, 124.8, 124.7, 121.3, 121.1, 84.9, 63.0, 59.0, 45.9, 44.3, 42.8, 36.6, 31.1, 29.2, 28.3, 24.1, 14.7; HRMS (FAB) Calc for C$_{32}$H$_{41}$N$_7$O$_8$ (M)$^+$: 651.301662. Found: 651.304080.

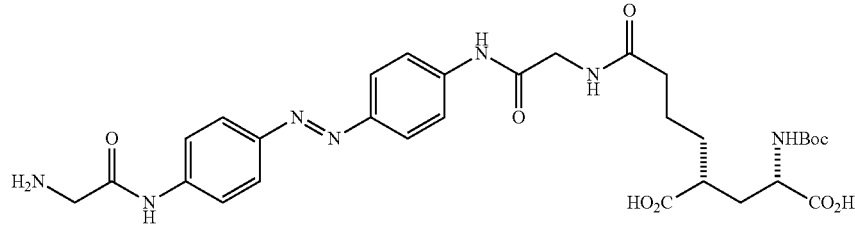

Amino acid

To a solution of 10 (180 mg, 0.276 mmol) in THF (10.0 mL) at 0° C. was added 1.0 M LiOH (10.0 mL). After stirring for 1 h, the mixture was acidified to pH 2 with 1 M HCl, THF was removed in vacuo, and the mixture was purified by reversed phase chromatography (5:0→4:1 0.1% formic acid in $H_2O$:MeCN) to yield S7 (143 mg, 80%) as a yellow solid. Data for S7: mp>230° C. dec; $[\alpha]_D$=−15.9 (c 0.1, in DMSO); UV $\lambda_{max}$ (DMSO): 379 nm; IR: 2981, 1690, 1660, 1595, 1546, 1500 cm$^{-1}$; $^1$H NMR (MeOH-$d_4$, 500 MHz) δ 7.87 (m, 4H), 7.76 (m, 4H), 4.07 (m, 1H), 4.03 (d, 2H, J=5 Hz), 3.88 (s, 2H), 2.55 (m, 1H), 2.32 (m, 2H), 2.20 (m, 1H), 1.70 (m, 4H), 1.59 (m, 1H), 1.42 (s, 9H); $^{13}$C NMR (DMSO-$d_6$, 125 MHz) δ 176.4, 174.2, 172.5, 168.5, 163.8, 155.4, 147.8, 147.6, 141.7, 141.2, 123.5, 123.4, 119.3, 79.2, 77.9, 52.5, 44.0, 42.9, 41.6, 35.0, 32.0, 28.2, 23.0; LRMS (ESI)$^-$ Calc for $C_{30}H_{38}N_7O_9$ (M-H)$^-$: 640.3. Found: 640.2.

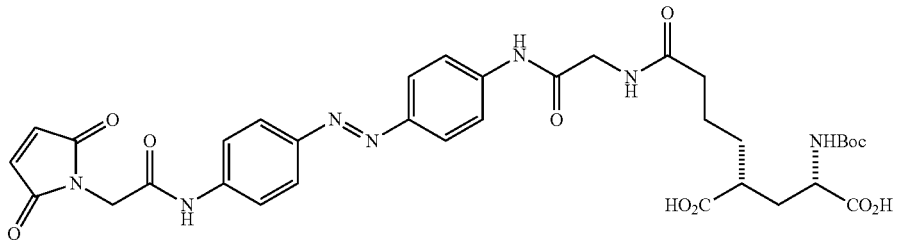

S8

Maleimide

To a solution of S7 (53 mg, 0.082 mmol) in a saturated solution of $NaHCO_3$ (3.5 mL) was added finely ground N-methoxycarbonylmaleimide (105 mg, 0.677 mmol) under vigorous stirring. After 30 min at 0° C., the mixture was diluted with THF (3.5 mL) and warmed to room temperature. After 1 h, the mixture was acidified to pH 1-2 with an aqueous solution of 1.0 M $H_2SO_4$ and extracted with EtOAc (2×20 mL). The combined organic layers were dried over $Na_2SO_4$, filtered, and concentrated. Purification by normal phase chromatography (90:10:0.6:0.6 $CH_2Cl_2$:MeOH:AcOH:$H_2O$) gave S8 (42 mg, 71%) as a yellow solid. Data for S8: $R_f$ 0.20 (90:10:0.6:0.6 $CH_2Cl_2$:MeOH:AcOH:$H_2O$); mp>230° C. dec; $[\alpha]_D$=−14.0 (c 0.1, in MeOH); UV $\lambda_{max}$ (MeOH): 365 nm; IR: 3249, 3186, 2928, 1753, 1708, 1687, 1651, 1520 cm$^{-1}$; $^1$H NMR (DMSO-$d_6$, 500 MHz) δ 10.61 (s, 1H), 10.31 (s, 1H), 8.19 (m, 1H), 7.84 (d, 4H, J=9 Hz), 7.79 (d, 2H, J=9 Hz), 7.75 (d, 2H, J=9 Hz), 7.16 (s, 2H), 7.10 (d, 2H, J=8 Hz), 4.32 (s, 2H), 3.82 (m, 1H), 3.64 (s, 2H), 2.35 (m, 1H), 2.15 (m, 2H), 1.93 (m, 1H), 1.59 (m, 1H), 1.49 (m, 3H), 1.42 (m, 1H), 1.36 (s, 9H); $^{13}$C NMR (DMSO-$d_6$, 125 MHz) δ 176.1, 174.2, 172.5, 170.7, 168.4, 166.6, 155.7, 147.9, 147.6, 141.7, 141.1, 135.0, 123.5, 123.4, 119.5, 119.3, 78.0, 52.4, 42.8, 41.4, 40.5, 45.0, 32.8, 32.1, 28.2, 22.9; LRMS (ESI)$^-$ Calc for $C_{34}H_{38}N_7O_{11}$ (M-H)$^-$: 720.3. Found: 720.3.

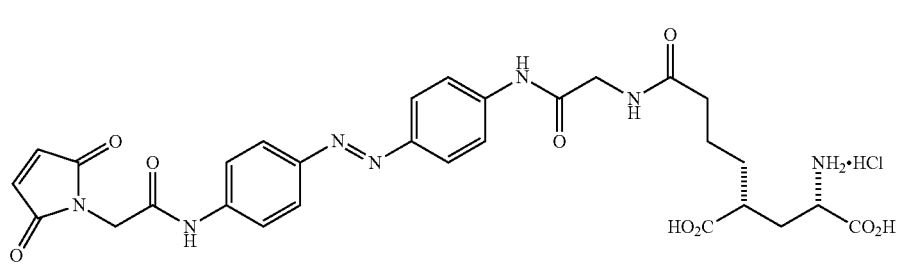

4

MAG

To a flask containing solid S8 (38 mg, 0.053 mmol) was added a saturated HCl solution in EtOAc (25.0 mL). After stirring at room temperature for 2 h, the resulting purple solid was triturated with ethyl ether (2×40 mL) to yield 4 (30 mg, 87%). Data for 4: mp>230° C. dec; =[α]$_D$19.5 (c 0.7, in DMSO); UV λ$_{max}$ (10% DMSO in H$_2$O): 363 nm; IR: 3279, 3052, 2935, 2362, 1922, 1709, 1598, 1538 cm$^{-1}$; $^1$H NMR (DMSO-d$_6$, 500 MHz) δ 10.70 (s, 1H), 10.39 (s, 1H), 8.23 (m, 1H), 7.84 (d, 4H, J=8 Hz), 7.79 (d, 2H, J=9 Hz), 7.76 (d, 2H, J=9 Hz), 7.16 (s, 2H), 4.32 (s, 2H), 3.91 (d, 2H, J=6 Hz), 3.81 (m, 1H), 2.89 (m, 1H), 2.16 (m, 2H), 2.13 (m, 1H), 2.77 (m, 1H), 1.53 (m, 4H); $^{13}$C NMR (DMSO-d$_6$, 125 MHz) δ 175.5, 172.4, 170.9, 170.7, 168.4, 165.3, 147.8, 147.6, 141.7, 141.1, 135.0, 123.5, 123.4, 119.4, 119.3, 64.9, 50.8, 42.7, 34.9, 31.7, 31.2, 22.4, 15.2; HRMS (ESI)$^+$ Calc for C$_{29}$H$_{32}$N$_7$O$_9$ (MH)$^+$: 622.2262. Found: 622.2268.

Site Directed Mutagenesis

Cysteine point mutations were introduced to the iGluR6 DNA, containing Q at the position 621 RNA editing site[15] using the QuikChange site-directed mutagenesis kit (Stratagene). The following PCR profile was used: one cycle (95° C. for 30 s); 20 cycles (95° C. for 30 s, 55° C. for 1 min, 68° C. for 12 min). The forward and reverse oligonucleotide sequences designed for the L439C mutant were:

```
                                       (SEQ ID NO: 1)
5'-GATTGTTACCACCATTTGCGAAGAACCGTATGTTCTG-3';
and (SEQ ID NO: 2)
5'-CAGAACATACGGTTCTTCGCAAAATGGTGGTAACAATC-3'.
```

Cell Culture and Transfection

HEK293 cells were plated at approximately 3×10$^6$ cells/ml on poly-1-lysine-coated glass coverslips (Deutsche Spiegelglas, Carolina Biological) and maintained in DMEM with 5% fetal bovine serum, 0.2 mg/ml streptomycin, and 200 U/ml penicillin at 37° C. Cells were transiently transfected with various plasmids using lipofectamine 2000 (Invitrogen). The amount of total transfected iGluR6 DNA and enhanced yellow fluorescent protein (EYFP) fusion DNA per well was fixed at 4 μg and 200 ng, respectively. All recordings were carried out 36 to 48 h after transfection.

Attachment of MAG

To conjugate MAG to cysteine mutants of iGluR6, the compound was diluted to 10-100 μM (final concentration 0.5-5% DMSO) in the HEK cell control solution and the cells were incubated in the dark for 15-30 min.

Calcium Imaging

Cells were washed in PBS and loaded with 5 μM FURA-2-AM (Molecular Probes) for 30 min. Changes of [Ca$^{2+}$], in individual cells were measured as intracellular Fura2 fluorescence intensity using mercury arc lamp illumination and alternating excitation with band pass filters of 350 nm and 380 nm during 66 ms at 5-20 s intervals and detecting emission at 510 nm[16]. Fluorescence was monitored on an inverted microscope system (Nikon). Images were captured with a CCD camera using the Imaging Workbench software, which was also used to irradiate the cells at 380 and 500 nm during 1-2 min in order to produce photoisomerization of MAG. Measurements were performed in a control solution (in mM): 135 NaCl, 5.4 KCl, 0.9 MgCl$_2$, 1.8 CaCl$_2$, HEPES, 10 glucose, and pH 7.6, containing 300 mg/l concanavalin A type IV (Sigma) to block desensitization[29,30]. L-Glutamate was applied as reported in text and figures. The results are representative data from multiple cells in at least two independent cultures.

Whole-Cell Patch Clamping

Patch clamp recordings were carried out using an Axopatch 200A amplifier in the whole cell mode. Cell voltage was held at −60 mV. Pipettes had resistances 4-8 MΩ and were filled with a solution containing (in mM): 145 CsCl, 5 EGTA, 0.5 CaCl$_2$, 1.0 MgCl$_2$, 10 HEPES, pH7.2. Illumination was applied using a TILL Photonics Polychrome II monochromator through a 60×/1.2 W objective (power output: 12.4 W/m$^2$ irradiance; 500 nm as measured with a Newport optical power meter). Data was recorded with pClamp software, which was also used to control the monochromator.

Results

The design of a tethered agonist was based on extensive structure-activity relationship analyses that have been performed on iGluR agonists[13,14] and, importantly, on the X-ray structure of the LBD of iGluR6 in complex with the agonist (2S,4R)-4-methyl glutamate (1) (FIG. 6c)[11]. From this structure, it can be seen that the ligand-bound form of the clamshell, although closed, features a narrow "exit channel." It was believed that the exit channel would enable a tether appended to an agonist to protrude and reach an attachment site at the surface of the protein, while still permitting the clamshell to close over the agonist and activate.

Figure 6A:
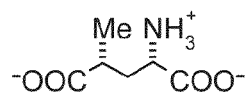
FIGS. 6A-D depict structures and fit of photoswitched agonist and iGluR6 LBD. (a) Chemical structure of the iGluR6 agonists (2S,4R)-4-methyl glutamate 1, (2S,4R)-4-allyl glutamate 2 and tether model 3.
Figure 6A:
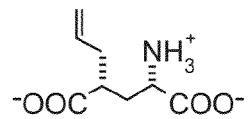
Figure 6A:
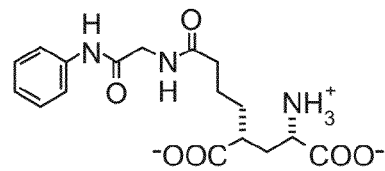

To explore the feasibility of this idea, a "tether model", termed MV-2-025 (3) (FIG. 6a), was synthesized. This compound is in essence an alkylated version of glutamate and resembles the known iGluR6 agonist (2S,4R)-4-allyl glutamate (2) (FIG. 6a)[14]. The allyl side chain of this compound was extended to include a moiety that mimics half of an azobenzene. This partial tether should, in principle, be long enough to project out of the exit channel and thus serve as a reasonable basis for determining if a full-length azobenzene tether would impede LBD activation.

FIGS. 6A-D. Structures and fit of photoswitched agonist and iGluR6 LBD. (a) Chemical structure of the iGluR6 agonists (2S,4R)-4-methyl glutamate 1, (2S,4R)-4-allyl glutamate 2 and tether model 3. (b) Structure of MAG 4 in its trans state (dark and 500 nm) and cis state (380 nm). (c) View looking into the "mouth" of iGluR6 LBD in complex with 1 (PDB ID 1SD3) (10). Residues on clamshell "lips" that were individually mutated to cysteine are highlighted in yellow. Position 439 is shown in red. The methyl group of 1 can be seen in blue at the bottom of the "exit channel." (d) Docking model of MAG in the cis state attached at L439C (yellow) and bound to the activated (closed) conformation of the LBD.

To assay LBD activation, the calcium permeability of iGluR6[15] was utilized. The iGluR6 was expressed in HEK293 cells, loaded the cells with the fluorescent calcium indicator FURA-2-AM[16], and the cells were exposed to various concentrations of agonist 2, or of the tether model 3, to quantify receptor activation (FIGS. 7A-E). Tether model 3 evoked large responses (FIG. 7b). Allyl glutamate 2 had an EC$_{50}$ of 18 μM, while model 3 showed an EC$_{50}$ of 180 μM (FIG. 7d). The maximal response of tether model 3 was similar to that evoked by saturating glutamate, but ~30% lower than that of the agonist 2 (FIG. 7d), indicating that the side chain may interfere with clamshell closure to a minor degree. These results suggest that tethering a glutamate analogue is possible while maintaining effective agonism. The loss in apparent affinity due to the side chain of model 3 should be compensated for by the high effective local concentration of a tethered ligand on its short leash.

FIGS. 7A-E Calcium imaging of iGluR6 activity. (a) Superimposed bright field (grey) and EYFP (green) images of HEK293 cells co-transfected with iGluR6 and EYFP. (b) Calcium image (350/380 nm) of FURA-2-AM loaded cells during perfusion of 300 μM glutamate. Red and blue corresponds to high and low $Ca^{2+}$ concentration, respectively. (c) Simultaneous $Ca^{2+}$ concentration traces from individual cells in response to indicated concentrations of the tether model 3. (d) Dose-response curves from $Ca^{2+}$ traces as in panel C. Higher concentrations of 3 activate iGluR6 at similar levels to saturating (1 mM) glutamate, to which responses are normalized. Tether model 3 has an EC50 of 180 μM, compared to the higher affinity molecule 2 on which it was based, which has an EC50 of 18 μM. (e) MAG 4 confers light sensitivity on iGluR6-L439C expressing cells (reversible increases in $Ca^{2+}$ at 380 nm and decreases at 500 nm) but not on wildtype iGluR6 (WT). Agonism by free MAG is transient and reverses upon washout for both iGluR6-L439C and WT. IGluR6-L439C retains ability to be activated by free glutamate after MAG 4 conjugation. Note that $Ca^{2+}$ concentration is not measured during irradiation at 380 or 500 nm, or during conjugation.

Figure 6B:
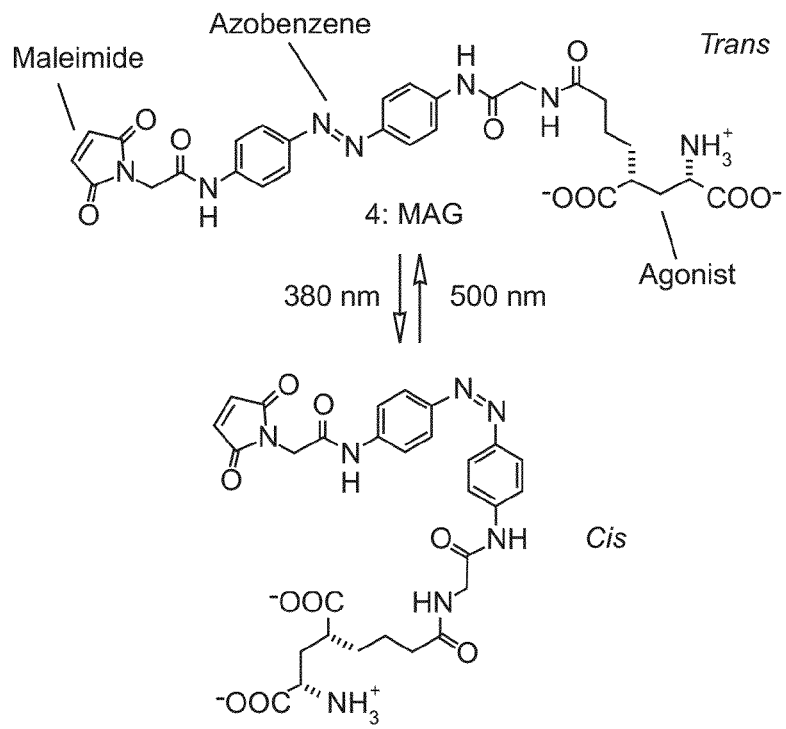
Figure 8:
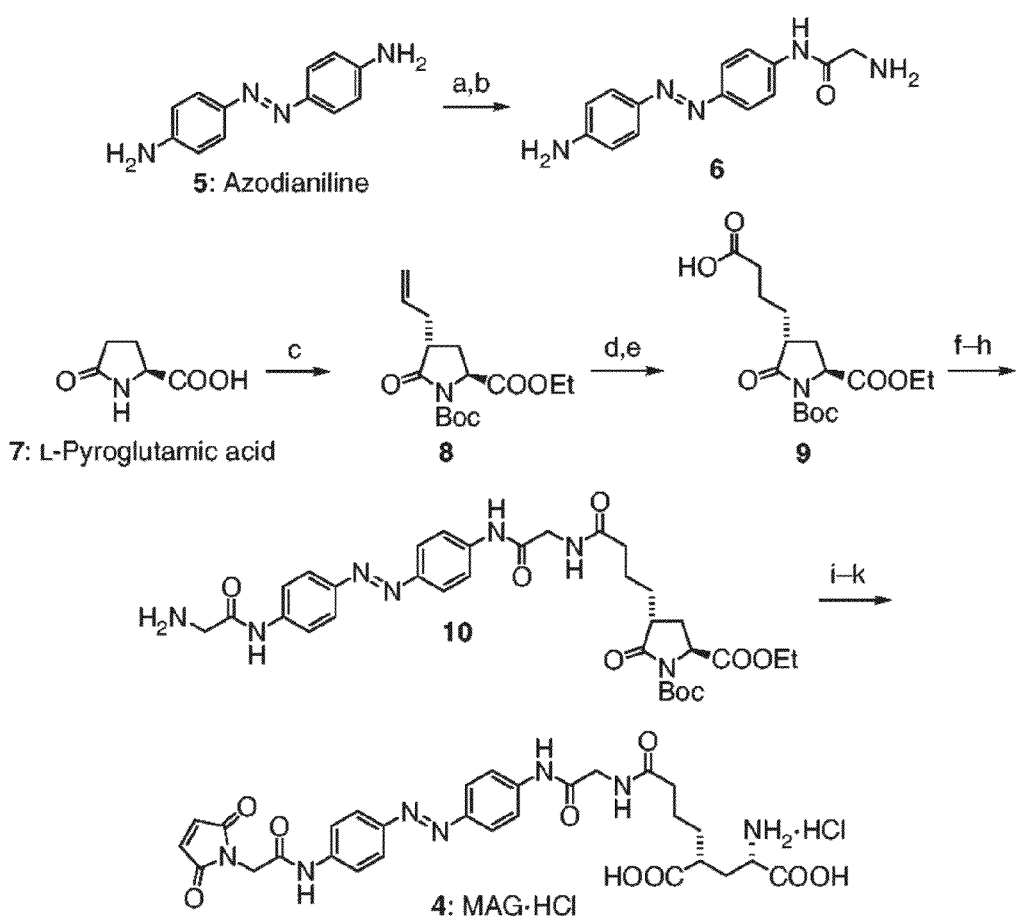
FIG. 8 depicts a scheme for total synthesis of MAG 4.

After evaluation of the stereochemistry and synthetic accessibility of several candidates, attention was focused on the tethered agonist compound designated MAG (4) (FIG. 6b). This compound features a cysteine reactive maleimide (M), an azobenzene photoswitch (A), and a glutamate headgroup (G). Since the iGluR X-ray structure, on which the design was based, only provides a snapshot of a flexible protein, a certain amount of conformational flexibility was also built into MAG 4 by adding to the linker freely rotatable bonds. The UV-VIS spectra of the cis- and trans-isomers of soluble MAG 4 are typical of azobenzenes. MAG 4 was prepared by multi-step synthesis, featuring a Grubbs olefin metathesis, several amide couplings and an intricate sequence of protective group manipulations as shown in Scheme 1, depicted in FIG. 8. The tether model 3 was prepared along similar lines.

Figure 6C:
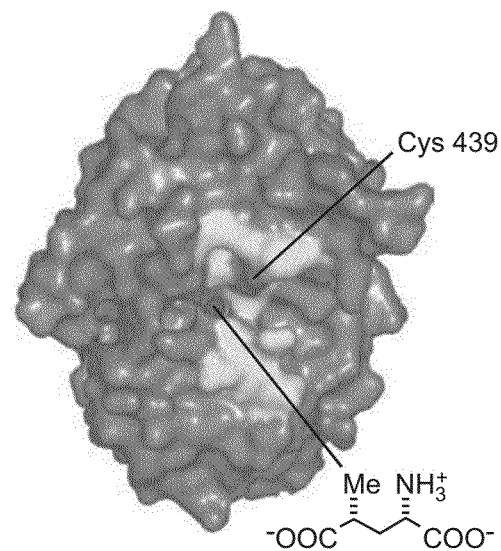

In parallel to the synthetic work described herein, a series of single cysteine mutants of iGluR6 was prepared by site-directed mutagenesis. The positions were chosen to form a perimeter around the exit channel, close to where the maleimide end of the tether was predicted to stick out (FIG. 6c). $Ca^{2+}$ imaging was used to search for cysteine mutants that would provide optical activation after covalent attachment of MAG 4. Although $Ca^{2+}$ imaging has slow kinetics and illumination at wavelengths that are absorbed by azobenzene, this assay enabled rapid testing of attachment positions. Three were found that demonstrated clear responses to light in which $Ca^{2+}$-concentration increased at 380 nm and declined back to basal levels at 500 nm. Of the three, the version of the receptor with a cysteine at 439 (iGluR-L439C) had the largest responses (FIG. 7e). Because the rise in free cytoplasmic $Ca^{2+}$ concentration depends not only on influx through iGluRs, but also on $Ca^{2+}$ buffering and pumping, we turned for further characterization to whole cell patch clamping to directly measure the kinetics of channel gating and to obtain quantitative measures of activation efficiency.

FIG. 8. Scheme 1

Total Synthesis of MAG 4. Reagents and conditions: (a) Boc-Gly-OH, EDC, HOBt, DIPEA (66%); (b) TFA, $CH_2Cl_2$ (98%); (c) see ref. 15; (d) Acrylic Acid, 5% Grubbs' $2^{II''}$ generation catalyst (92%); (e) $H_2$, Pd/C, MeOH (97%); (f) 6, EDCI, HOBt, DIPEA (97%); (g) Fmoc-Gly-OH, $(COCl)_2$, DMF; (h) Piperidine, DMF (43%, over two steps); (i) 1.0 M LiOH $H_2O$/THF, 0° C. (80%); (j) N-Methoxycarbonylmaleimide, $NaHCO_3$, $THF/H_2O$ (71%); (k) HCl sat'd EtOAc (87%). Boc, t-butoxycarbonyl; $CH_2Cl_2$, dichloromethane; $(COCl)_2$, oxalyl chloride; DIPEA, diisopropylethylamine; DMF, N,N-dimethylformamide; EDCI, N-ethyl-N'-(3-dimethyldiaminopropyl)-carbodiimide.HCl; EtOAc, ethyl acetate; Fmoc, 9-fluorenylmehoxycarbonyl; Gly, glycine; HOBt, 1-hydroxybenzotriazole hydrate; MeOH, methanol; Pd/C, palladium on carbon; TFA, trifluoroacetic acid; THF, tetrahydrofuran.

Figure 9A:
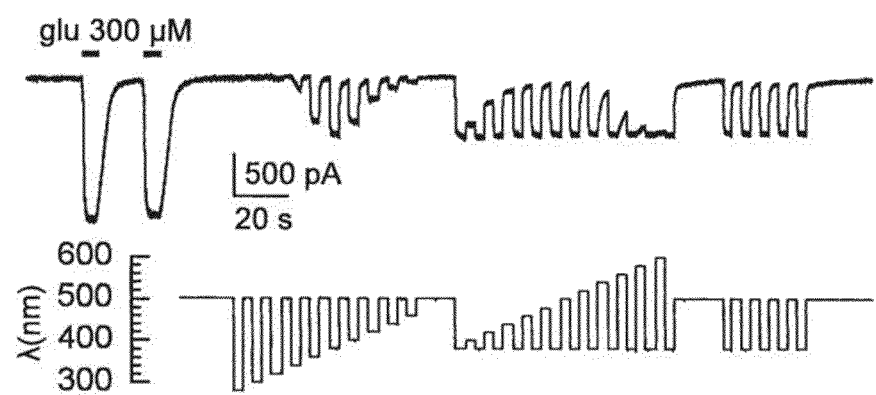
FIGS. 9A and 9B depict whole-cell patch-clamp current recordings from HEK293 cells expressing iGluR6-L439C after conjugation of MAG 4.
Figure 9B:
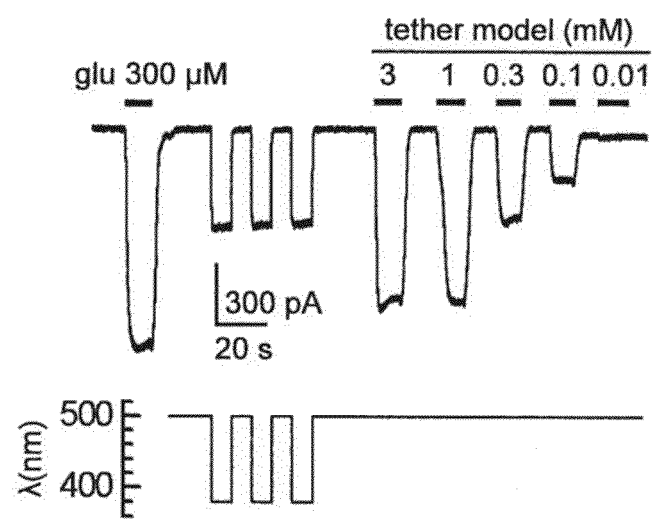

As shown in FIGS. 9A and 9B, iGluR-L439C conjugated with MAG 4 (LiGluR) can be activated both by free glutamate and by illumination. The photostationary cis/trans ratio of azobenzenes depends on the wavelength, with maximum cis-state occupancy typically observed at ~380 nm and maximum trans-state occupancy observed at ~500 nm[1,18]. The conjugate was illuminated at 500 nm (to favor the inactive trans form) and illumination at wavelengths that ranged from 280 to 460 nm (to photoisomerize to the active cis form) was tested. The shortest test wavelengths evoked no response, the intermediate wavelengths evoked substantial inward currents, and the longer wavelengths had smaller responses. The largest current was at 380 nm, agreeing with peak photoisomerization of free azobenzene to the cis form. To examine the opposite transition, the receptor was maximally activated with 380 nm illumination and tested wavelengths between 400 and 600 nm. Receptors were most efficiently turned off at 500 nm, agreeing with the peak photoisomerization of free azobenzene to the trans form.

Importantly, the photocurrents were fully reversible and highly reproducible. Repeated switching between 380 and 500 nm evoked responses of similar amplitude over a period of more than 30 minutes, consistent with the resistance of azobenzenes to bleaching and demonstrating that the system is robust. Even with weak illumination from a standard fluorescence lamp, attenuated by passage through a monochromator and fiber guide, the receptor turned on and off rapidly ($\tau_{on-380\ nm}$=115±3 ms and $\tau_{off-500\ nm}$=92.3±0.3 ms; mean±SEM, N=3) at a power of 12.4 $W/m^2$ (irradiance at 500 nm).

LiGluR can be turned on and off with light, but also preserves the ability to be activated by freely diffusible glutamate (FIGS. 9A, 9B). The currents generated by irradiation are smaller than currents evoked by saturating (300 μM) glutamate and by saturating (≥1 mM) tether model 3. This could be due to incomplete labeling, however, we consider that unlikely since increased exposure (in either concentration or time) to MAG 4 during the conjugation period did not change the size of the optical response. Alternatively, MAG 4 may only permit partial closure of the LBD. Incomplete closure of the ligand-binding domain has been previously linked to partial agonism in the related iGluR2 channel[19].

FIGS. 9A and 9B Whole-cell patch-clamp current recordings from HEK293 cells expressing iGluR6-L439C after conjugation of MAG 4. (a) Inward currents (downward deflections, carried mainly by $Na^+$ influx) in response to glutamate are preserved in LiGluR. Irradiation with short wavelengths of light (280 to 480 nm, in 20 nm increments) shows maximal activation at 380 nm. Irradiation with long wavelengths of light (400 to 600 nm, in 20 nm increments) shows maximal deactivation at 500 nm. Alternation between 380 and 500 nm illumination evokes highly reproducible responses. (b) Patch-clamp traces comparing responses of LiGluR to saturating glutamate, optical switching and the titration of the tether model 3. Saturating responses elicited by 3 are slightly higher than by 380 nm irradiation, suggesting geometric constraints that prevent the LBD from fully closing on MAG.

Figure 6D:
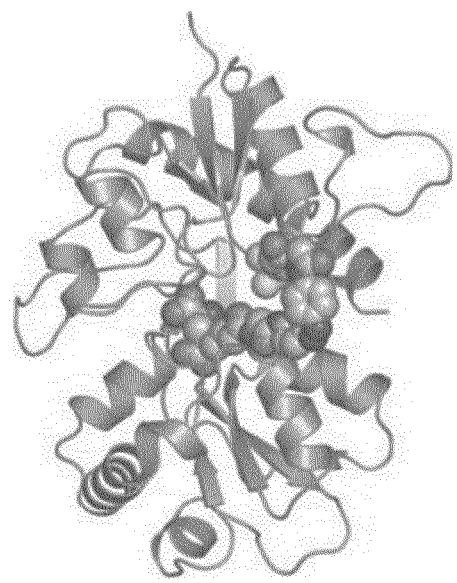

The efficient activation of iGluR6-L439C by MAG 4 can be explained by a model that shows cis-MAG docked into the glutamate-binding site of the closed (activated) conformation of the LBD (FIG. 6d). It is apparent that the linker between the glutamate head-group and the azobenzene moiety can comfortably protrude through the exit channel, with the azobenzene almost completely exposed to solvent.

REFERENCES

1. Feringa, B. L. Ed. *Molecular Switches*. (Wiley-VCH, Weinheim, Germany, 2001).
2. Goeldner, M. & Givens, R. *Dynamic Studies in Biology*. (Wiley-VCH, Weinheim, Germany, 2005).
3. Lester, H. A., Krouse, M. E., Nass, M. M., Wassermann, N. H. & Erlanger, B. F. Covalently bound photoisomerizable agonist—Comparison with reversibly bound agonists at electrophorus electroplaques. *J. Gen. Physiol.* 75, 207-232 (1980).
4. Kocer, A., Walko, M., Meijberg, W. & Fering a, B. L. A light-actuated nanovalve derived from a channel protein. *Science* 309, 755-758 (2005).
5. Banghart, M., Borges, K., Isacoff, E., Trauner, D. & Kramer, R. H. Light-activated ion channels for remote control of neuronal firing. *Nature Neurosci.* 7, 1381-1386 (2004).
6. Paas, Y. The macro- and microarchitectures of the ligand-binding domain of glutamate receptors. *Trends Neurosci.* 21, 117-125 (1998).
7. Dingledine, R., Borges, K., Bowie, D. & Traynelis, S. F. The glutamate receptor ion channels. *Pharmacol. Rev.* 51, 7-61 (1999).
8. Pin, J. P., Galvez, T. & Prezeau, L. Evolution, structure, and activation mechanism of family 3/C G-protein-coupled receptors. Pharmacol. *Ther.* 98, 325-354 (2003).
9. Kandel, E. R., Schwartz, J. H., & Jessell, T. M., Eds. *Principles of Neural Science*. (McGraw-Hill, New York, ed. 4, 2000).
10. Erreger, K., Chen, P. E., Wyllie, D. J. A., & Traynelis, S. F. Glutamate receptor gating. *Crit. Rev. Neurobiol.* 16, 187 (2004).
11. Armstrong, N. & Gouaux, E. Mechanisms for activation and antagonism of an AMPA-Sensitive glutamate receptor: Crystal structures of the GluR2 ligand binding core. *Neuron* 28, 165-181 (2000).
12. Mayer, M. L. Crystal structures of the GluR5 and GluR6 ligand binding cores: Molecular mechanisms underlying kainate receptor selectivity. *Neuron* 45, 539-552 (2005).
13. Nanao, M. H., Green, T., Stern-Bach, Y., Heinemann, S. F. & Choe, S. Structure of the kainate receptor subunit GluR6 agonist-binding domain complexed with domoic acid. *Proc. of the Natl. Acad. Sci. USA* 102, 1708-1713 (2005).
14. Johansen, T. N., Greenwood, J. R., Frydenvang, K., Madsen, U. & Krogsgaard-Larsen, P. Stereostructure-activity studies on agonists, at the AMPA and kainate subtypes of ionotropic glutamate receptors. *Chirality* 15, 167-179 (2003).
15. Pedregal, C. et al. 4-alkyl- and 4-cinnamylglutamic acid analogues are potent GluR5 kainate receptor agonists. *J. Med. Chem.* 43, 1958-1968 (2000).
16. Ezquerra, J. et al. Stereoselective Reactions of Lithium Enolates Derived from N-Boc Protected Pyroglutamic Esters. *Tetrahedron* 49, 8665-8678 (1993).
17. Kohler, M., Burnashev, N., Sakmann, B. & Seeburg, P. H. Determinants of $Ca^{2+}$ Permeability in Both Tm1 and Tm2 of High-Affinity Kainate Receptor Channels—Diversity by Rna Editing. *Neuron* 10, 491-500 (1993).
18. Grynkiewcz, G., Poenie, M. & Tsien, R. Y. A New Generation of $Ca^{2+}$ Indicators with Greatly Improved Fluorescence Properties. *J. Biol. Chem.* 260, 3440-3450 (1985).
19. Knoll, H. in CRC Handbook of Organic Photochemistry and Photobiology Horspool, W., & Lenci, F. Eds. 89, 1-89 (CRC Press, Boca Raton, Fla., 2004).
20. Jin, R. S., Banke, T. G., Mayer, M. L., Traynelis, S. F. & Gouaux, E. Structural basis for partial agonist action at ionotropic glutamate receptors. *Nature Neurosci.* 6, 803-810 (2003).
21. Kercher, M. A., Lu, P. & Lewis, M. Lac repressor operator complex. *Curr. Opin. Struct. Biol.* 7, 76-85 (1997).
22. Kunishima, N. et al. Structural basis of glutamate recognition by a dimeric metabotropic glutamate receptor. *Nature* 407, 971-977 (2000).
23. Furukawa, H. & Gouaux, E. Mechanisms of activation, inhibition and specificity: crystal structures of the NMDA receptor NR1 ligand-binding core. *EMBO J.* 22, 2873-2885 (2003).
24. Chen, X. et al. Structural identification of a bacterial quorum-sensing signal containing boron. *Nature* 415, 545-549 (2002).
25. Bayley, H. & Jayasinghe, L. Functional engineered channels and pores. *Mol. Membr. Biol.* 21, 209-220 (2004).
26. Dwyer, M. A. & Helling a, H. W. Periplasmic binding proteins: a versatile superfamily for protein engineering. *Curr. Opin. Struct. Biol.* 14, 495-504 (2004).
27. Willner, I. & Willner, B. Molecular and biomolecular optoelectronics. *Pure Appl. Chem.* 73, 535-542 (2001).
28. Balzani, A. C. V., & Venturi, M. *Molecular Devices and Machines: A Journey Into the Nanoworld* (Wiley-VCH, Weinheim, Germany, 2003).
29. Wilding, T. J. & Huettner, J. E. Activation and desensitization of hippocampal kainate receptors. *J. Neurosci.* 17, 2713-2721 (1997).
30. Partin, K. M., Patneau, D. K., Winters, C. A., Mayer, M. L. & Buonanno, A. Selective Modulation of Desensitization at AMPA Versus Kainate Receptors by Cyclothiazide and Concanavalin-A. *Neuron* 11, 1069-1082 (1993).

Example 3

Light-Controlled Ionotropic Glutamate Receptor; Affinity Labeling

The analysis of cell signaling requires the rapid and selective manipulation of protein function. Such control has been elusive because high ligand specificity usually derives from high affinity, yielding slow unbinding kinetics. Moreover, drug action is difficult to control spatially. Photoswitches were synthesized that covalently modify target proteins and reversibly present and withdraw a ligand from its binding site due to photoisomerization of an azobenzene linker. The properties of a glutamate photoswitch that controls an ion channel in cells are described here. Affinity labeling and geometric constraints ensure that the photoswitch controls only the targeted channel. Photoswitching to the activating state places a tethered glutamate at a high (millimolar) effective local concentration near the binding site. The fraction of active channels can be set in an analog manner by altering the photostationary state with different wavelengths. The bi-stable photoswitch can be turned on with millisecond long pulses at one wavelength, remain on in the dark for minutes, and turned off with millisecond long pulses at the other wavelength, yielding sustained activation with minimal irradiation. The system provides rapid, reversible remote control of protein function that is selective without orthogonal chemistry.

Methods

Synthesis of iGluR6 Tethered Agonist MAG-2.

MAG-2 was synthesized using chemistry similar to that previously described for MAG-1 (See Example 2 for synthesis of MAG-1.).

All non-aqueous reactions were performed using flame- or oven-dried glassware under an atmosphere of dry nitrogen. Commercial reagents were used as received. Non-aqueous reagents were transferred under nitrogen with a syringe or cannula. Solutions were concentrated in vacuo on a Buchi rotary evaporator. Diisopropylethylamine (DIPEA) was distilled from calcium hydride prior to use. Tetrahydrofuran (THF) and methylene chloride ($CH_2Cl_2$) were passed through a column of activated alumina under $N_2$-pressure prior to use. N,N-Dimethyl formamide (DMF) was degassed with a stream of $N_2$, dried over molecular sieves, and used without further purification. Chromatographic purification of products was accomplished using flash column chromatography on ICN 60 32-64 mesh silica gel 63 (normal phase) or Waters Preparative C18 125 Å 55-105 μm silica gel (reversed phase), as indicated. Thin layer chromatography (TLC) was performed on EM Reagents 0.25 mm silica gel 60-$F_{254}$ plates. Visualization of the developed chromatogram was performed using fluorescence quenching, $KMnO_4$, ceric ammonium molybdate (CAM), or iodine stains. IR spectra were measured with a Genesis FT-IR spectrometer by thin film or Avatar 370 FT-IR by attenuated total reflectance accessory. Optical rotations were measured using a Perkin-Elmer 241 Polarimeter at 25° C. and 589 nm. $^1H$ and $^{13}C$ NMR spectra were recorded in deuterated solvents on Bruker AVB-400, AVQ-400, or DRX-500 spectrometers and calibrated to the residual solvent peak. Multiplicities are abbreviated as follows: s=singlet, d=doublet, t=triplet, q=quartet, m=multiplet, app=apparent, br=broad.

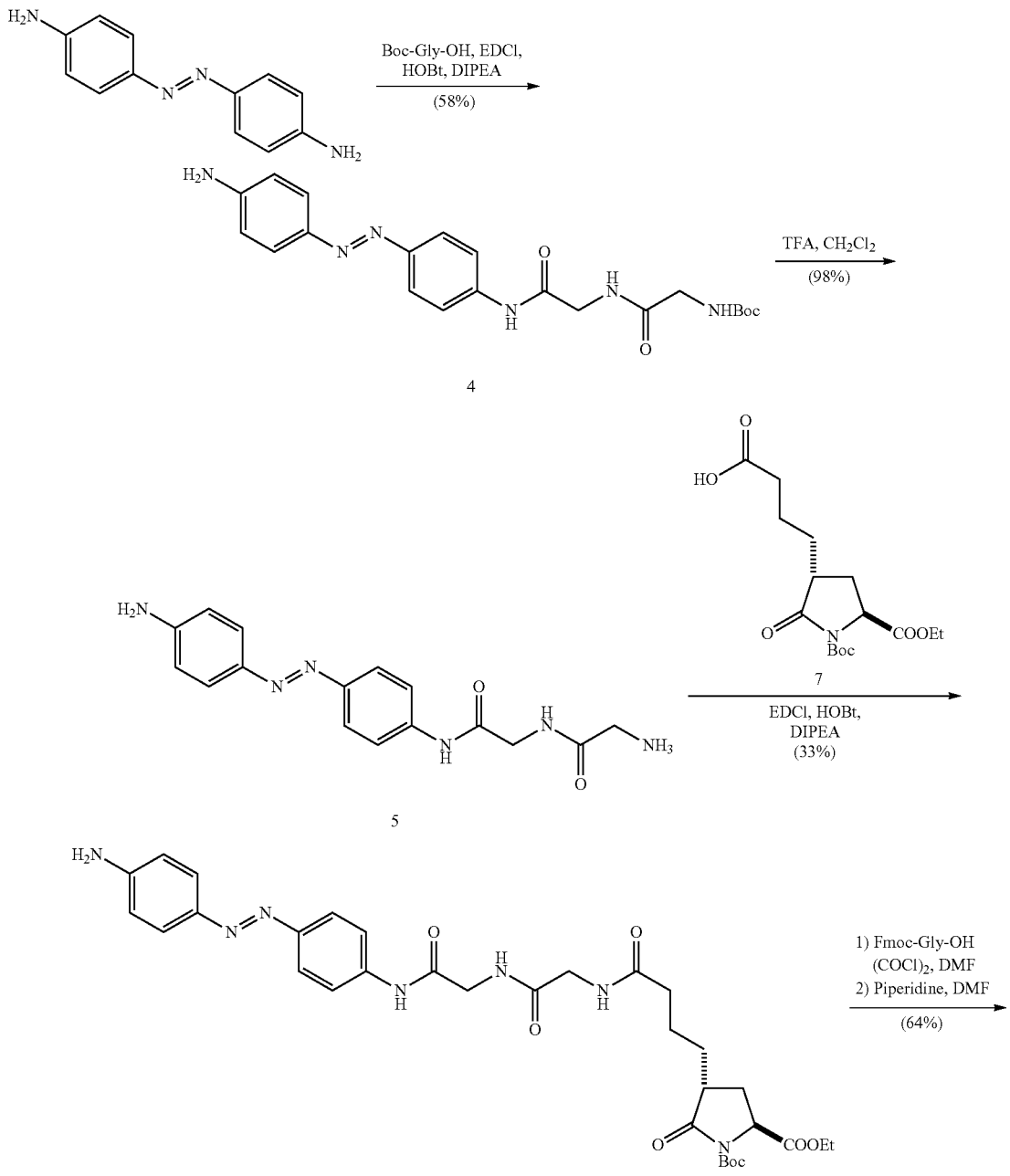

-continued
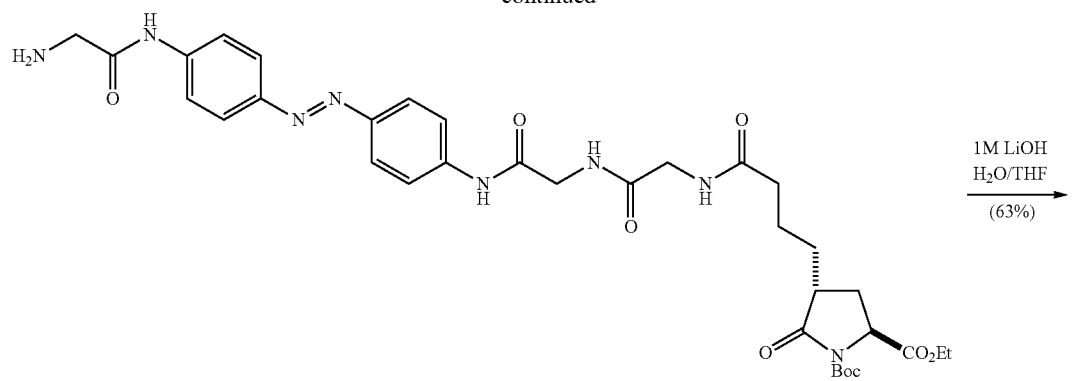
8
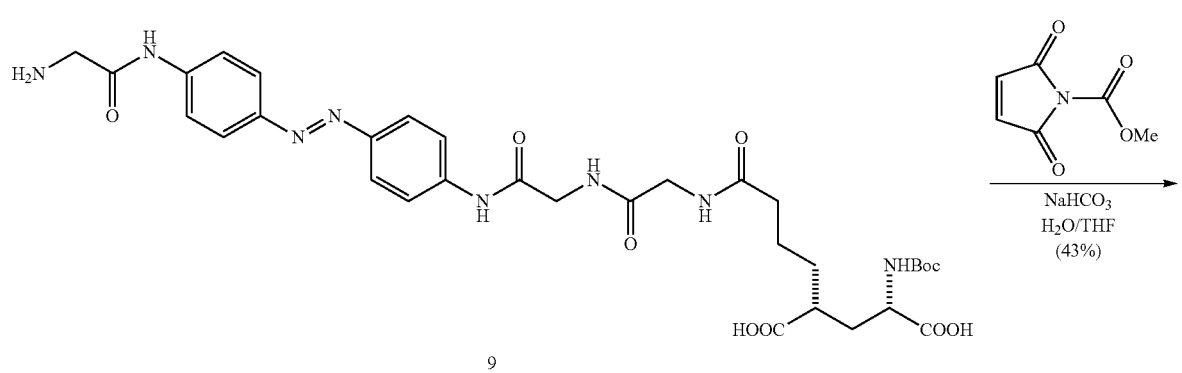
9
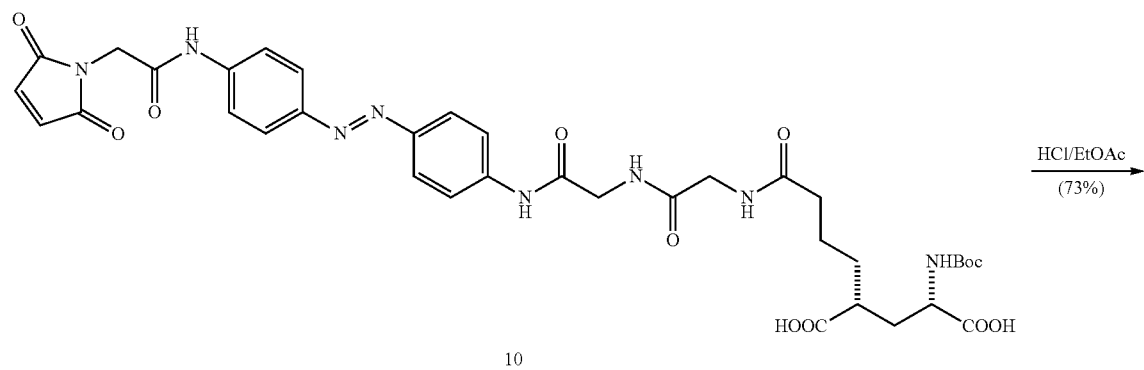
10
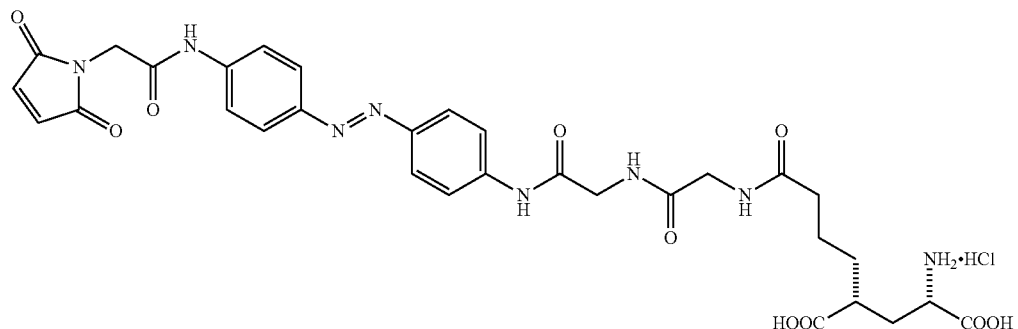
2

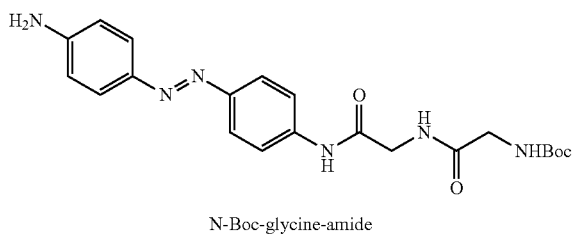

N-Boc-glycine-amide

To a solution of azodianiline (2.00 g, 9.4 mmol), 1-Hydrozy-benzotriazole hydrate (HOBt) (1.91 g, 14.1 mmol), Diisopropylamine (DIPEA) (6.54 mL, 37.6 mmol), and N-Ethyl-N'-(3-dimethyldiaminopropyl)-carhodiimide.HCl (EDCI) (2.34 g, 12.2 mmol) in $CH_2Cl_2$ (260 mL) was added a solution of Boc-Gly-Gly-OH (2.39 g, 10.3 mmol) in $CH_2Cl_2$ (50 mL). The mixture was stirred at room temperature for 12 h. The mixture was diluted with $CH_2Cl_2$ (500 mL) and washed with a saturated $NaHCO_3$ solution (2×500 mL) and brine (2×500 mL). The organic layer was dried over $Na_2SO_4$, filtered, and concentrated. Purification by normal phase chromatography (dry loaded, 10:0→20:1 $CH_2Cl_2$:MeOH) gave 4 (878 mg, 58% based on recovered azodianiline) as an orange solid. Data for 4: $R_f$ 0.28 (95:5 $CH_2Cl_2$:MeOH); mp 190-192° C.; UV $\lambda_{max}$ (MeOH): 394 nm; IR: 3397, 3365, 3273, 1712, 1703, 1651, 1598, 1613, 1550 cm$^{-1}$; $^1$H NMR (DMSO-$d_6$, 400 MHz) δ 10.09 (s, 1H), 8.20 (m, 1H), 7.72 (m, 4H), 7.61 (d, 2H, J=9 Hz), 7.08 (m, 1H), 6.65 (d, 2H, J=9 Hz), 6.02 (s, 2H), 3.92 (d, 2H, J=6 Hz), 3.60 (d, 2H, J=6 Hz), 1.38 (s, 9H); $^{13}$C NMR (DMSO-$d_6$, 125 MHz) δ 173.3, 169.7, 158.8, 153.3, 150.7, 145.7, 140.7, 126.0, 123.7, 121.4, 115.2, 81.0, 45.0, 44.0, 28.7; HRMS (FAB) Calc for $C_{21}H_{27}N_6O_4$ (M)$^+$: 427.209379 Found: 427.210320.

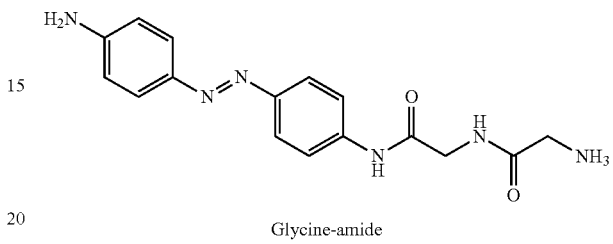

Glycine-amide

To a solution of 4 (1.00 g, 1.53 mmol) in a 5:1 mixture of $CH_2Cl_2$:MeOH (90 mL) was added trifluoroacetic acid (90 mL). The mixture was stirred for 4 h at room temperature, concentrated, and triturated with diethyl ether (2×100 mL) to yield 5 (1.01 g, 98%) as a purple solid. Data for 5: mp 174-175° C.; UV $\lambda_{max}$ (MeOH): 394 nm; IR: 3269, 3080, 1666, 1599, 1575, 1540, 1506 cm$^{-1}$; $^1$H NMR (MeOH-$d_4$, 500 MHz) δ 7.83 (m, 4H), 7.75 (d, 2H, J=9 Hz), 7.12 (d, 2H, J=7 Hz), 4.13 (s, 2H), 3.80 (s, 2H); $^{13}$C NMR (DMSO-$d_6$, 125 MHz) δ 169.4, 169.1, 149.7, 148.7, 141.8, 126.2, 124.1, 121.2, 119.7, 43.9, 41.5; HRMS (FAB) Calc for $C_{16}H_{19}N_6O_2$ (MH)$^+$: 327.156949. Found: 327.156620.

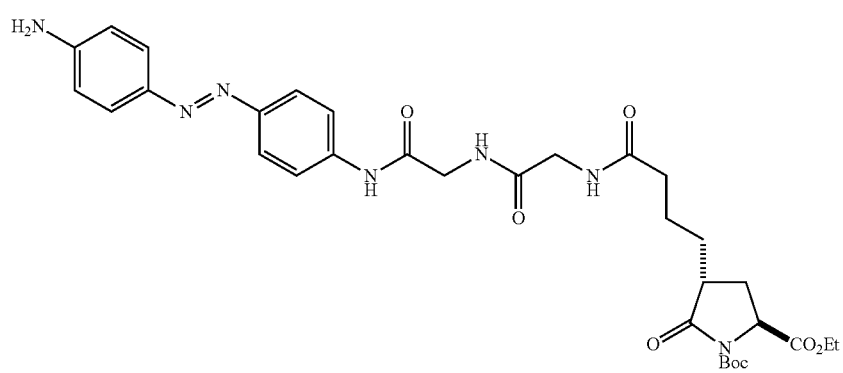

Pyroglutamate

To a solution of 5 (913 mg, 2.07 mmol), HOBt (421 mg, 3.11 mmol), DIPEA (1.44 mL, 8.29 mmol), and EDCI (517 mg, 2.69 mmol) in $CH_2Cl_2$ (100 mL) was added a solution of 7 (854 mg, 2.49 mmol) in $CH_2Cl_2$ (25 mL). The mixture was stirred at room temperature for 12 h. The mixture was diluted with $CH_2Cl_2$ (300 mL) and washed with a saturated $NaHCO_3$ solution (2×300 mL) and brine (2×300 mL). The organic layer was dried over $Na_2SO_4$, filtered, and concentrated. Purification by normal phase chromatography (95:5→90:10 $CH_2Cl_2$:MeOH) gave 6 (442 mg, 33%) as an orange solid. Data for 6: $R_f$ 0.29 (95:5 $CH_2Cl_2$: MeOH); mp 124-126° C.; $[\alpha]_D=-54.0$ (c 0.1, in MeOH); UV $\lambda_{max}$ (MeOH): 394 nm; IR: 3356, 2980, 2922, 2844, 1652, 1597, 1558 $cm^{-1}$; $^1H$ NMR (MeOH-$d_4$, 400 MHz) δ 7.76 (s, 4H), 7.69 (d, 2H, J=9 Hz), 6.73 (d, 2H, J=9 Hz), 4.55 (d, 1H, J=10 Hz), 4.19 (m, 2H), 4.05 (m, 2H), 3.89 (m, 2H), 2.60 (m, 1H), 2.33 (m, 2H), 2.19 (m, 1H), 2.00 (m, 1H), 1.85 (m, 1H), 1.70 (m, 2H), 1.44 (s, 9H), 1.40 (m, 1H), 1.24 (t, 3H, J=7 Hz); $^{13}C$ NMR (MeOH-$d_4$, 100 MHz) δ 178.0, 176.6, 173.1, 172.6, 169.8, 153.4, 150.8, 150.7, 145.7, 140.9, 126.2, 124.0, 121.5, 115.3, 84.8, 63.0, 58.8, 44.3, 42.7, 36.4, 30.9, 29.0, 28.2, 23.9, 14.7; HRMS (FAB) Calc for $C_{32}H_{40}N_7O_8$ $(MH)^+$: 651.301662. Found: 651.300110.

0.125 mmol), DIPEA (109 μL, 0.625 mmol), and 4-(Dimethylamino)-pyridine (DMAP) (1.5 mg, 0.013 mmol) in THF (7.0 mL). After stirring 10 min at 0° C., the mixture was warmed to room temperature and stirred an additional 3 h. The mixture was then diluted with $CH_2Cl_2$ (100 mL) and washed with a saturated solution of $NaHCO_3$ (2×100 mL) and brine (2×100 mL). The organic layer was dried over $Na_2SO_4$, filtered, and concentrated. Purification by normal phase chromatography (90:10:0.6:0.6 $CH_2Cl_2$:MeOH:AcOH:$H_2O$) gave the Fmoc-glycine adduct as an orange solid that was sufficiently pure for further reaction. To a solution of this compound in DMF (8.0 mL) was added piperidine (100 μL, 1.01 mmol). After stirring for 6 h at room temperature, the mixture was concentrated and purified by normal phase chromatography (90:10:0.6:0.6→80:20:3:3 $CH_2Cl_2$:MeOH: AcOH:$H_2O$) to yield 8 (56.8 mg, 64%) as an orange solid. Data for 8: mp>200° C. dec; $[\alpha]_D=-24.0$ (c 0.1, in DMSO); UV $\lambda_{max}$ (MeOH): 378 nm; IR: 3281, 2981, 1780, 1741, 1595, 1541 $cm^{-1}$; $^1H$ NMR (MeOH-$d_4$, 500 MHz) δ 7.85 (m, 6H), 7.77 (d, 2H, J=9 Hz), 4.56 (d, 1H, J=9 Hz), 4.20 (m, 2H), 4.06 (s, 2H), 3.90 (s, 2H), 3.84 (s, 2H), 2.60 (m, 1H), 2.33 (m, 2H), 2.20 (m, 1H), 2.02 (m, 1H), 1.76 (m, 1H), 1.71 (m, 2H),

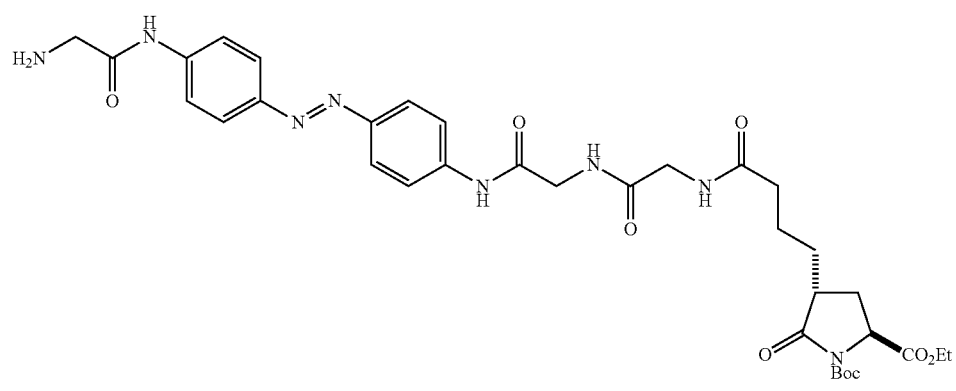

8

Amine

To a solution of Fmoc-Gly-OH (74.5 mg, 0.250 mmol) and oxalyl chloride (150 of 2.0 M solution in THF, 0.300 mmol) in $CH_2Cl_2$ (2.0 mL) was added one drop of DMF. After stirring for 1 h at room temperature the mixture was concentrated. The resulting acid chloride was redissolved in THF (3.0 mL) and added via cannula to a solution of 6 (81.7 mg, 1.44 (s, 9H), 1.43 (m, 1H), 1.25 (t, 3H, J=7 Hz); $^{13}C$ NMR (DMSO-$d_6$, 100 MHz) δ 174.7, 172.7, 172.5, 171.4, 169.7, 168.2, 148.8, 147.7, 147.6, 141.6, 141.5, 123.4, 123.3, 119.4, 119.2, 82.3, 61.2, 56.7, 45.6, 42.9, 42.3, 40.8, 34.9, 29.5, 27.5, 22.5, 22.3, 14.0; HRMS (FAB) Calc for $C_{34}H_{45}N_8O_9$ $(M)^+$: 709.330951. Found: 709.332180.

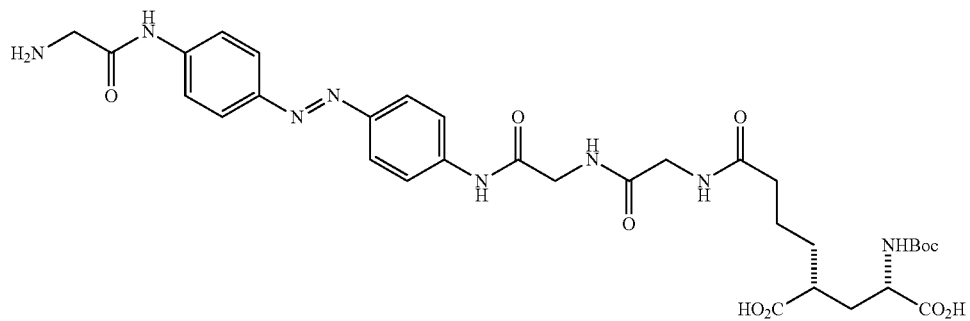

9

Amino acid

To a solution of 8 (152 mg, 0.214 mmol) in THF (8.0 mL) at 0° C. was added 1.0 M LiOH (8.0 mL). After stirring for 1 h, the mixture was acidified to pH 2 with 1 M HCl, THF was removed in vacuo, and the mixture was purified by reversed phase chromatography (5:0→4:1 0.1% formic acid in $H_2O$: MeCN) to yield 9 (95.1 mg, 63%) as a yellow solid. Data for 9: mp>230° C. dec; $[\alpha]_D$=−20.0 (c 0.1, in DMSO); UV $\lambda_{max}$ (DMSO): 378 nm; IR: 3285, 3070, 2933, 1666, 1598, 1538, 1501 cm$^{-1}$; $^1$H NMR (DMSO-$d_6$, 400 MHz) δ 10.21 (s, 1H), 8.37 (m, 1H), 8.22 (m, 2H), 7.84 (m, 8H), 7.55 (m, 1H), 6.88 (m, 1H), 6.81 (m, 1H), 3.92 (m, 2H), 3.76 (m, 1H), 3.72 (m, 2H), 3.55 (s, 2H), 2.35 (m, 1H), 2.14 (m, 2H), 1.91 (m, 1H), 1.58 (m, 1H), 1.48 (m, 4H), 1.35 (s, 9H); $^{13}$C NMR (DMSO-$d_6$, 100 MHz) δ 176.4, 174.2, 172.8, 169.7, 169.3, 168.2, 155.5, 147.8, 147.7, 141.6, 141.2, 123.5, 123.4, 119.4, 77.9, 52.5, 43.6, 42.9, 42.3, 41.6, 35.0, 33.3, 32.0, 28.2, 22.8; LRMS (ESI)$^-$ Calc for $C_{32}H_{41}N_8O_{10}$ (M-H)$^-$: 697.3. Found: 697.2.

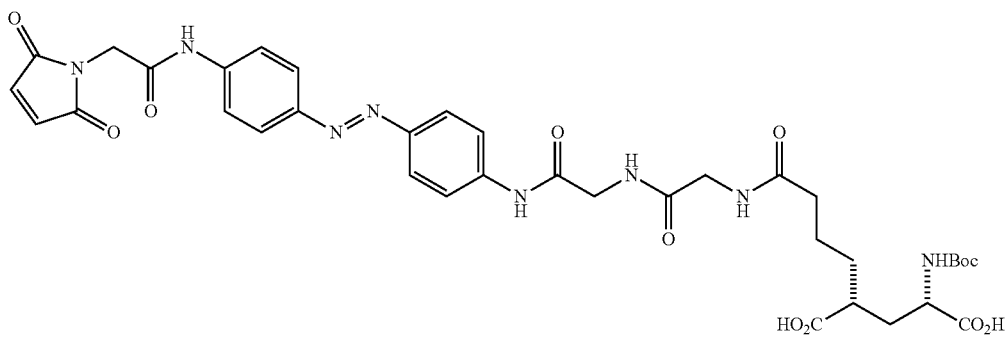

Maleimide

To a solution of 9 (36 mg, 0.052 mmol) in a saturated solution of NaHCO$_3$ (2.5 mL) was added finely ground N-methoxycarbonylmaleimide (36 mg, 0.232 mmol) under vigorous stirring. After 30 min at 0° C., the mixture was diluted with THF (2.5 mL) and warmed to room temperature. After 1 h, the mixture was acidified to pH 1-2 with an aqueous solution of 1.0 M $H_2SO_4$ and extracted with EtOAc (2×25 mL). The combined organic layers were dried over Na$_2$SO$_4$, filtered, and concentrated. Purification by normal phase chromatography (86:14:1.5:1.5 CH$_2$Cl$_2$:MeOH:AcOH:H$_2$O) gave 10 (17.1 mg, 43%) as a yellow solid. Data for 10: $R_f$ 0.27 (86:14:1.5:1.5 CH$_2$Cl$_2$:MeOH:AcOH:H$_2$O); mp>230° C. dec; $[\alpha]_D$=−17.0 (c 0.1, in MeOH); UV $\lambda_{max}$ (MeOH): 377 nm; IR: 3298, 3088, 2931, 1705, 1683, 1538 cm$^{-1}$; $^1$H NMR (DMSO-$d_6$, 400 MHz) δ 10.66 (s, 1H), 10.21 (s, 1H), 8.36 (t, 1H, J=6 Hz), 8.23 (t, 1H, J=6 Hz), 7.84 (m, 6H), 7.75 (d, 2H, J=9 Hz), 7.15 (s, 2H), 4.32 (s, 2H), 3.92 (d, 2H, J=4 Hz), 3.78 (m, 1H), 3.73 (d, 2H, J=5 Hz), 2.37 (m, 1H), 2.14 (m, 2H), 1.92 (m, 1H), 1.48 (m, 5H), 1.35 (s, 9H); $^{13}$C NMR 176.4, 174.3, 172.7, 170.7, 169.6, 168.2, 165.3, 155.5, 147.9, 147.7, 141.5, 141.0, 135.0, 123.5, 119.4, 119.3, 77.9, 52.5, 42.9, 42.2, 41.6, 40.5, 35.0, 33.3, 32.0, 28.2, 22.8; LRMS (ESI)$^-$ Calc for $C_{36}H_{41}N_8O_{12}$ (M-H)$^-$: 777.3. Found: 777.2.

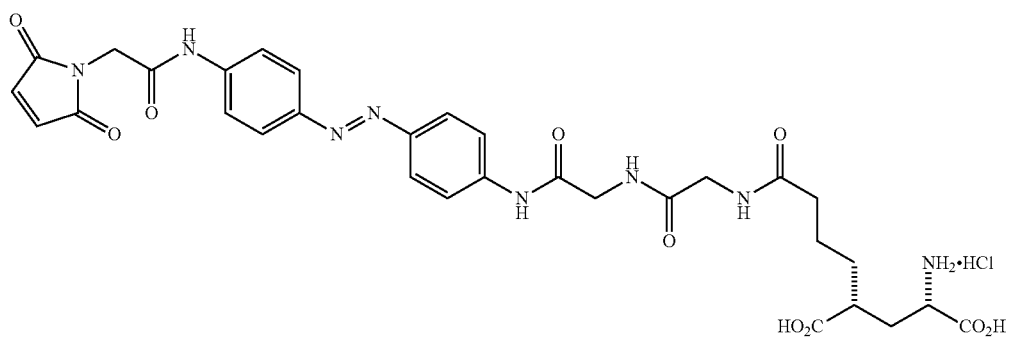

MAG

To a flask containing solid 10 (29 mg, 0.038 mmol) was added a saturated HCl solution in EtOAc (17.0 mL). After stirring at room temperature for 2 h, the resulting purple solid was triturated with ethyl ether (2×60 mL) to yield 2 (19.7 mg, 73%). Data for 2: mp>230° C. dec; $[\alpha]_D=-12.0$ (c 0.1, in DMSO); UV $\lambda_{max}$ (10% DMSO in $H_2O$): 364 nm; IR: 3298, 3087, 2930, 1706, 1683, 1652, 1539 cm$^{-1}$; $^1$H NMR (DMSO-d$_6$, 500 MHz) δ 10.70 (s, 1H), 10.25 (s, 1H), 8.28 (m, 4H), 8.21 (m, 1H), 7.84 (m, 6H), 7.76 (d, 2H, J=9 Hz), 7.16 (s, 2H), 4.32 (s, 2H), 3.93 (d, 2H, J=6 Hz), 3.79 (m, 1H), 3.74 (d, 2H, J=6 Hz), 2.57 (m, 1H), 2.17 (m, 2H), 2.12 (m, 1H), 1.75 (m, 1H), 1.52 (m, 4H); $^{13}$C NMR (DMSO-d$_6$, 125 MHz) δ 175.6, 172.5, 170.9, 170.7, 169.9, 168.2, 165.4, 147.8, 147.7, 141.6, 141.1, 135.0, 123.5, 119.4, 119.3, 64.9, 50.8, 42.8, 42.1, 34.9, 31.7, 31.2, 22.3, 15.2; HRMS (ESI)$^+$ Calc for $C_{31}H_{34}N_8O_{10}$ (M)$^+$: 678.23979. Found: 678.23954.

using the QuickChange site-directed mutagenesis kit (Stratagene). The following PCR profile was used: one cycle (95° C. for 30 s); 20 cycles (95° C. for 30 s, 55° C. for 1 min, 68° C. for 12 min). The forward and reverse oligonucleotide sequences designed for the L439C mutant were

```
                                    (SEQ ID NO: 1)
5'-GATTGTTACCACCATTTGCGAAGAACCGTATGTTCTG-3';
and
                                    (SEQ ID NO: 2)
5'-CAGAACATACGGTTCTTCGCAAAATGGTGGTAACAATC-3'.
```

Cell Culture and Transfection

HEK293 cells were plated at approximately $3 \times 10^6$ cells/ml on poly-L-lysine-coated glass coverslips (Deutsche Spiegelglas, Carolina Biological) and maintained in DMEM with 5%

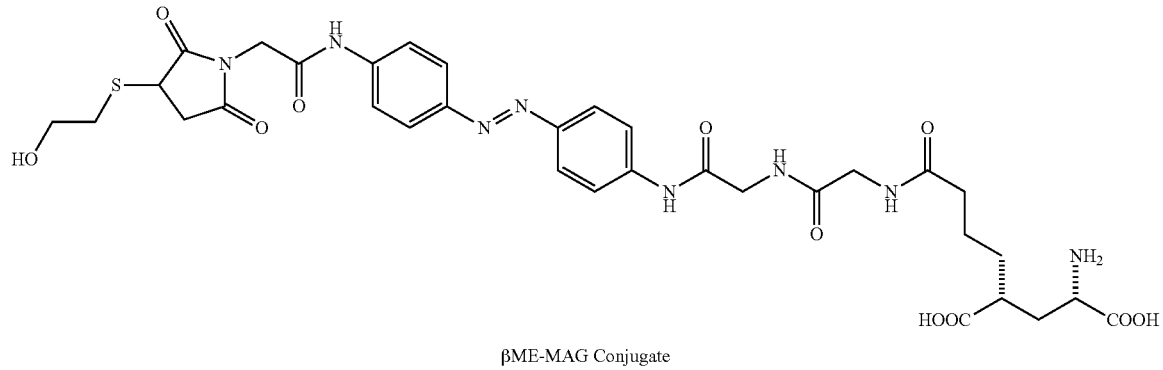

βME-MAG Conjugate

To a solution of 2 (2.3 mg, 3.5 mmol) dissolved in a saturated solution of NaHCO$_3$ (200 mL) at room temperature was added βME (20 μL). After stirring for 1 h, the mixture was concentrated and was purified by reversed phase chromatography (10:0→7:3 H$_2$O:MeCN) to yield 11 as a yellow solid. Data for 11: LRMS (ESI)$^-$ Calc for $C_{31}H_{36}N_7O_{10}S$ (M-H)$^-$: 698.2. Found: 698.1.

Photostationary State Determination by NMR

Cis-trans photoisomerization of MAG-1 conjugated with β-mercaptoethanol (see Supplementary Methods online) was studied by $^1$H NMR, with in situ irradiation of sample using a Polychrom V system monochromator (Till Photonics) containing a 150 W Xenon short arc lamp with an output range of 320-680 nm (29). The half-power bandwidth was 14 nm. A 500 μl aliquot of a 100 μM sample in D$_2$O was prepared in a screw-capped 528-TR-7 NMR tube (Wilmad). A FT-600-UMT fiber optic cable (NA 0.39) (Thorlabs) was coupled at one end to the monochromator using a custom fitting and the other end inserted into the NMR tube a few millimeters above the solution. Each sample was irradiated at the desired wavelength for 30 minutes to reach the photostationary state and 480 scans were required to obtain reasonable signal-to-noise ratios. The output from the fiber optic cable between 340-480 nm ranged from 0.3-9.0 μW/cm$^2$. Data were processed by isolating aromatic cis-trans $^1$H signals and summing their integrals to 1.0. All data were obtained in triplicate and averaged. This analysis will be detailed further in a future paper by Banghart, M. R. et al. (in preparation).

Introduction of Cysteine Residues in the Glutamate Binding Domain of iGluR6.

Cysteine point mutations were introduced to the iGluR6 DNA, containing Q at the position 621 RNA editing site (30)

fetal bovine serum, 0.2 mg/ml streptomycin, and 200 U/ml penicillin at 37° C. Cells were transiently transfected with various plasmids using lipofectamine 2000 (Invitrogen). The amount of total transfected iGluR6 DNA and EYFP fusion DNA per 2 ml well was fixed at 4 μg and 200 ng, respectively. All recordings were carried out 36 to 48 h after transfection.

Conjugation of MAG Compounds.

To conjugate MAG-1 and MAG-2 to iGluR6-L439C, the compounds were diluted in the HEK cell control solution to 100 nM-200 μM from concentrated stock solutions in DMSO (final DMSO concentration being 0.1% at most). These solutions were irradiated for 1 hour with 365 nm light using a handheld UV lamp (UVP model UVGL-25 (multiband 254 nm/365 nm), Upland CA).

Calcium Imaging

Cells were washed in PBS and loaded with 5 μM Fura-2-AM (Molecular Probes) for 30 min. Changes of [Ca$^{2+}$], in individual cells were measured as intracellular Fura2 fluorescence intensity using mercury arc lamp illumination and alternating excitation with band pass filters of 350 nm and 380 nm during 66 ms at 5-20 s intervals and detecting emission at 510 nm (31). Fluorescence was monitored on an inverted microscope system (Nikon). Images were captured with a CCD camera using the Imaging Workbench software, which was also used to irradiate the cells at 380 and 500 nm during 1-2 min in order to produce photoisomerization of MAG. Measurements were performed in a control solution containing (in mM): 135 NaCl, 5.4 KCl, 0.9 MgCl$_2$, 1.8 CaCl$_2$, 10 glucose and 10 HEPES at pH 7.6. Cells were preincubated for 10 min in control solution containing 300 mg/l Concanavalin A type IV (Sigma) in order to block desensitization (32, 33).

L-Glutamate was applied as reported in text and figures. The results are representative data from multiple cells in at least two independent cultures.

Whole-Cell Patch Clamping

Patch clamp recordings were carried out using an Axopatch 200A amplifier in the whole cell mode. Cell voltage was held at −60 mV. Pipettes had resistances 4-8 MΩ and were filled with a solution containing (in mM): 145 CsCl, 5 EGTA, 0.5 $CaCl_2$, 1.0 $MgCl_2$ and 10 HEPES at pH7.2. The extracellular solution and concanavalin preincubation were as in calcium imaging experiments. Blocking experiments were carried out with DNQX disodium salt (Tocris) diluting a 4 mM stock solution in the extracellular solution, up to 100 nM. Leak was subtracted under 500 nm, 4 mM DNQX. For each DNQX concentration, relative response to 380 nm was calculated as I (380 nm, DNQX)/I (380 nm, control), and relative response to 500 nm was calculated as I (500 nm, DNQX)/I (380 nm, control). Glutamate was added as indicated in the figures. Illumination was applied using a TILL Photonics Polychrome II monochromator through a 60×/1.2 W objective (power output: 12.4 $W/m^2$ irradiance; 500 nm as measured with a Newport optical power meter). Data was recorded with pClamp software, which was also used to automatically control the monochromator by means of sequencing keys.

Results

Modular Photoswitchable Tethered Ligands

Figure 10:
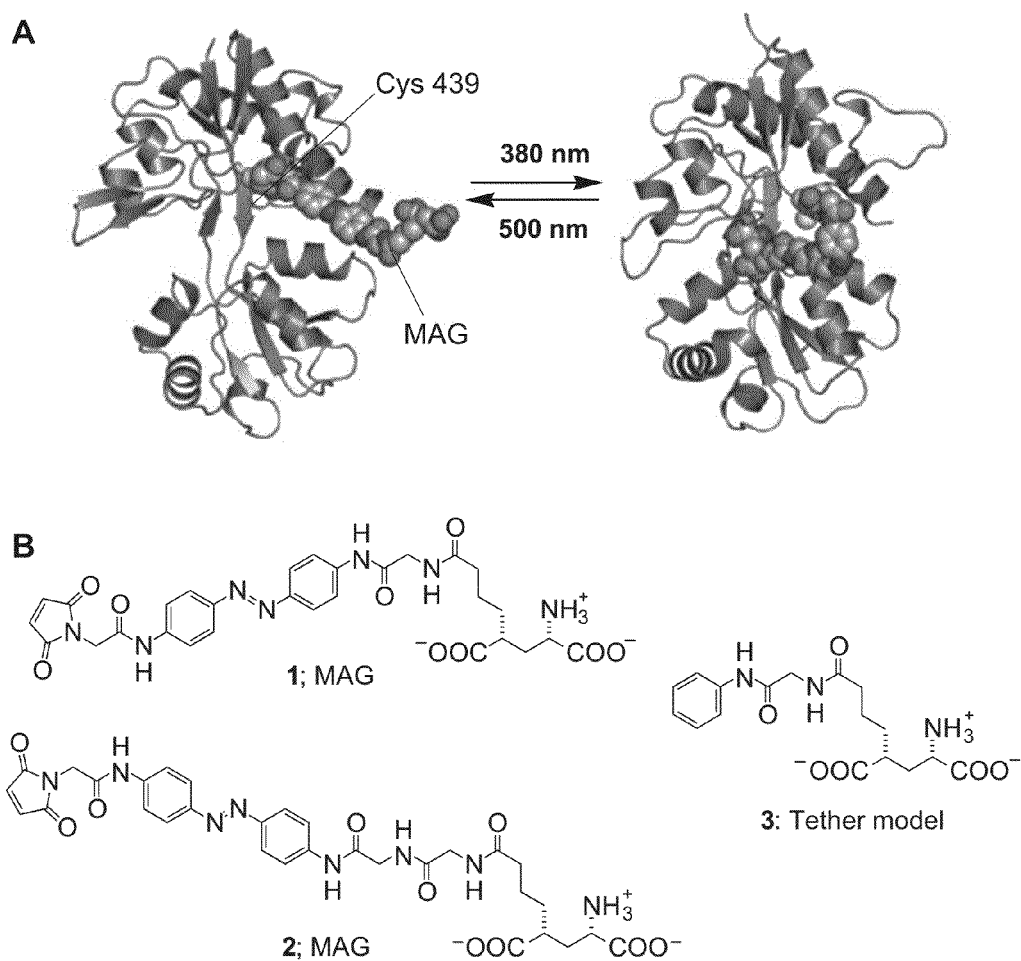
FIGS. 10A and 10B depict modular photoswitchable tethered ligands.

The photoswitchable tethered ligand was designed to possess a maleimide for conjugation to a cysteine residue on the exterior of the LBD, a glutamate analog, and an azobenzene linker in between enabling reversible state-dependent control over the reach of the glutamate analog (Example 2). The glutamate analog was chosen based on previously established structure-activity relationships of the selective iGluR agonists (2S,4R)-4-allyl-glutamate (LY310214) and (2S,4R)-4-methyl-glutamate (SYM 2081) (15, 16, 17), and on our novel iGluR6 agonist, termed the "tether model" (3; FIG. 10b) (Example 2). The modularity of the design allows for the introduction of additional glycine units in the tether with minimal synthetic investment. Initial studies were based upon models of docking MAG-1 in the iGluR6-MeGlu crystal structure (16), while the exact tether length required for optimal activation remained unknown. Following the synthesis of MAG-1, the elongated MAG-2 was synthesized using chemistry analogous to that described in Example 2. Different length MAGs allow for the study of tether length dependence on channel activation and agonist binding using readily accessible and minimally disruptive amino acid building blocks. The success of the MAG design, and the ease with which it can be modified, opens the possibility of replacement of the glutamate moiety for other iGluR agonists or antagonists, or application to other similarly functioning allosteric proteins with well defined ligand binding modes.

FIGS. 10A and 10B. Modular photoswitchable tethered ligands.

(A) The light-gated glutamate receptor operates by reversibly binding of the photoswitchable agonist MAG (Example 2) which is attached covalently to a cysteine introduced in the ligand binding domain of the receptor. The ribbon structure of apo-iGluR2 (Protein Data Bank accession code 1 FTO) (18) is shown on the left, together with the ball-and-stick structure of MAG in the extended (trans) and unbound conformation. Under 380 nm illumination MAG-1 can activate the receptor as is shown on the right with cis-MAG-1 docked on the structure of iGluR6 in complex with (2S,4R)-4-methyl glutamate (Protein Data Bank accession code 1FTO) (19). Photoswitching is reversible with 500 nm illumination. (B) The structure of MAG-1 (Example 2) can be elongated by introducing an additional glycine unit (MAG-2). Compound 3 is a non-photoswitchable MAG-1 analog and an iGluR6 agonist termed the "tether model".

Photostationary State Determination by NMR

Figure 11:
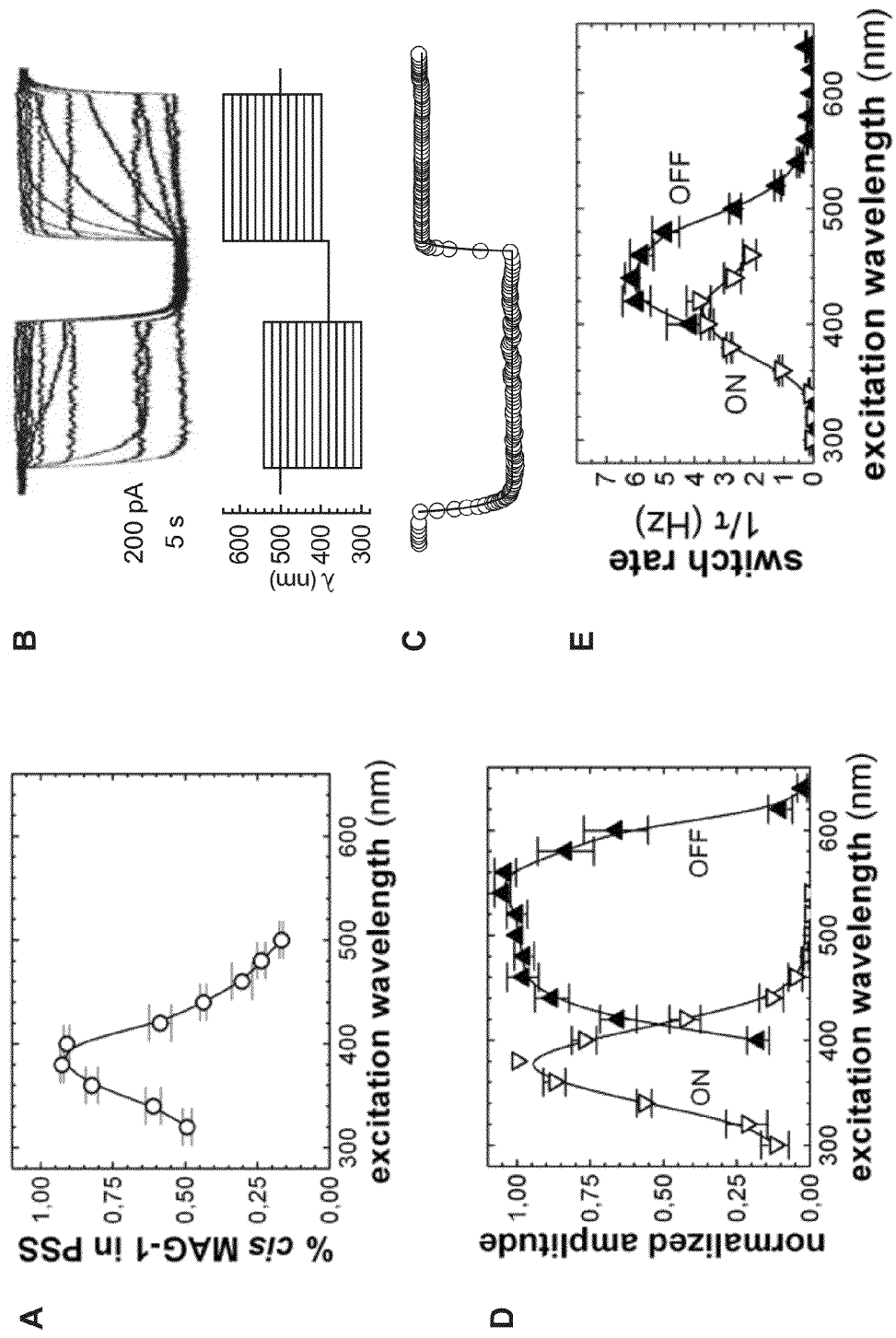
FIGS. 11A-E depict photostationary state determination by NMR and spectral sensitivity of photoresponses.

In the thermally relaxed state, azobenzene exists almost entirely in the trans configuration (20). Upon illumination, a mixture is generated, with a fraction of the azobenzene in the cis configuration and the rest in trans. The balance between cis and trans (the photostationary state) depends on the wavelength. The cis population is maximally populated in the near UV, and trans population is maximally populated in the visible range of the light spectrum. Usually absorbance is used to determine the fraction of azobenzene in the two states. This requires determination of the UV and visible spectra of the two isomers, which partially overlap. Here we used a novel approach of NMR spectroscopy to distinguish between the two isomers. NMR was used to determine the ratio of cis- to trans MAG-1 conjugated to β-mercaptoethanol between 340 and 500 nm, at 20 nm increments (FIG. 11a). Optimal wavelengths for cis and trans populations were found to be 380 and 500 nm, respectively. At 380 nm 93.0±0.6% of MAG-1 is in the cis-state and at 500 nm 83.0±0.6% of MAG-1 is in the trans-state.

Spectral Sensitivity of Photoresponse Produces an Analog Output

In order to quantify the relationship between the photostationary state of MAG-1 in solution and after conjugation to iGluR6-L439C, the current amplitude and switching kinetics were measured as a function of wavelength. Activation was examined by stepping wavelengths from maximal steady-state deactivation (500 nm) to a series of shorter wavelengths. The step duration was selected to be 10 s, long enough for currents to reach steady state. Deactivation was examined by starting at the wavelength of maximal steady-state activation (380 nm) and stepping to longer wavelengths (FIG. 11b). The activation and deactivation components were each well fit with a single exponential (FIG. 11c). The activation spectrum is centered at 380 nm (FIG. 11d "On"), and falls off steeply at higher and lower wavelengths. The deactivation spectrum is broader and is centered at −500 nm (FIG. 11d "Off"), with wavelengths between 460 and 560 nm yielding maximal deactivation. The NMR-based determination of the photostationary states of MAG-1 in solution, over the wavelength range of 320-500 nm, closely match the action spectrum of channel activation when MAG-1 is conjugated to the channel protein (FIG. 11a). Furthermore, the on and off rates were fastest at wavelengths between 380 nm and 500 nm (FIG. 11e).

FIGS. 11A-E. Photostationary State Determination by NMR and Spectral Sensitivity of Photoresponses.

(A) Fraction of MAG-1 in the cis form determined from NMR spectroscopy. Maximal wavelengths for cis and trans populations are 380 and 500 nm respectively. (B) Wavelength dependence of photoresponses of iGluR6-L439C conjugated to MAG-1, measured by whole-cell patch clamp. The current vs. time traces and corresponding wavelength step protocol used to record action spectra are indicated. The first set of steps (activation spectrum) start at the wavelength of maximal deactivation (500 nm) and span UV illuminations of increasing wavelength. The second set of steps (deactivation spectrum) start at the wavelength of maximal activation (380 nm) and span visible illuminations of increasing wavelength. (C) Each temporal trace can be fitted with a single exponential function whose amplitude and time constant is used to build the action spectra. (D) The activation spectrum ("ON") is centered on 380 nm and falls off rather steeply at higher and lower wavelengths. The deactivation spectrum ("OFF") is wider, with maximal amplitude between 460 nm and 560 nm. (E) Wavelength dependence of photoswitch rate. Time constants $\tau_{ON}$ and $\tau_{OFF}$ from fits of traces in (b) are represented as switch rates (1/T).

Thermal Relaxation of MAG

Experimentally, it may be advantageous to control channel opening without continuous irradiation. In such situations, a single activating pulse of UV light would be used to initiate activation for extended periods of time (minutes). As such, the MAGs were designed with a 4,4'-azodianiline scaffold modified with amide linkages to the glutamate and maleimide moeities of the molecule. These amide-based azobenzene cores are known to possess half-lives of minutes for the rate of thermal relaxation from the cis-state to the lower energy trans-state in the dark (21).

Figure 12:
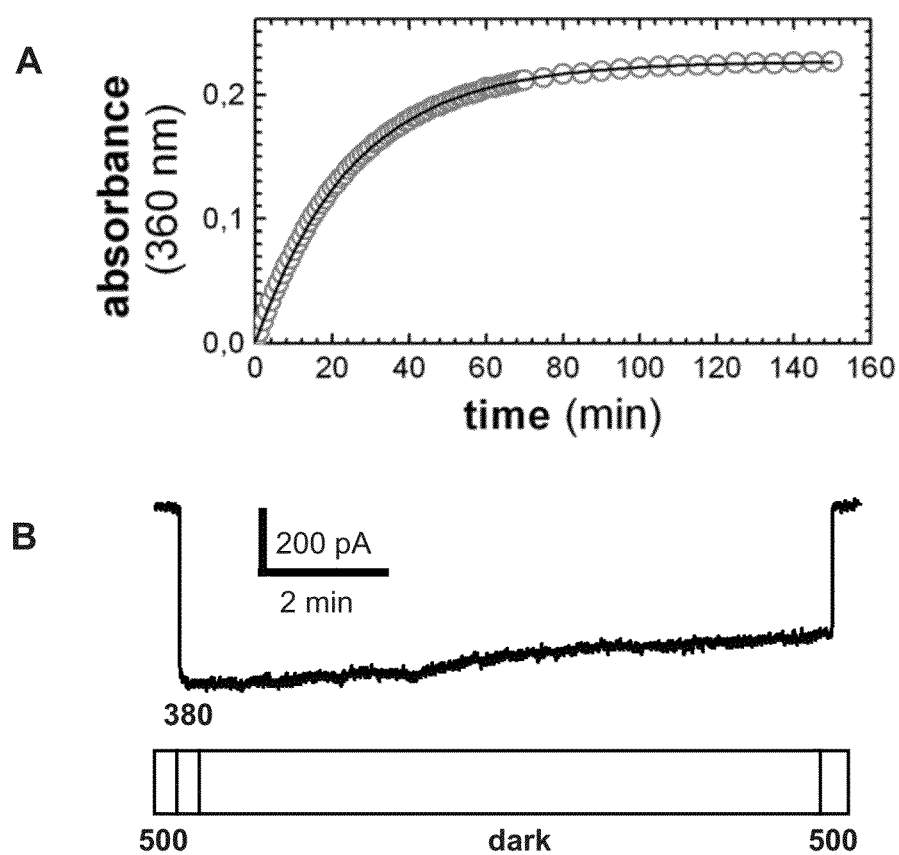
FIGS. 12A and 12B depict thermal relaxation of MAG.

The rate of thermal relaxation in the dark of free MAG-1 from cis to trans was measure; a half-life of 17.65±0.03 min was obtained (FIG. 12a). The spontaneous deactivation in the dark of iGluR6-L439C channels that were conjugated with MAG-1 was examined. Following activation with a 5 s pulse of illumination at 380 nm, there was a 25% decrease in channel current after ten minutes in the dark (FIG. 12b), agreeing closely with the observed half-life of MAG-1 in solution. Similar observations were made on iGluR6-L439C channels that were conjugated with MAG-2. The significance of persistent channel activity in the dark after a brief pulse of illumination is that long-lasting currents can be maintained in absence of irradiation, thus reducing photobleaching of the azobenzene, photo-damage to the protein and photo-toxicity to cells.

FIGS. 12A and 12B. Thermal relaxation of MAG.

(A) Rate of thermal relaxation in the dark of free MAG-1 from cis to trans, measured by absorbance at 360 nm. Traces are exponential and display a half-life of 17.65±0.03 min. (B) Spontaneous rate of deactivation of iGluR6-L439C conjugated to MAG-1, after activation with a 5 s pulse at 380 nm. The current decreases 25% after 10 min.

MAG Conjugation to iGluR6-L439C Occurs by Affinity Labeling

In our first study (14), a model of MAG-1 in the cis-state was docked onto the crystal structure of iGluR6 in complex with (2S,4R)-4-methyl-glutamate. When the glutamate moiety was fit in the agonist binding site, the maleimide end of MAG-1 was able to reach amino acid 439, where the introduced cysteine permits conjugation and yields a light-gated channel (Example 2) (FIG. 10a). This provided a vivid picture of the photoactivated state, and raised the question of whether occupancy of the binding site by MAG-1 would enhance the conjugation efficiency of the maleimide to the cysteine at position 439 by affinity labeling. Affinity labeling has been observed in a variety of systems (22), including in the conjugation of tethered blockers to the Shaker $K^+$ channel (23), which served as a basis for the development of the photoswitchable SPARK channel (13).

Figure 13:
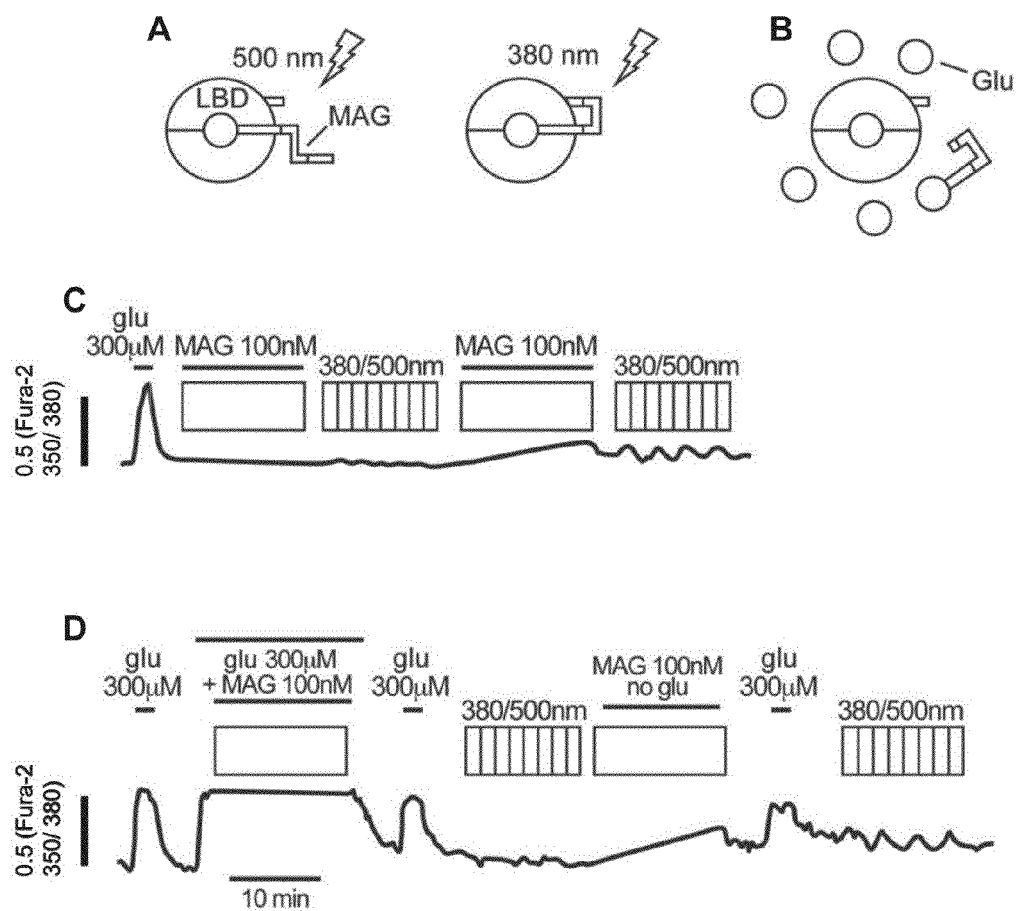
FIGS. 13A-D depict MAG-1 conjugation to iGluR6-L439C by affinity labeling.

In order to investigate the nature of MAG conjugation, affinity labeling was interfered with in two ways. In a first experiment, it was asked whether labeling could be hindered by using visible light to favor the trans-state of MAG-1 conformation, which is expected to extend the maleimide away from cysteine 439 when bound (FIG. 13a). The efficiency of MAG-1 conjugation from the amplitude of photo-responses was evaluated using calcium imaging to detect the activation of the calcium permeant iGluR6 channels, as described in Example 2. Incubation with 100 nM MAG-1 under 380 nm light (favoring the cis-state) produced larger subsequent photo-responses than did incubation under 500 nm light (favoring the trans-state) (FIG. 13c). This is consistent with state-dependent conjugation, which is expected to better position the maleimide near the engineered cysteine when MAG-1 is bound and is in the cis-state.

In a second experiment, affinity labeling was interfered with by occupying the ligand binding site with saturating free glutamate during the incubation period (FIG. 13b). Incubation was carried under 380 nm light to favor the cis-state, as shown above. Incubation of iGluR6-L439C with 100 nM MAG-1 in the absence of free glutamate for 15 min produced significantly larger subsequent photo-responses than did incubation in the presence of 300 µM glutamate (FIG. 13d). The disruption of affinity labeling in the presence of glutamate is consistent with competition between the glutamate end of MAG and free glutamate for the ligand binding site.

Together these experiments demonstrate that at low concentrations MAG conjugation operates by affinity labeling. The ability to control photoswitch attachment under UV light opens the possibility of selective labeling only in illuminated regions of a sample.

FIGS. 13A-D. MAG-1 Conjugation to iGluR6-L439C Occurs by Affinity Labeling.

MAG-1 conjugation at 100 nM can be interfered by two means: (A) favoring the trans-configuration with 500 nm illumination, which orients the maleimide away from cysteine 439 when the glutamate is bound at the binding site, and (B) occupying the binding site with free glutamate, thus preventing docking of MAG-1. (C) Photoresponses obtained by calcium imaging after MAG-1 conjugation under the conditions shown in (A). Weak responses are obtained after MAG-1 conjugation at 100 nM under visible illumination (MAG-1 in trans, maleimide away from cysteine 439), but a substantial increase in photoresponses is observed after conjugation under UV (MAG in cis; maleimide near cysteine 439). (D) Weak responses are obtained after MAG-1 conjugation at 100 nM in the presence of 300 µM glutamate (ligand binding pocket occupied), but are substantially increased after MAG-1 conjugation at 100 nM in the absence of glutamate.

Concentration Dependence of MAG Conjugation

Previous work had demonstrated that the photo-currents of iGluR6-L439C conjugated to MAG-1 are smaller than the currents induced by saturating glutamate (300 µM). It was asked whether the partial activation by iGluR6-L439C-MAG-1 is due to incomplete MAG conjugation. Using whole-cell patch clamping labeled channels were tested with MAG-1 for 1 hour under 380 nm illumination, using concentrations of 0.1, 10, and 200 µM, with the final concentration being the solubility limit of MAG-1. The average photo-current increased with increasing concentration. Relative to the currents evoked by saturating glutamate, the optical activation of iGluR6-L439C-MAG-1 at 380 nm produced currents of 21±8%, 54±20%, and 71±19% at 0.1, 10, and 200 respectively.

It was considered what these values would mean for the activation of a tetrameric protein, with four ligand-binding sites. With complete conjugation, and under optimal excitation at 380 nm illumination to maximize the activating state, each molecule of MAG will spend ~93% of its time in the cis-state. This means that in the tetrameric channel, four LBDs will be activated at the same time 75% (0.93) of the time. Although liganding of only a fraction of a channel's LBDs still generates some current in iGluR5 (24, 25) our results suggest that at the higher concentration we are close to full labeling and that MAG-1 conjugated to iGluR6-L439C functions as an agonist that is similar in potency to glutamate.

MAG Functions as a Full Agonist

It was asked whether, when attached to the channel, MAG-1 operates as a full agonist. The "tether model" was developed (3; FIG. 10b) on which MAG is based to be a full agonist, i.e. to be as effective at activating channels as glutamate itself (Volgraf et al., 2006). When partial agonists bind they allow only partial closure of the LBD and thus only partial channel activation (26). It was asked whether the MAG linker between the maleimide and the glutamate would be constrained in such a way when the maleimide is conjugated to the introduced cysteine that it would partially obstruct closure of the LBD. In the presence of 300 µM glutamate, photoswitching to cis-MAG-1 will compete with glutamate for the binding site and replace some of the free glutamate with MAG-1. If MAG-1 were a partial agonist this would reduce the current (i.e. act as a partial antagonist).

Figure 14:
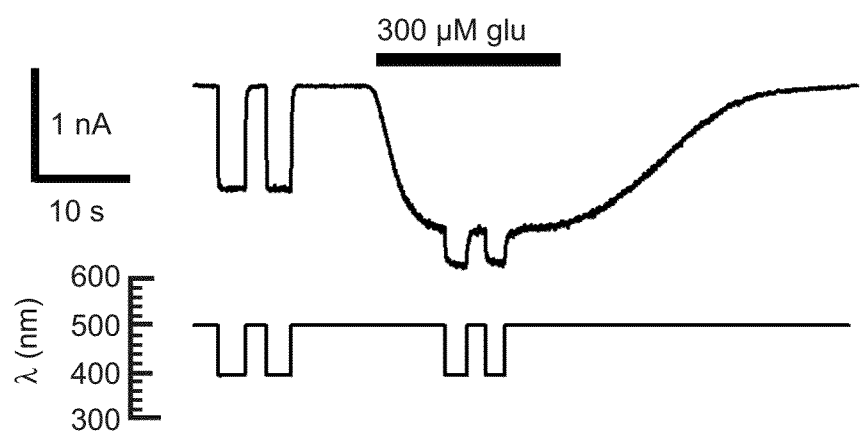
FIG. 14 depicts a patch clamp trace showing that MAG functions as a full agonist.

This prediction was tested and found that iGluR6-L439C conjugated with 100 µM MAG-1 for 15 minutes (i.e. expected to yield substantial, but likely incomplete conjugation, see above) did not show a sign of partial antagonism. Rather than decrease currents, photo-activation (isomerization to cis at 380 nm) of iGluR6-L439C-MAG-1 in the presence of glutamate slightly increased the current (FIG. 14). This observation argues that MAG-1 is actually a slightly better agonist than glutamate.

FIG. 14. MAG functions as a full agonist. Patch clamp trace showing responses to 380 nm illumination that are lower than glutamate 300 µM responses. When photoresponses are elicited during glutamate perfusion, they result in a slight current increase rather than a decrease, indicating that when MAG displaces glutamate it acts as a full and not partial agonist.

High Effective Local Concentration of MAGs

It was shown in Example 2 that agonist 3, a MAG analogue lacking a maleimide and full-length azobenzene, has an $EC_{50}$ of 180 µM for activating iGluR6. Although compound 3 possesses a relatively weak affinity, the local concentration of the glutamate end of cis-MAG-1 when conjugated to iGluR6-L439C is expected to be very high based on its short tether.

Figure 15:
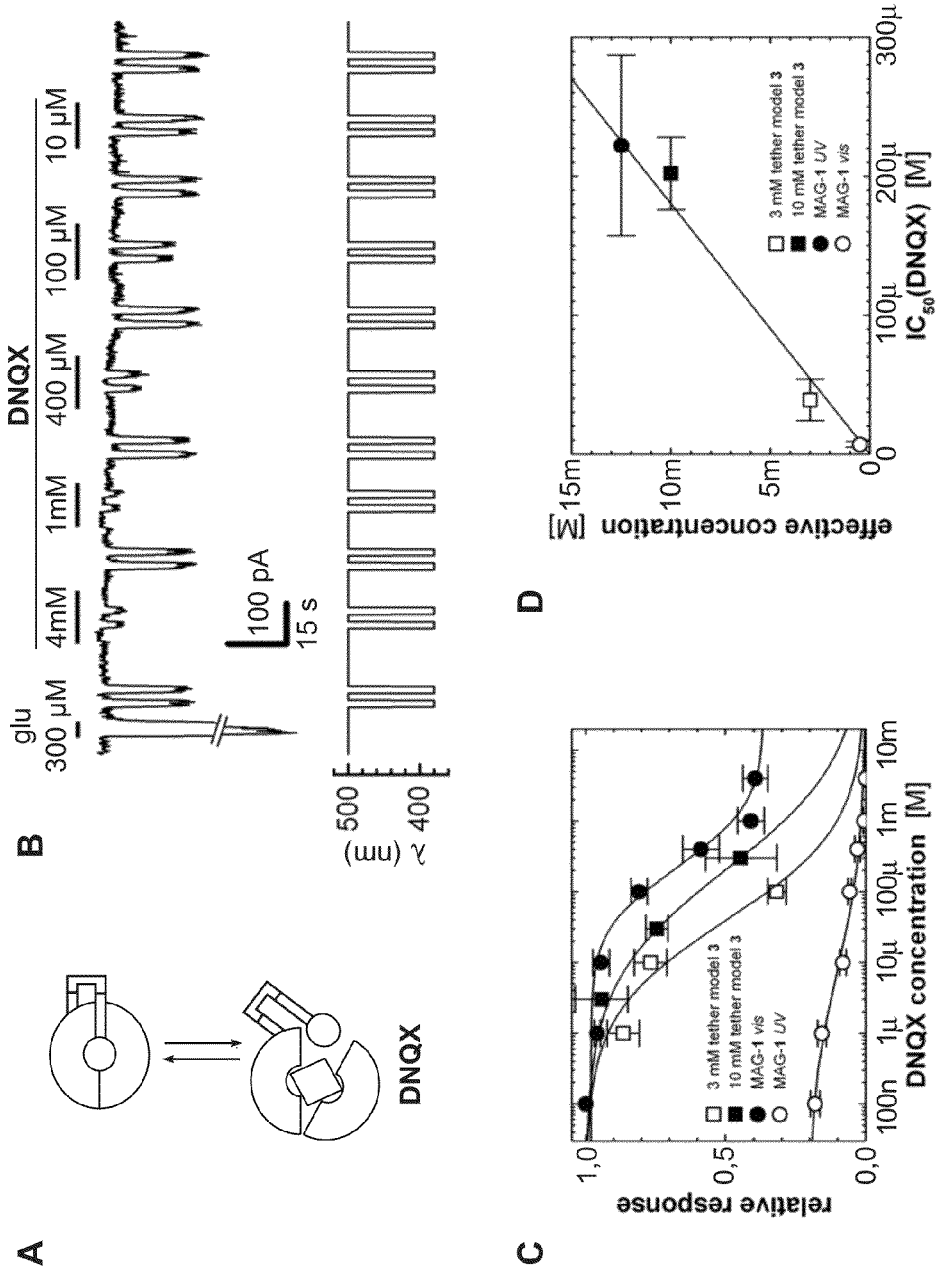
FIGS. 15A-D depict results showing that the effective local concentration of MAG-1 is ~12 mM.

To test this idea, the effective concentration of the glutamate end of MAG-1 was estimated using the competitive antagonist DNQX (27). DNQX inhibits iGluR activation by occupying the glutamate binding site and stabilizing an open conformation of the LBD (FIG. 15a) (28). The ability of DNQX to competitively inhibit the responses of iGluR6-L439C to light-activation with MAG-1, and to perfusion with compound 3 or glutamate, was examined. DNQX inhibited the response to MAG-1 at 380 nm illumination in a concentration dependent manner and was completely reversible upon washout (FIG. 15b). The inhibition curve had a 50% inhibition ($IC_{50}$) of the cis-state light response at 220±65 µM DNQX (FIG. 15c). Even at the DNQX solubility limit of 4 mM the block of the photo-current was incomplete.

To calculate the local concentration of the glutamate end of MAG-1 DNQX competition versus compound 3, the closest soluble MAG analogue, was examined. The concentration dependence of DNQX inhibition was measured using two known concentrations of the tether model (3 mM and 10 mM, the latter being the solubility limit) in order to extrapolate effective MAG concentrations from their DNQX $IC_{50}$. At 3 mM and 10 mM concentrations of compound 3 DNQX $IC_{50}$ values of 39±15 µM and 202±26 µM, respectively, were obtained (FIG. 15c). Thus, inhibition by DNQX reveals that in the cis-state the glutamate moiety of MAG-1 has an effective concentration of 12.5 mM (FIG. 15d). Such a high effective concentration (50-fold greater than the $EC_{50}$ of compound 3) suggests that the photo-switched tethered ligand functions as designed on the channel, generating a very high effective local concentration in the cis-state.

The antagonist competition experiment revealed the existence of a basal current of ~20% at 500 nm that was blocked by DNQX. The $IC_{50}$ value of block of this basal current by DNQX was quantified, and found to be 7±2 µM (FIG. 15c). This value indicates an effective glutamate concentration of 0.5 mM, that is ~30-fold lower than what we measured at 380 nm (FIG. 12d), supporting the model that light turns the channel on and off because photoisomerization of the azobenzene repositions MAG-1 and changes its ability to bind in the glutamate binding pocket.

FIGS. 15A-D. Effective Local Concentration of MAG-1 is ~12 mM.

(A) The competitive antagonist DNQX inhibits iGluR activation by occupying the glutamate binding site without allowing clamshell closure. (B) Patch clamp current traces of iGluR6-L439C conjugated to MAG-1 show responses to perfusion of glutamate 300 µM and to illumination. The corresponding wavelength-time traces are shown below. Perfusion of DNQX partially inhibits photoresponses to 380 nm illumination and reveals a basal activation under 500 nm illumination Inhibition by DNQX is reversible upon washout after each DNQX perfusion. (C) Quantification of DNQX inhibition of photoresponses and comparison to its effect on compound 3. Current under 380 nm light (●) is inhibited by DNQX to 36% of total photoresponse ($IC_{50}$=220 µM DNQX) and the current under 500 nm (○) is completely blocked, which reveals a basal activation ~20% of total photoresponse, $IC_{50}$=7 µM DNQX. For comparison, DNQX blocks responses to 10 mM tether model 3 (■, $IC_{50}$=202 µM DNQX) and 3 mM tether model 3 (□, $IC_{50}$=39 µM DNQX). (D) Determination of the effective concentration of MAG-1 as a function of the DNQX $IC_{50}$ values. The $IC_{50}$ values for DNQX/tether model 3 are used to calibrate the local concentration axis assuming a linear relationship (straight line), and yield 12.5 mM and 0.5 mM for MAG-1 under UV and visible respectively.

Tether Length Dependence on Channel Activation

Figure 16:
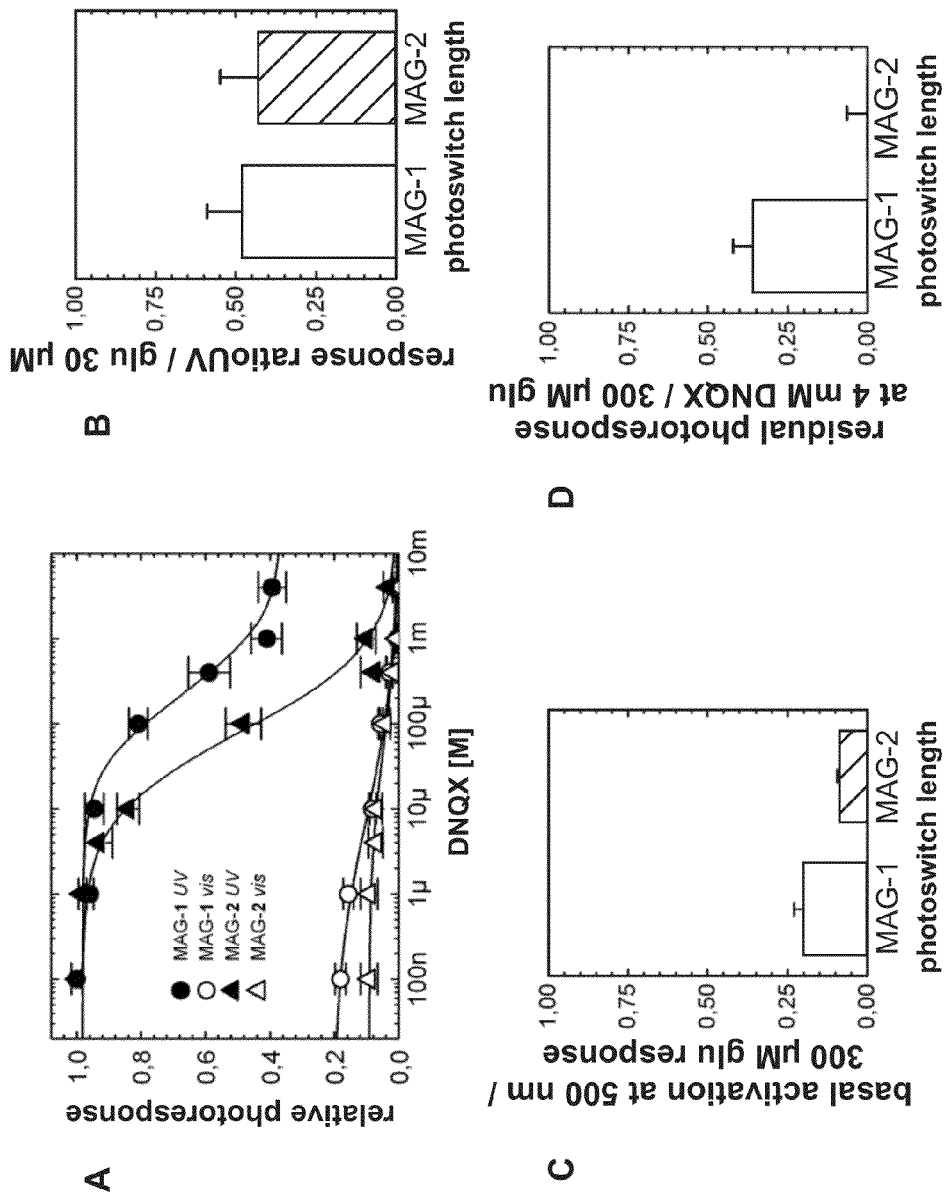
FIGS. 16A-D depict tether length dependence on channel activation.

The dependence of light-gating on tether length was investigated using an elongated tethered ligand, MAG-2 (FIG. 16a). It was found that for iGluR6-L439C conjugated to MAG-2 at 10 µM for 1 h the amplitude of the photoresponse at 380 nm was 43±12% that of the current evoked by saturating glutamate, slightly lower than what was measured for iGluR6-L439C-MAG-1 (FIG. 16b). Competition studies on iGluR6-L439C-MAG-2 using DNQX yielded an $IC_{50}$ under 380 illumination of 80±20 µM, indicating an effective concentration that was ~3-fold lower than that observed for MAG-1. Consistent with the lower effective concentration of MAG-2 in the cis-state, the basal activation was lower than for MAG-1 (FIG. 6c) and high concentrations of DNQX completely blocked the photo-current at 380 nm for iGluR6-L439C-MAG-2, even though block was only partial for MAG-1 (FIG. 16d).

FIGS. 16A-D. Tether Length Dependence on Channel Activation.

(A) DNQX titrations of iGluR6-L439C conjugated to MAG-1 (UV ●, vis ○) and MAG-2 (UV ▲, vis △). (B) Amplitude of MAG-1 and MAG-2 photoresponses after conjugation at 10 µM for 1 h, compared to 300 µM glutamate responses. (C) Basal activation of iGluR6-L439C conjugated to MAG-1 and MAG-2. (D) Residual photoresponse for MAG-1 and MAG-2 after 4 mM DNQX.

REFERENCES

1. Yuste R (2005) *Nat Methods* 2:902-904.
2. Rougvie A E (2001) *Nat Rev Genetics* 2:690-701.
3. Gurney A M (1994) in *Microelectrode techniques*, The Plymouth workshop handbook (2nd. edition) ed Ogden D C (Company of Biologists, Cambridge, UK).

4. Lechner H A, Lein E S & Callaway E M (2002) *J Neurosci* 22:5287-5290. Erratum in: *J Neurosci* 22:1a (2002).
5. Callaway E M (2005) *Trends Neurosci* 28:196-201.
6. Lima S Q & Miesenbock G (2005) *Cell* 121:141-152.
7. Erlanson D A, Braisted A C, Raphael D R, Randal M, Stroud, R M, Gordon E M & Wells J A (2000) *Proc Natl Acad Sci USA* 97:9367-9372.
8. Koçer A, Walko M, Meijberg W & Fering a BL (2005) *Science* 309:755-758.
9. Bose M, Groff D, Xie J, Brustad E & Schultz P G (2006) *J Am Chem Soc* 128:388-389.
10. Flint D G, Kumita J R, Smart O S & Woolley G A (2002) *Chem Biol* 9:391-397.
11. Guerrero L, Smart O S, Woolley G A & Allemann R K (2005) *J Am Chem Soc* 127:15624-15629.
12. Lester H A, Krouse M E, Nass M M, Wassermann N H & Erlanger B F (1980) *J Gen Physiol* 75:207-232.
13. Banghart M, Borges K, Isacoff E, Trauner D & Kramer R H (2004) *Nat Neurosci* 7:1381-1386.
14. Volgraf M, Gorostiza P, Numano R, Kramer R H, Isacoff E Y & Trauner D (2006) *Nat Chem Biol* 2:47-52.
15. Pedregal C, Collado I, Escribano A, Ezquerra J, Dominguez C, Mateo A I, Rubio A, Baker S R, Goldsworthy J, Kamboj R K, Ballyk B A, Hoo K & Bleakman D (2000) *J Med Chem* 43:1958-1968.
16. Mayer M L, Ghosal A, Dolman N P & Jane D E (2006) *J Neurosci* 26:2852-2861.
17. Donevan S D, Beg A, Gunther J M & Twyman R E (1998) *J Pharmacol Exp Ther* 285:539-545.
18. Armstrong N & Gouaux E (2000) *Neuron* 28:165-181.
19. Mayer M L (2005) *Neuron* 45:539-552.
20. Woolley G A (2005) *Acc Chem Res* 38:486-493.
21. Pozhidaeva N, Cormier M E, Chaudhari A & Woolley G A (2004) *Bioconjug Chem* 15:1297-1303.
22. Chen G, Heim A, Riether D, Yee D, Milgrom Y, Gawinowicz M A & Sames D (2003) *J Am Chem Soc* 125:8130-8133.
23. Blaustein R O (2002) *J Gen Physiol* 120:203-216.
24. Rosenmund C, Stern-Bach Y & Stevens C F (1998) *Science* 280:1596-1599.
25. Popescu G, Robert A, Howe J R & Auerbach A (2004) *Nature* 430:790-793.
26. Jin R, Banke T G, Mayer M L, Traynelis S F & Gouaux E (2003) *Nat Neurosci* 6:803-810.
27. Honore T, Davies S N, Drejer J, Fletcher E J, Jacobsen P, Lodge D & Nielsen F E (1988) *Science* 241:701-703.
28. Sun Y, Olson R, Horning M, Armstrong N, Mayer M & Gouaux E (2002) *Nature* 417:245-253.
29. Tait K M, Parkinson J A, Bates S P, Ebenezer W J & Jones A C (2003) *Photochem Photobiol* 154:179-188.
30. Kohler M, Burnashev N, Sakmann B & Seeburg P H (1993) *Neuron* 10:491-500.
31. Grynkiewicz G, Poenie M & Tsien R Y (1985) *J Biol Chem* 260:3440-3450.
32. Wilding T J & Huettner J E (1997) *J Neurosci* 17:2713-2721.
33. Partin K M, Patneau D K, Winters C A, Mayer M L & Buonanno A (1993) *Neuron* 11:1069-1082.

Example 4

Photoswitchable Affinity Labels (PAL) Control Neuronal Firing of Endogenous Ion Channels Methods Cell Culture and Transfection.

HEK293 cells were grown in DMEM containing 5% fetal bovine serum, at 37° C., 7% $CO_2$. For electrophysiology, cells were plated at $12\times10^5$ cells/$cm^2$ on poly-L-lysine coated coverslips and transfected using the calcium phosphate method. Recordings were performed 24-36 hours after transfection.

Hippocampal neurons were prepared from neonatal Sprague-Dawley rats according to standard procedures (Goslin) and grown on poly-L-lysine coated coverslips in MEM supplemented with 5% fetal bovine serum, B27 (Invitrogen), glutamine and serum extender (BD Biosciences). Animal care and experimental protocols were approved by the UC Berkeley Animal Care and Use Committee. Recordings were performed 9-16 days after plating. The Shaker construct also contains an N-terminal deletion (Δ6-46) to minimize fast inactivation.

Brain Slice Preparation.

Parasagittal cerebellar slices were prepared using standard techniques approved by the UCLA Animal Care Committee. The cerebellum was removed from the cranium of a 14-20 day old Sprague-Dawley rat, mounted on an agar support and sectioned parasagitally using a vibrotome (Leica VT-1000) while submerged in cold (<4° C.) artificial cerebrospinal fluid (aCSF) containing in mM: 119 NaCl, 26 $NaHCO_3$, 11 glucose, 2.5 KCl, 2.5 $CaCl_2$, 1.3 $MgCl_2$, and 1 $NaH_2PO_4$ and saturated with 95% $O_2$ and 5% $CO_2$ Following sectioning, the 300 μM slices were stored in 35° C. aCSF for 30 minutes and brought to room temperature for subsequent electrophysiological experiments.

PAL Attachment.

HEK293 and hippocampal cells were rinsed in extracellular solution containing in mM: 138 NaCl, 1.5 KCl, 1.2 $MgCl_2$, 2.5 $CaCl_2$, 5 HEPES, 10 glucose and incubated at 37° C. in the dark with 200-250 μM PAL for 15 minutes. For slices, AAQ was diluted to 200 μM in aCSF and treatment was performed in the dark at room temperature for 10 minutes.

Live/Dead Assay.

After PAL treatment, hippocampal neurons were processed for the live dead assay (Molecular Probes) according to the manufacturer's instructions. Cells were counted in 4-8 fields for each treatment condition.

Electrophysiological Recording.

Recordings from HEK293 and hippocampal neurons were made in the whole-cell patch clamp configuration using a PC-501A amplifier (Warner Instruments). Pulse protocols and measurements were carried out with pCLAMP and a Digidata 1322 interface (Axon Instruments). For voltage-clamp experiment, cells were held at −70 mV. Data was recorded at 20 kHz and filtered at 2 kHz. Recording pipettes with 2.5-4 MΩ resistance were filled with intracellular solution containing in mM: 10 NaCl, 135 K-gluconate, 10 HEPES, 2 $MgCl_2$, 2 MgATP, 1 EGTA, pH 7.4.

For cerebellar slices, neuronal cell bodies were visualized using an upright microscope with a 40× water immersion lens and equipped with an infrared-DIC enhancement. Loose-patch extracellular recordings were performed using an Axopatch 200B amplifier (Axon Instruments). Electrophysiological recordings were filtered at 1 KHz and digitized at 2-4 KHz. Pipettes were typically 1.4-2.0 MΩ for recordings from PNs and 3.0-3.5 MΩ for interneurons and filled with aCSF. For PN recordings, 6,7-dinitroquinoxaline-2,3-[1H,4H]-dione (DNQX) and gabazine were added when indicated at 20 μM and 10 μM respectively. Recordings from B/S cells were made in the presence of DNQX, gabazine and 5 μM [RS]-3-[2-carboxypiperazin-4-yl]-propyl-1-phosphonic acid (CPP). All recordings were performed at room temperature.

Illumination was provided using a xenon lamp (Sutter Instruments) with narrow band pass filters (380 BP10 for UV and 500 BP5 for visible light respectively). Excitation filters were changed using a lambda 10-2 filter changer (Sutter Instruments) controlled via pCLAMP software.

Percent photoswitching was defined as the difference between current in UV and visible light divided by current in UV. All data shown in bar graphs are averages±standard error of the mean.

Results

The PAL Approach.

Figure 17:
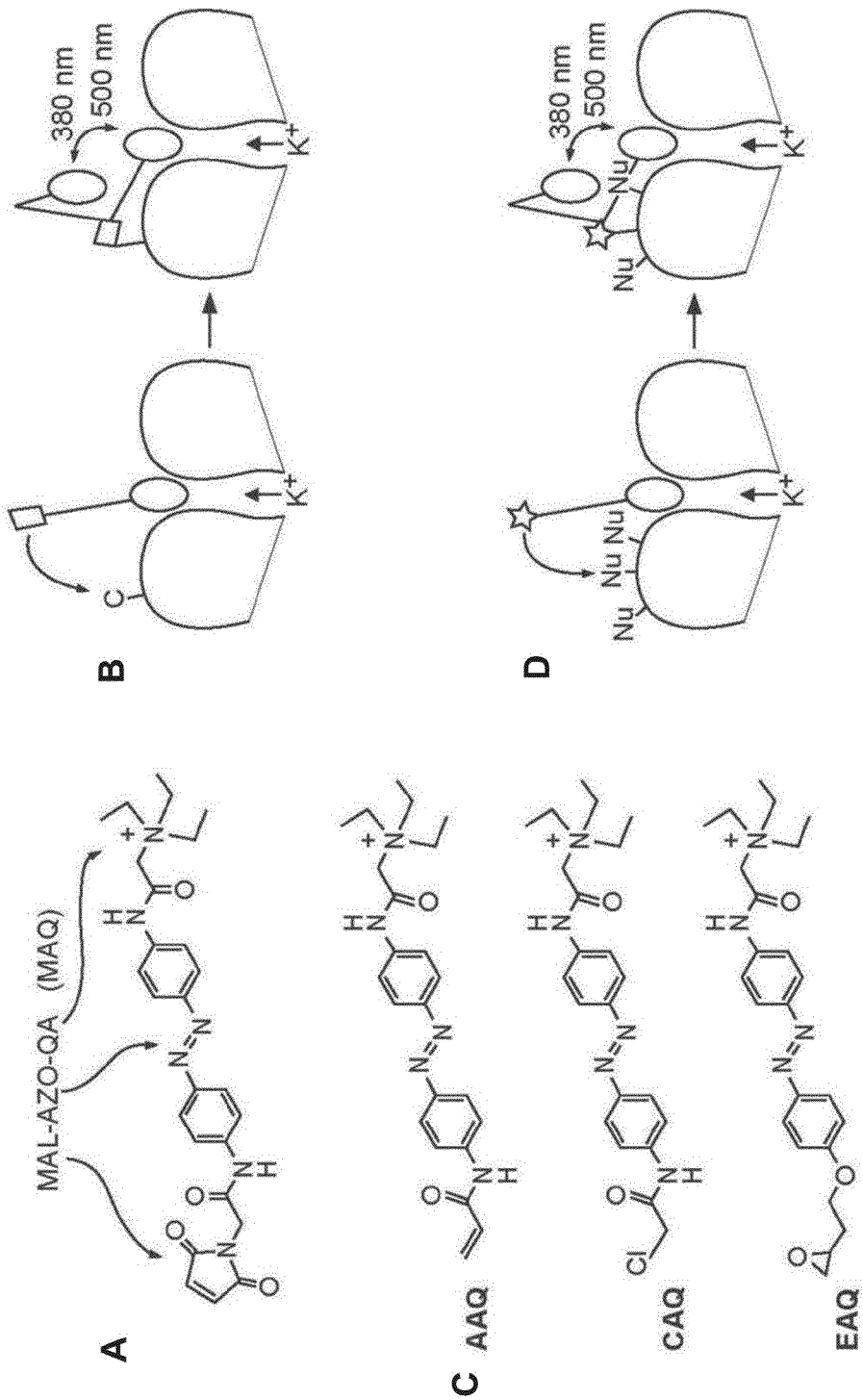
FIGS. 17A-D depict the photoswitchable affinity label (PAL) approach to generating light-regulated ion channels.

The photoswitch used in SPARK channels is a derivative of the photoisomerizable molecule azobenzene (AZO) (FIG. 17a). Connected to the AZO on one end is a cysteine-reactive maleimide (MAL) group, which allows attachment to a specific cysteine that was introduced into an extracellular site on the Shaker protein, and on the other end a quaternary ammonium (QA) group, which can block the pore of $K^+$ channels. The photoswitch molecule (MAL-AZO-QA, or for simplicity "MAQ") is designed so that the QA can reach the pore and block ion conduction when the AZO is in its elongated trans form, but not in its bent cis form (FIG. 17b). Exposure to 360-400 nm light photoisomerizes the AZO from trans to cis, unblocking the channel, whereas long wavelength light (450-520 nm) restores the blocked state by accelerating the reverse cis to trans conversion.

The PAL molecules that were designed for native $K^+$ channels are similar to MAQ, with one important difference. Instead of maleimide, which is commonly used as a cysteine-modifying reagent, PALs contain an electrophilic group that was presumed would be more "promiscuous" (FIG. 17c), potentially reacting with a variety of nucleophilic amino acids. The following sequence of events when a PAL encounters a QA-sensitive $K^+$ channel (FIG. 17d) was envisioned. First, the QA binds to the pore, slowing its departure from the vicinity of the channel. This increases the local effective concentration of the reactive electrophilic moiety, promoting covalent attachment to the channel protein, if it happens to possess a nucleophilic amino acid side chain at an appropriate distance from the QA binding site (~20 Å away). Hence, the labeling of native channels by the photoswitch is promoted by the ligand binding interaction, as in classical affinity labeling (Johnson and Cantor, 1977; Chowdry and Westheimer, 1979). In contrast to SPARK channels, where two components need to be added to cells (i.e. the Shaker channel gene and the MAQ photoswitch), this is a one-component system, where only PAL is required.

PALs were synthesized with several different reactive electrophiles, including epoxide, chloroacetamide, and acrylamide (FIG. 17c). The epoxide PAL (EAQ) was toxic to cultured neurons (see below). The chloroacetamide PAL (CAQ) was less water-soluble than the acrylamide PAL (AAQ). Therefore, unless noted otherwise, AAQ was used for the experiments described in this example.

FIG. 17A-D. The PAL Approach to Generating Light-Regulated Ion Channels.

(a) The photoswitch MAL-AZO-QA (MAQ) consists of photoisomerizable azobenzene (AZO) flanked by a quaternary ammonium (QA) group and a cysteine-specific maleimide (MAL) reactive group. (b) MAQ reacts with $K^+$ channels that contain a genetically engineered cysteine located 20 Å away from the pore allowing photocontrol of ionic current. In visible light (green), the photoswitch is extended, blocking ion conduction. In UV light (purple), AZO isomerizes to its cis form retracting the QA and allowing ion conduction. (c) PALs are identical to MAQ except that they contain promiscuous electrophilic groups (red): acrylamide for AAQ, chloroacetamide for CAQ and epoxide for EAQ. (d) After the QA binds to the pore, PALs react with nucleophiles endogenous to $K^+$ channels allowing regulation of native $K^+$ channels with light.

PAL Imparts Light-Sensitivity on $K^+$ Channels

Figure 18:
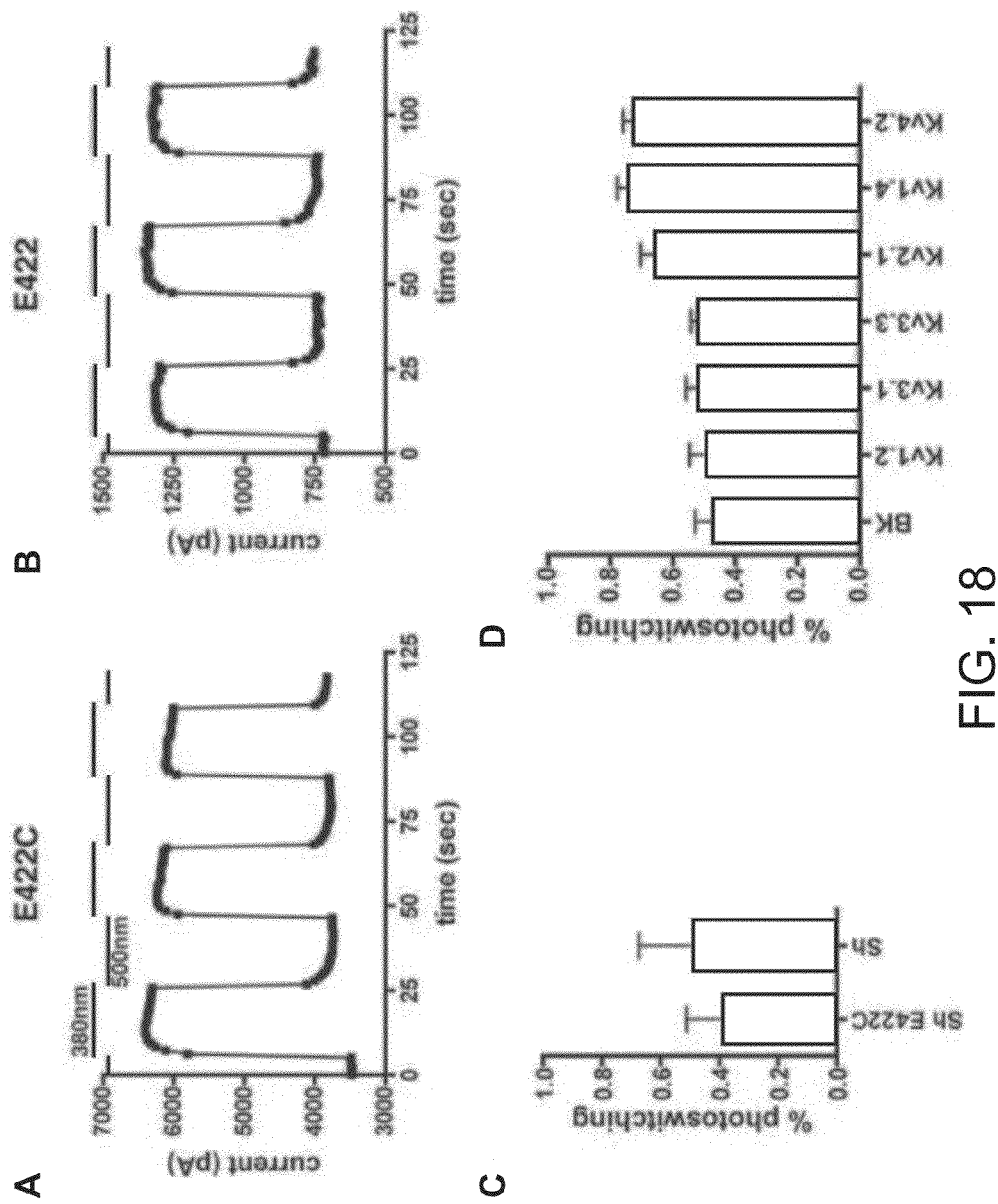
FIGS. 18A-D depict photocontrol of wild-type $K^+$ channels.

The feasibility of the PAL approach was assessed, using heterologously-expressed Shaker $K^+$ channels as a test system. Addition of AAQ to a Shaker channel that has a cysteine-substitution (E422C) imparts light-sensitivity on the channel, just like MAQ (FIG. 18a). However, AAQ imparts light-sensitivity to a similar extent on a Shaker channel that does not have the cysteine substitution (E422; FIG. 2b) and indeed, can confer light-sensitivity on a Shaker channel that is completely devoid of extracellular cysteines. The fraction of current that could be photoswitched was 39±1% for E422C and 48±2% for E422 channels (FIG. 18c), not significantly different from one another (n=6; p>0.3; Student's t-test). EAQ and CAQ also conferred light-sensitivity onto wild-type Shaker $K^+$ channels. Hence PALs can find an attachment site at an appropriate distance from the pore, such that light-elicited changes in photoswitch length can allow or disallow block by the QA group.

To better understand how PAL imparts light-sensitivity on Shaker $K^+$ channels, it was attempted to identify the primary covalent attachment site relevant for light-dependent block and unblock. The structure of the conserved extracellular portion of a voltage-gated $K^+$ channel protein (Long et al., 2005) suggests that Shaker possesses at least 9 accessible nucleophilic amino acid side chains that lie within 20 Å of the QA binding site. Mutagenesis of each of these sites suggests that no individual one is essential for PAL to confer light sensitivity (Banghart et al., submitted).

If PALs are promiscuous in reacting with Shaker, perhaps they can also react with other types of $K^+$ channels that possess a QA binding site. This possibility was tested by expressing homomeric versions of Kv1.2, Kv1.4, Kv2.1, Kv3.1, Kv3.3, Kv4.2, and BKα channels in HEK cells (FIG. 18d). Whole-cell patch clamp recordings show that treatment with AAQ imparted light-sensitivity on all of these channels, but some were more sensitive than others. Hence light turned on and off ~80% of the current through Kv1.4 and Kv4.2 channels, but only regulated ~45% of the current through BKα channels.

FIGS. 18A-D. Photocontrol of Wild-Type $K^+$ Channels.

(a) AAQ photosensitizes Shaker channels that contain an engineered cysteine (E422C). Current was elicited by stepping from −70 to +30 mV for 200 msec. Visible light (green) blocks current through the channels whereas UV light (purple) leads to unblock. (b) AAQ photosensitizes wild-type Shaker (E422). (c) Average percent photoswitching is similar for Shaker with or without the engineered cysteine (n=6, p>0.3). (d) AAQ sensitizes a variety of voltage-gated channels to light (n=6 for each channel).

PALs Impart Light-Sensitivity on Ion Channels in Cultured Hippocampal Neurons

Figure 19:
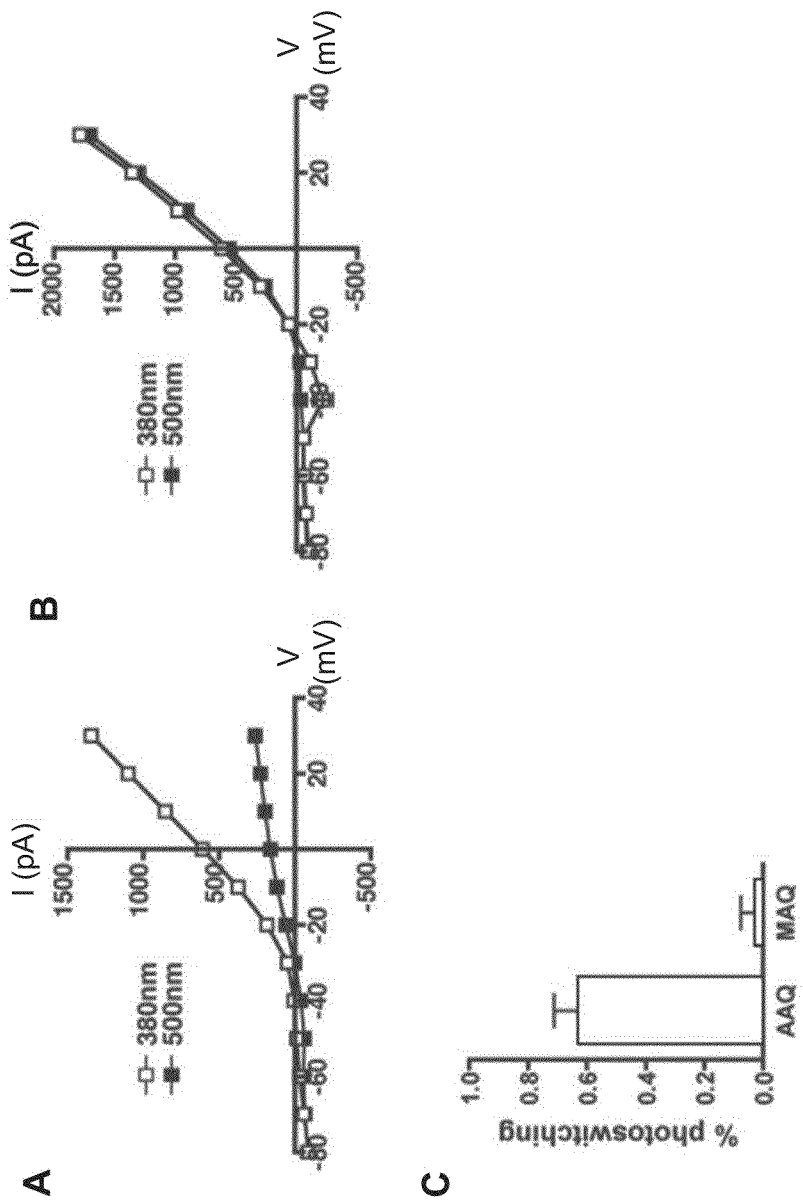
FIGS. 19A-C depict photocontrol of $K^+$ current in cultured hippocampal neurons.

It was next tested whether PALs could impart light-sensitivity onto endogenous $K^+$ channels in neurons. FIG. 19a shows steady-state I-V curves from a hippocampal neuron in culture, treated with 200 μM AAQ in the dark for 15 min before recording. With this treatment, PAL should be in the extended trans configuration, and native channels blocked by PAL should unblock upon photoisomerization to the cis configuration. Consistent with this, exposure to 380 nm light increased the voltage-gated outward current and 500 nm light reversed the effect. Voltage-gated outward current was photoswitched to a similar extent in neurons treated with 200 μM CAQ (not shown). In contrast, MAQ failed to impart light sensitivity on outward current in untransfected neurons that express only their native ion channels (FIG. 19b). The percent of the outward current that could be photoswitched was 63±8% (n=12) and 2±5% (n=6) for AAQ- and MAQ-treated cells, respectively.

Although PALs confer light-sensitivity on many $K^+$ channels, it was expected that other types of channels will be unaffected. External QA is often used to help selectively remove $K^+$ currents and reveal unaltered voltage-gated $Na^+$ and $Ca^{2+}$ currents in neurons. Voltage-clamp recordings with $Cs^+$ in the patch pipette indicate that the transient inward current does not become light-sensitive after treatment with PAL. Moreover, under current clamp, neither the rising phase nor the peak amplitude of action potentials is affected by light.

FIGS. 19A-C. Photocontrol of $K^+$ Current in Cultured Hippocampal Neurons.

(a) Steady-state I-V curves for an AAQ-treated neuron illuminated with UV (purple) or visible (green) light. Illumination with visible light blocks much of the outward current. (b) MAQ with its cysteine-specific reactive group does not sensitize native neuronal channels to light. (c) Average percent photoswitching of outward current in neurons treated with AAQ (n=12) and MAQ (n=6).

PALs Enable Optical Control of Action Potential Firing in Cultured Hippocampal Neurons.

PAL treatment confers light-dependence on action potential firing. Under current clamp conditions, 380 nm light turns off firing and 500 nm light promotes firing in neurons. The effects of light can be quite dramatic (FIG. 20a), with neurons photoswitched between a rapid firing mode (10 Hz) to complete quiescence within milliseconds of switching to 380 nm light and back to repetitive firing with 500 nm light. Indeed, brief (100 msec) flashes of 500 nm light could be used to elicit action potentials on a one-to-one basis (FIG. 20b).

Figure 20:
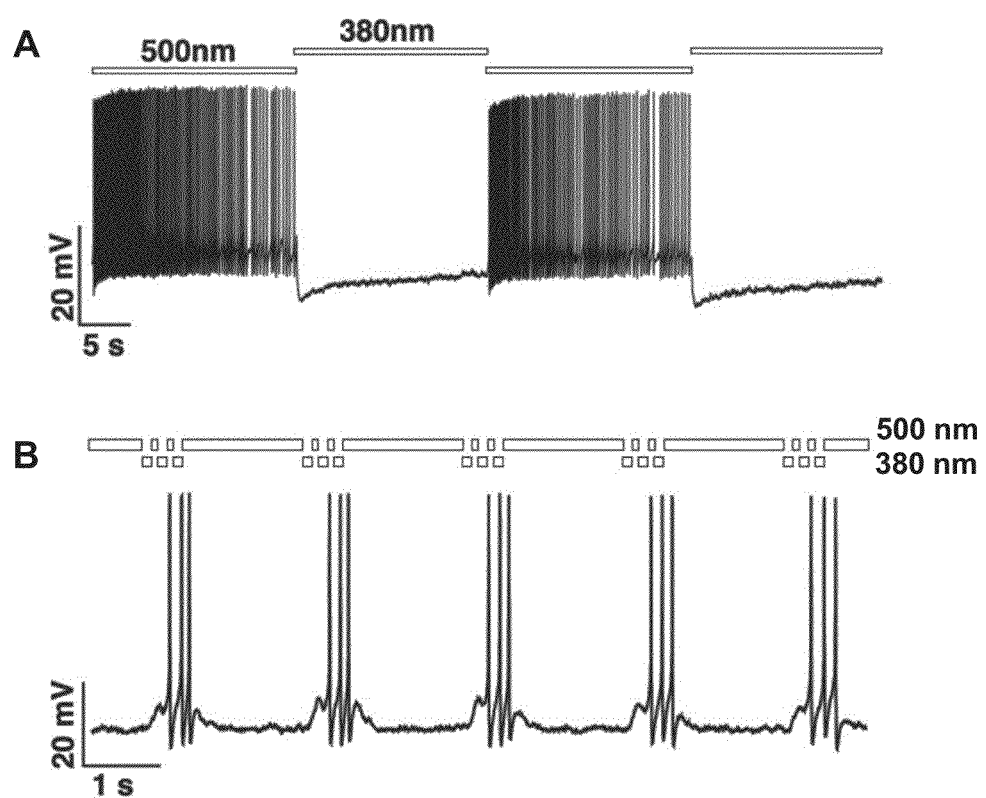
FIGS. 20A and 20B depict regulation of action potential firing with light. The "☐" symbols in FIG. 20B are short bars, and represent pulses of light.

FIGS. 20A and 20B. Regulation of Action Potential Firing with Light.

(a) Current clamp recording of a neuron treated with AAQ. Depolarizing current was injected to induce continuous action potential firing in visible light (green). Illumination with UV light (purple) rapidly suppresses action potential firing. High frequency firing resumes upon illumination with visible light. (b) One-to-one action potential firing upon exposure to short pulses of visible light.

Figure 21:
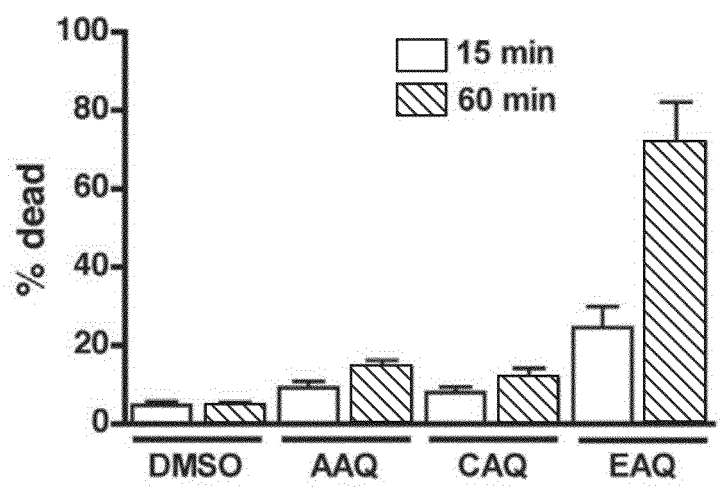
FIG. 21 depicts neuronal survival after PAL treatment.

PAL-modified $K^+$ channels are blocked either in the dark or in visible light keeping the membrane potential tonically depolarized, which might be harmful to neurons. In addition, the reactive electrophile of PAL compounds might have deleterious effects on cells. To quantify the possible toxicity of PALs, we used a fluorescent Live/Dead Assay (FIG. 21). Cultured hippocampal neurons were first incubated for 15 or 60 min with 200 μM of EAQ, AAQ, or CAQ. EAQ was highly toxic to neurons, even with a brief (15 min) treatment time, and was not used further in our studies. In contrast, AAQ and CAQ treatment resulted in the death of ~10% of neurons in 15 min, only slightly greater than following treatment with vehicle alone (DMSO; ~5% in 60 min). Even with a treatment duration that was 4 times greater than needed to modify $K^+$ channels (60 min), AAQ and CAQ resulted in loss of only ~15% of neurons. Additional experiments suggest that AAQ injection into the vitreous humor of the rat eye has no detectable deleterious effects on retinal neurons. Hence at least for these cells and given our treatment conditions, AAQ is not toxic to neurons in vitro and in vivo.

FIG. 21. Neuronal Survival after PAL Treatment.

Hippocampal neurons in culture were incubated with PAL for the indicated time and processed for a Live/Dead assay. Only EAQ resulted in substantial toxicity.

PAL Imparts Light-Sensitivity on Neurons in Cerebellar Slices.

Figure 22:
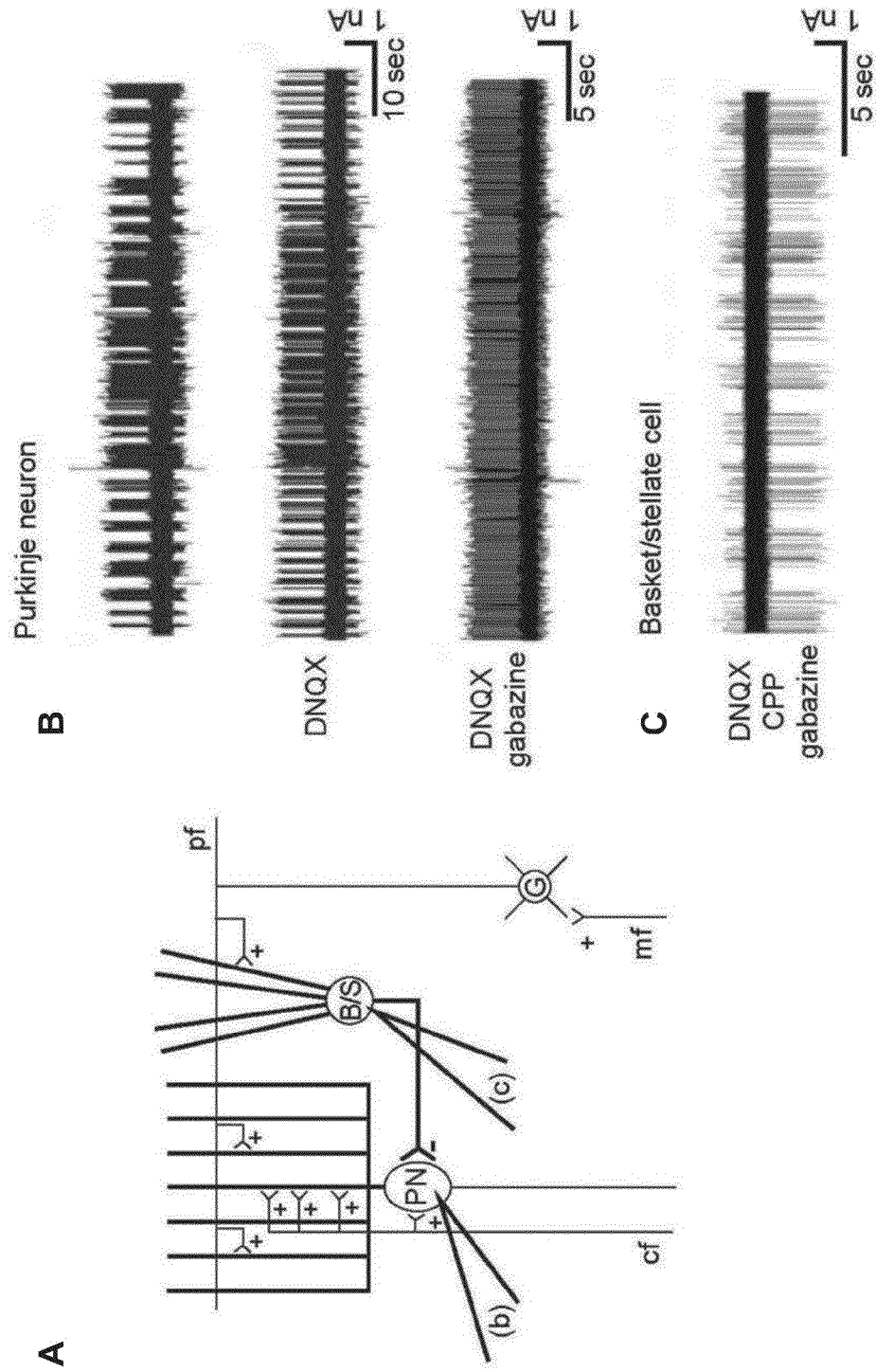
FIGS. 22A-C depict photocontrol of action potential firing in cerebellar slices.

It was next tested whether PAL can regulate activity of freshly obtained neurons in a neural circuit, using parasagittal cerebellar slices obtained from young rats (P14-20). After pre-treating the slice with 200 μM PAL for 10 minutes, a loose patch configuration was used to obtain extracellular recordings from cerebellar neurons (FIG. 22a). Unlike whole-cell recording, this configuration leaves the intracellular milieu intact and minimally perturbs neuronal activity, providing a rigorous test of the effectiveness of the PAL technique under physiological conditions. It was found that full-field illumination of the slice with 360 nm light increased firing frequency by 42±12% (n=5) in Purkinje neurons, and illumination with 500 nm light restored the initial firing rate (FIG. 6b). PAL-mediated sensitization to light was consistently observed in every spontaneously firing neuron tested.

In principle, the observed change in Purkinje cell firing could result from a change in excitatory synaptic input, a change in inhibitory synaptic input, or a change in the intrinsic properties (i.e. voltage-gated ion channels) of the Purkinje cell itself. There may also be a combination of the above effects. To distinguish between these possibilities, the slice was incubated in pharmacological agents that block excitatory or inhibitory synaptic transmission. Addition of the AMPA-receptor antagonist DNQX failed to block light-triggered changes in activity (FIG. 22b). However, subsequent addition of gabazine, a selective $GABA_A$ receptor antagonist, prevented illumination from altering the firing rate, consistent with light regulating the firing of inhibitory neurons. Gabazine increased the basal firing rate of Purkinje cells up to ~15 Hz, and it was considered that the blockade of the light response might be due to gabazine-induced saturation of Purkinje cell firing rather than regulation of inhibitory neuronal firing. However, Purkinje cells can fire at rates up to 40-80 Hz (Hausser and Clark, 1997). Moreover, extracellular recordings from basket cells, the primary source of inhibition to Purkinje neurons (REF), showed that 500 nm light enhanced firing frequency by 324±160% (n=6), even in the presence of a cocktail of neurotransmitter antagonists that block AMPA, NMDA, and $GABA_A$ receptors (FIG. 22c). Taken together, these results indicate that the effects of light on Purkinje cell firing are mediated by inhibitory basket/stellate cells, which are preferentially sensitive to PAL.

FIGS. 22A-C. Photocontrol of Action Potential Firing in Cerebellar Slices.

(a) Simplified circuit diagram of the cerebellum. + and − indicate excitatory and inhibitory synapses. Abbreviations: granule cells, G; parallel fibers, pf; mossy fibers, mf; climbing fibers, cf. Recordings were obtained from Purkinje neurons (PN) and interneurons (basket/stellate cells; B/S). (b) Extracellular loose patch recording from a PN. UV light increased the frequency of action potentials in the PN. DNQX, which blocks excitatory synapses, failed to block the effect of light. Subsequent block of inhibitory synapses with gabazine abolished photocontrol, suggesting that PN photosensitivity is indirect and mediated by inhibitory neurons. (c) Extracellular loose-patch recording from a B/S cell. AAQ renders B/S cells directly photosensitive. Photosensitivity remains after blocking excitatory and inhibitory synapses with DNQX, gabazine, and CPP (an NMDA receptor antagonist). UV light inhibits and 500 nm light restores B/S cell firing. Light had no effect on untreated cells.

Banghart, M., Borges, K., Isacoff, E., Trauner, D. & Kramer, R. H. (2004). Light-activated ion channels for remote control of neuronal firing. *Nat Neurosci* 7, 1381-6.

REFERENCES

Bi A, Cui J, Ma Y P, Olshevskaya E, Pu M, Dizhoor A M, Pan Z H. Ectopic expression of a microbial-type rhodopsin restores visual responses in mice with photoreceptor degeneration. Neuron. 2006 Apr. 6; 50(1):23-33.

Boyden E S, Zhang F, Bamberg E, Nagel G, Deisseroth K. Millisecond-timescale, genetically targeted optical control of neural activity. Nat. Neurosci. 2005 September; 8(9):1263-8.

Kramer, R. H., Chambers, J. J., and Trauner, D. (2005). Photochemical tools for remote control of ion channels in excitable cells. *Nature Chemical Biology* 1:360-365

Nagel G, Brauner M, Liewald J F, Adeishvili N, Bamberg E, Gottschalk A. Light activation of channelrhodopsin-2 in excitable cells of *Caenorhabditis elegans* triggers rapid behavioral responses. Curr Biol. 2005 Dec. 20; 15(24):2279-84.

Shoham S, O'Connor D H, Sarkisov D V, Wang S S. (2005). Rapid neurotransmitter uncaging in spatially defined patterns. *Nat. Methods*. 2:837-43.

Example 5

Remote Control of Neuronal Activity with a Light-Gated Glutamate Receptor

Methods
Photoswitch Synthesis and Generation of L439C Mutant of iGluR6.

Synthesis of MAG and introduction of cysteine L439C in iGluR6 were carried out as described [11].

Cell Culture and Transfection.

HEK293 cells were plated at approximately $3 \times 10^6$ cells/ml on poly-L-lysine-coated glass coverslips and maintained in DMEM with 5% fetal bovine serum, 0.2 mg/ml streptomycin, and 200 U/ml penicillin at 37° C. Cells were transiently transfected with various plasmids using lipofectamine 2000 (Invitrogen). The amount of total transfected iGluR6(L439C) DNA and EYFP DNA per 2 ml well was fixed at 4 μg and 200 ng, respectively. All recordings were carried out 36 to 48 hours after transfection.

Postnatal rat hippocampal neurons (P0-P5) were transfected by the calcium phosphate method and recordings were carried out within 1-8 days post transfection. Neurons for patch-clamp experiments were transfected with either a fusion construct of GFP and iGluR6(439C) or co-transfected with iGluR6(L439C):YFP at a 3:1 ratio; for calcium imaging experiments they were co-transfected with iGluR6(L439C):DsRed at 3:1 ratio.

Conjugation of MAG Compounds.

To conjugate MAG to iGluR6(L439C), the compound was diluted to 10 μM in the control solution (described below) from 1 mM stock solution in DMSO. The cells were incubated in the dark for 10-15 minutes. To conjugate MAG to iGluR6(L439C) in hippocampal neurons for patch-clamping experiments, the compound was diluted to 10 μM in a solution containing (in mM): 150 NMDG-HCl, 3 KCl, 0.5 $CaCl_2$, 5 $MgCl_2$, 10 Hepes, and 5 glucose at pH 7.4.

Calcium Imaging and Spatially Selective Photoswitching

Imaging experiments were carried out on a Zeiss 510 META laser scanning microscope equipped with an Enterprise laser (Coherent) having 351 nm and 364 nm lines, and a 488 nm laser. The objective was a Zeiss Plan Neofluar 25×/0.80 Imm DIC (440542), and the dichroic mirror HFT UV/488/543/633 (both for 488 nm/364 nm photoswitching and Fluo-4 imaging). Measurements with HEK cells were performed in a control solution containing (in mM): 135 NaCl, 5.4 KCl, 0.9 $MgCl_2$, 1.8 $CaCl_2$ and 10 Hepes at pH 7.6. The control solution for hippocampal neurons was (in mM): 115 NaCl, 2.8 KCl, 1.0 $MgCl_2$, 1.0 $CaCl_2$, 10 glucose and 10 Hepes at pH 7.3. L-Glutamate and kainate were applied as reported in the text and figures. Intracellular calcium was imaged with the Fluo-4 indicator (Molecular Probes, Invitrogen) excited at 488 nm and 4% laser power, and measuring emission between 495 nm and 527 nm using the META detector. Cells were conjugated during 10 minutes in 10 μM MAG in 0.3 mg/ml Concanavalin A type VI (Sigma), rinsed, and incubated in 10 μM Fluo-4 in the dark for 1 hour. The experiments were then carried out within 1 hour, to minimize Fluo-4 washout. Region-selective photoswitching was obtained by alternating irradiation between 364 nm (3 iterations at 90% power) and 488 nm (3 iterations at 90% power) in selected regions, using built-in software intended for photobleaching experiments. The laser scanning microscope software was LSM 510 META version 3.2 SP2 (2003), and the MultiTime Series macro version 28-32 was used to control all calcium imaging steps and photoswitching loops in a custom-made recipe.

HEK cells were transfected with iGluR6(L439C) about 48 hours prior to experiments. No YFP cDNA was added in this case, to avoid the overlap with Fluo-4 emission and to maintain a dark background. Expressing cells were determined by brief responses to 300 μM glutamate, which allowed selection of the regions to be photoswitched. Neurons expressing iGluR6(L439C) were identified by co-transfection with DsRed at 3:1 ratio.

No photobleaching was observed at the wavelengths and intensities used in the experiments, which lasted less than 30 min. A significant reduction in calcium responses was evident ~1 hour after loading the cells with Fluo-4, probably due to bleaching and/or washout of Fluo-4, which is to be expected with this non-ratiometric calcium dye. Although the spatial resolution of photoswitching was not studied in detail in these experiments, it is mostly dependent on the focusing of the 364 nm and 488 nm light and should be only limited by diffraction.

Calculation of calcium traces and time series image processing was carried out with the microscope built-in software (physiology package) or with the ImageJ software version 1.33u (http://rsb.info.nih.gov/ij) with plugins LSM-Reader 3.2f and Z-profiler.

Whole-Cell Patch Clamping

Patch clamp recordings were carried out using an Axopatch 200A amplifier in the whole cell mode. HEK cells were voltage clamped at −60 mV and hippocampal neurons were current clamped at about −65 mV. Pipettes had resistances of 2-5 MΩ and were filled with a solution containing, for HEK cells (in mM):145 CsCl, 5 EGTA, 0.5 $CaCl_2$, 1.0 $MgCl_2$ and 10 Hepes, pH7.2, and for neurons (in mM): 135 K-gluconate, 10 NaCl, 10 Hepes, 2 $MgCl_2$, 2 MgATP, 1 EGTA, pH 7.4. The extracellular solution for HEK cells was (in mM): 135 NaCl, 5.4 KCl, 0.9 $MgCl_2$, 1.8 $CaCl_2$ and 10 Hepes, pH 7.6, and for hippocampal neurons: 138 NaCl, 1.5 KCl, 1.2 $MgCl_2$, 2.5 $CaCl_2$, 10 glucose and 5 Hepes, pH 7.4. In order to block iGluR6 desensitization, HEK cells were preincubated in 0.3 mg/ml concanavalin A type VI (Sigma) [26, 27]. Illumination was applied using a TILL Photonics Polychrome monochromator through the side port of the $IX_{70}$ inverted microscope of the physiology rig (Olympus) and using either a 40× or 60× objective. Fast photoswitching experiments were carried out with a custom shuttered laser illumination setup mounted on a large breadboard. Briefly, a 488 nm, 20 mW argon-ion laser (Laser Innovations) and a 374 nm, 8 mW Cube laser (Coherent) were combined with a dichroic mirror z405RDC (Chroma) and coupled into a P600-2-UV/vis optical fiber (Ocean Optics), using a 10×, 0.25 NA, 16.5 mm WD objective (Newport). The fiber was connected into the IX$_{70}$ microscope (Olympus) through the Laser B port using a custom-made adapter. Fast shutters (Uniblitz UHS1T2-100 driven by VMM-T1 controllers, Vincent Associates) were placed at the output of each laser to control the illumination pulses via software trigger.

Electrophysiological data was recorded with pClamp software, which was also used to automatically control the monochromator and laser shutters by means of digital signals and sequencing keys.

Power Dependence of Photoswitching

Illumination power was reduced using a variable number of plastic slides that acted as neutral density filters. Current steps produced by 380 nm and 500 nm illumination were fitted by a single exponential function and the normalized amplitude ($A_{on}$, $A_{off}$ respectively) and time constant ($\tau_{on}$, $\tau_{off}$ respectively) were obtained for each illumination power. In order to calibrate irradiance (illumination power/area), the illumination power was measured with a Newport optical power meter model 840 at the exit of the microscope objective (Olympus UPlanApo 60×/1.2 W). The illuminated area was calculated from the image of a calibrated grid (Zeiss).

Results

The chemical photo-switch MAG (consisting of: Maleimide for attachment to an introduced cysteine, the photo-isomerizable Azobenzene moiety, and Glutamate as an agonist) was covalently attached to an introduced cysteine at residue 439 on the outer surface of the ligand-binding domain of the kainate receptor, iGluR6. As shown in Example 2, in the dark and under visible illumination (~500 nm), MAG is mainly in its trans form, with little or no activation of the receptor. Irradiation at long wave UV (~380 nm) induces cis photo-isomerization and positions the glutamate in the binding pocket, thus activating the receptor. Photoswitching of MAG leads to the opening and closing of the cation-selective pore of iGluR6(439C). Our goal here was to to determine the properties of optical excitation of neurons expressing LiGlUR.

Spatial Control

One of the attractions of light-gated channels is that, in principle, it should be possible to selectively activate only those cells that express them and fall within an illumination volume. Because iGluR6 can be rendered highly calcium permeant with a single mutation [12], the ability of light to activate calcium fluxes could be tested in single cells by imaging intracellular calcium with a fluorescent indicator. Using a laser scanning confocal microscope equipped with 364 nm (UV) and 488 nm (visible) lasers, spatially delimited photo-responses in select cells were obtained. Perfusion of 300 μM glutamate elicited calcium responses in all LiGluR expressing HEK293 cells. Single cells from among these were selected and irradiated them individually at 364 nm and 488 nm. Optical stimulation triggered rises in calcium only in the illuminated cell. Similarly, light was used to stimulate hippocampal neurons expressing LiGluR with spatial selectivity. Calcium responses to photo-stimulation was observed in single neurons that were doubly transfected with DsRed and iGluR6(439C) when the illumination was pointed at them. These results indicate that LiGluR can take full advantage of spatially delimited photo-stimulation [13], where excitation is confined to the illuminated volume because the photo-responsive element is covalently attached to the channel. These experiments provide a simple all-optical means of delineating neural circuits in culture or native tissue, using the LiGluR photo-switch as a remote actuator, standard fluorescent probes as sensors, and commercially available laser scanning microscopes. More sophisticated hardware platforms have also been developed recently [14] that should help improve temporal and spatial resolution and data processing.

Reproducible Bouts of Light-Evoked Firing in LiGluR Expressing Neurons

While calcium imaging could be used to detect the excitation of LiGluR-expressing cells, patch clamping was used to characterize the excitation quantitatively. The ability of light to excite cultured postnatal hippocampal neurons, which were transfected with iGluR6(L439C) and FP and labeled with MAG, was examined. Current-clamp recordings were performed on the FP-positive neurons (FIG. 23a).

Figure 23:
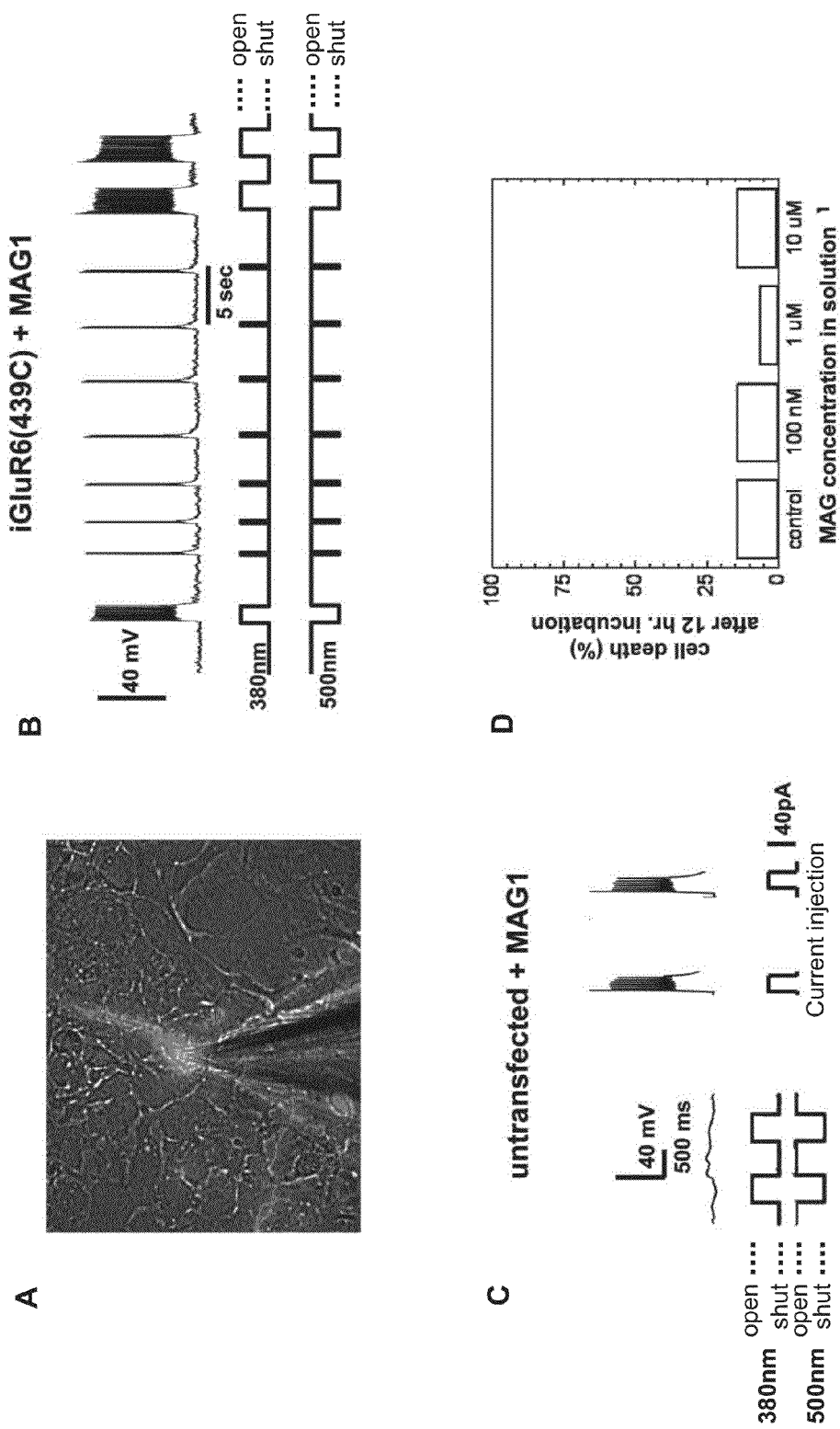
FIGS. 23A-D depict trains of action potential firing following photostimulation.

Switching from 500 nm illumination, which deactivates the receptor, to 380 nm to activate the receptor evoked large depolarizations and trains of action potentials for periods defined by the duration at the shorter wavelength (FIG. 23b). The amplitude of depolarization and the frequency of action potential firing were reproducible (FIG. 23b). The trains of light-evoked action potentials were similar to trains evoked by current injection. Light depolarized only the transfected neurons. Neurons in the same petrie dish that were not transfected did not respond (FIG. 23c), despite the fact that they had been exposed to MAG during the labeling period. This lack of effect can be attributed to the absence of a native cysteine in native GluRs at a location that would permit MAG to attach and be in the correct geometry for its glutamate end to reach the binding pocket in either isomer of the azobenzene.

Photostimulation of the LiGluR-expressing neurons could be maintained for more than an hour in calcium imaging and for as long as seals held in patch clamp (up to 45 minutes) without any indication of toxicity due to illumination or MAG exposure. Cultured hippocampal neurons were often patch-clamped two or more hours after MAG conjugation, indicating that MAG is not toxic over a short period of time. Neuronal survival following 12 hours of continuous exposure to several concentrations of MAG was also examined. This is much longer than the standard 15 minute labeling time that was employed for the recordings. Staining for dead cells using a Live-Dead viability/cytotoxicity assay (Molecular Probes, kit L-7013) no difference was found in cell death between neurons exposed to MAG and controls that were cultured in parallel (FIG. 23d). These observations indicate that MAG has no detectable toxicity at the concentrations in which it is employed. This is consistent with our earlier observation that a model of MAG, which contains the (2S,4R)-4-substituted glutamate and a linker resembling half of the azobenzene tether, has an apparent affinity of 180 μM [Example 2]. Thus, the typical labeling concentration of 10 μM MAG will activate iGluR6 only minimally. Activation of other iGluRs will be minimal because similarly substituted glutamate analogues have been shown to be selective kainate receptor agonists.

FIGS. 23A-D. Photostimulation Yields Reproducible Trains of Action Potential Firing.

(a) Hippocampal neurons transfected with LiGluR are easily identified for patching by GFP fluorescence. (b) A neuron transfected with iGluR6(439C) and labeled with MAG is illuminated at 380 nm for hundreds of milliseconds to seconds, yielding reproducible depolarizations that trigger trains of action potentials which fire at a frequency that is characteristic of the particular cell. Illumination at 500 nm turns the response off and permits repolarization. The firing pattern can be sculpted by varying the duration of illumination at the two wavelengths. Illumination was with a monochromator. (c)

Untransfected neuron has no response to light, despite exposure to MAG, but does fire repetitively in response to current injection. (d) MAG has no deleterious effect on neurons. Untransfected neurons incubated for 12 hours in MAG (as opposed to the standard labeling time of 15 min) showed no increase in cell death compared to control.

Photoswitching in Milliseconds Generates Action Potentials and Mock EPSPs

EPSPs mediated by native iGluRs are triggered by very brief (millisecond long) and synchronous glutamate binding events at groups of receptors in postsynaptic membranes. Ideally, an engineered system for triggering neuron activity would operate on the same timescale. Because the rate of activation and deactivation of LiGluR depends linearly on illumination intensity (FIG. 24b), it was determined that millisecond switching was possible under an illumination intensity of approximately 1 mW/mm$^2$. This intensity is typical of focused light from a standard fluorescence lamp or monochromator system through standard objectives, as well as for small diode lasers. Indeed, brief (1-5 ms) pulses of light at ~1 mW/mm$^2$ evoked currents that triggered reproducible patterns of action potentials (FIG. 25a). Light-evoked patterns of firing were repeatable within a neuron and in different neurons. Furthermore, the amplitude of the responses could be easily attenuated with neutral density filters, in order to mimic EPSPs (FIG. 25b, lower trace).

Rather than continuously illuminating the cells while switching back and forth between two wavelengths, we also evoked patterned action potential firing using only a brief pair of light pulses while otherwise keeping the cell in the dark (FIG. 25c). This allowed a significant reduction in light exposure (although, even under continuous illumination, no photo-toxic effects were observed during any LiGluR experiments).

Figure 24:
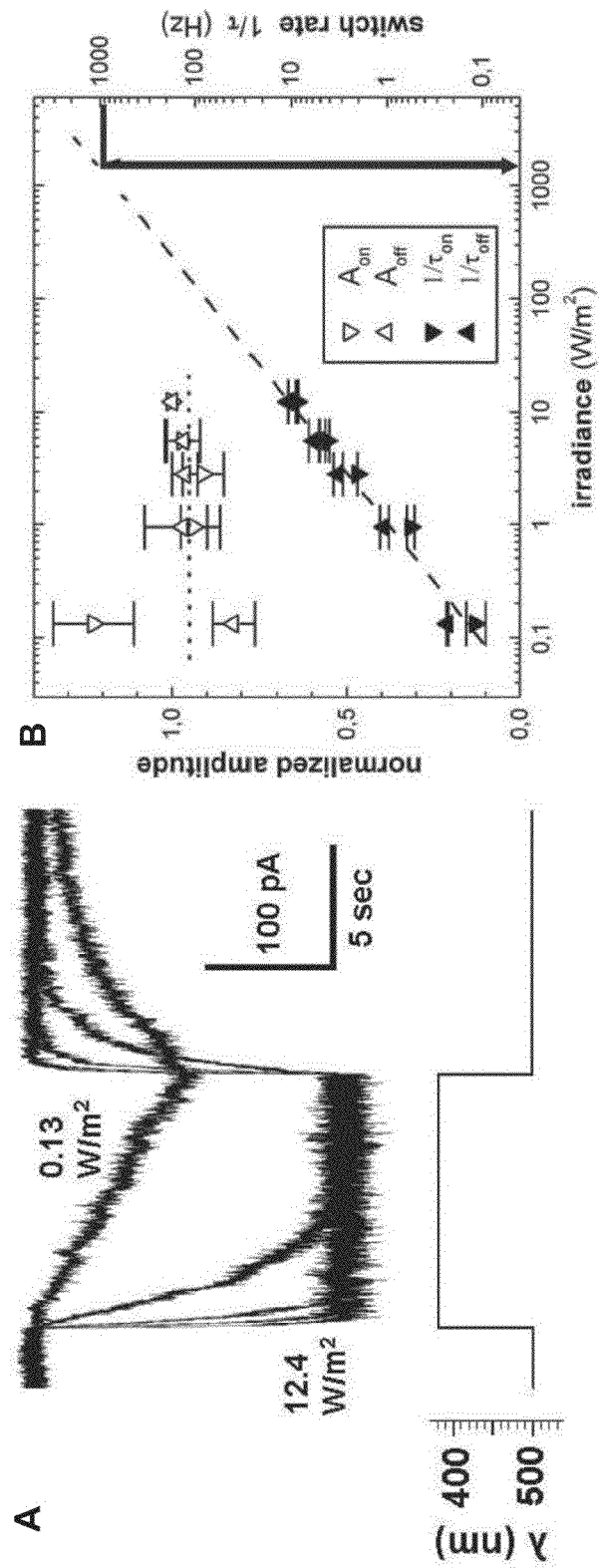
FIGS. 24A and 24B depict dependence of speed of gating on illumination intensity.
Figure 25:
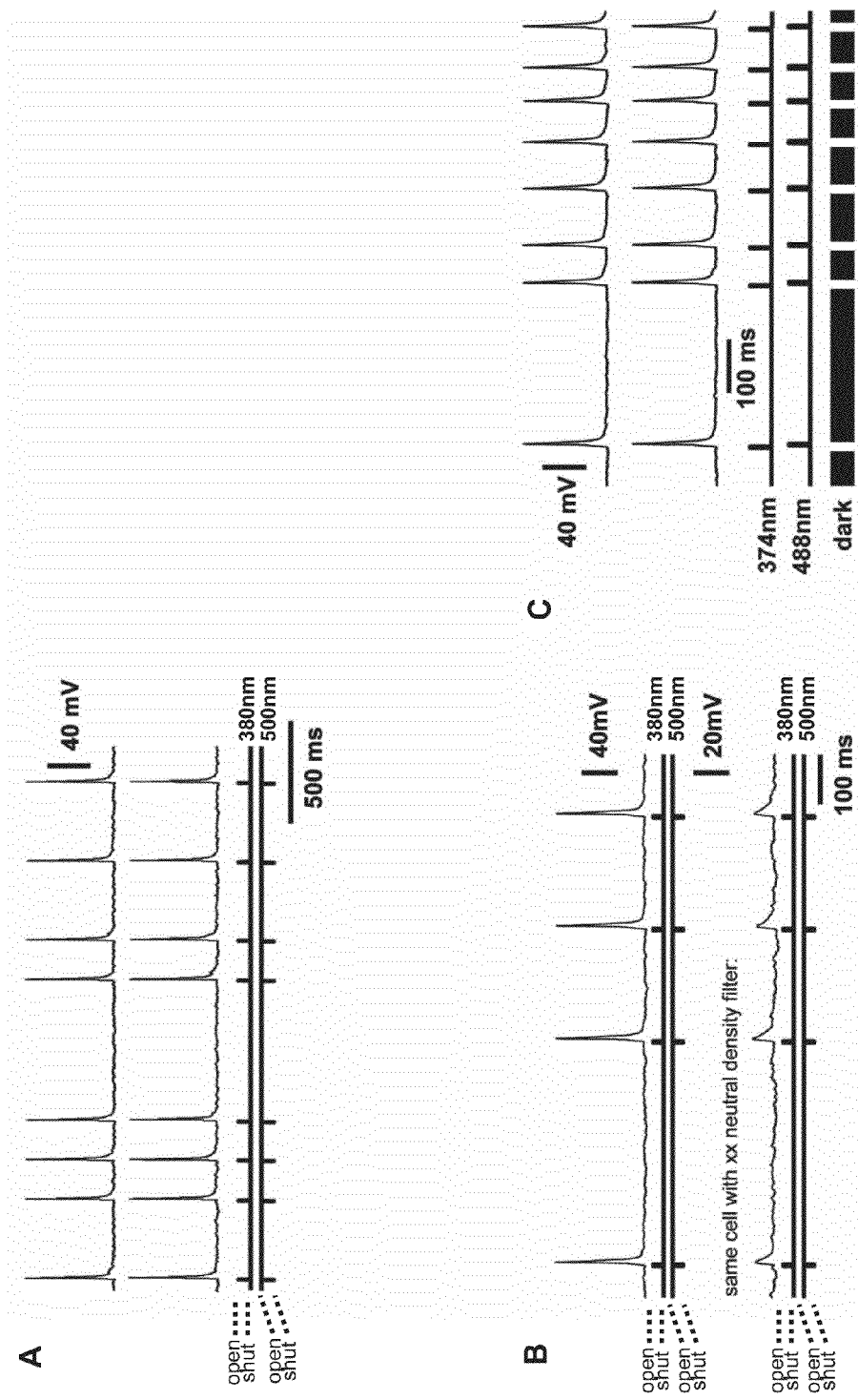
FIGS. 25A-C depict designed temporal firing patterns.

FIGS. 24A and 24B: Speed of Gating Depends on Intensity.

(a) Speed of activation and deactivation of iGluR6 current in HEK cells under voltage clamp increases with light intensity. (b) Rates of on and off photoresponses in (a), measured from single exponential fits, are plotted against intensity, and yield a linear relation, which can be extrapolated to 1 KHz at ~1 KW/m$^2$. This leads to the prediction that a 1 mm region illuminated by a 1 mW laser should evoke significant currents in ~1 ms, which is of the timescale characteristic for synaptic activation of iGluRs. Illumination was with a monochromator.

FIGS. 25A-C. Designed Temporal Firing Patterns.

1-5 ms pulses of illumination are sufficient to significantly depolarize neurons and to trigger single action potentials (APs). Scale bars=40 mV and 100 ms. (a) A train of 1 ms pulses of 374 nm light (laser) reliably triggers the same temporal pattern of action potential firing in a neuron. Reproducible firing is triggered in two different neurons by the same pattern of 374 nm light pulses. (b) In the same cell, a train of 374 nm light pulses produces action potentials (top trace) or, when the illumination intensity is attenuated, sub-threshold EPSP-like responses (bottom trace). (c) LiGluR can be activated with a 2 ms pulse at 374 nm and deactivated with a 2-5 ms pulse at 488 nm to fire the neuron, and the interval between action potentials can be in the dark to minimize irradiation.

Because rapid stimulation of neurons is often employed in studies of synaptic plasticity, we were interested in determining the response of neurons to light pulses delivered at high frequencies. We found that APs followed our optical stimulation reliably up to 30 Hz (FIG. 26), higher than the frequency reported for ChR2 [Boyden et al., 2005]. We attribute this performance to the fact that LiGluR evokes larger currents, does not desensitize, and is capable of faster deactivation under optical drive (see Supplemental Material and Supplemental FIG. 1). In LiGluR, the loss of 1:1 firing at high frequencies appears to be a function of the firing properties of the neurons, not the kinetics of light-gating, since sub-threshold depolarizations were reliably evoked at all frequencies tested (up to 100 Hz, data not shown).

Figure 26:
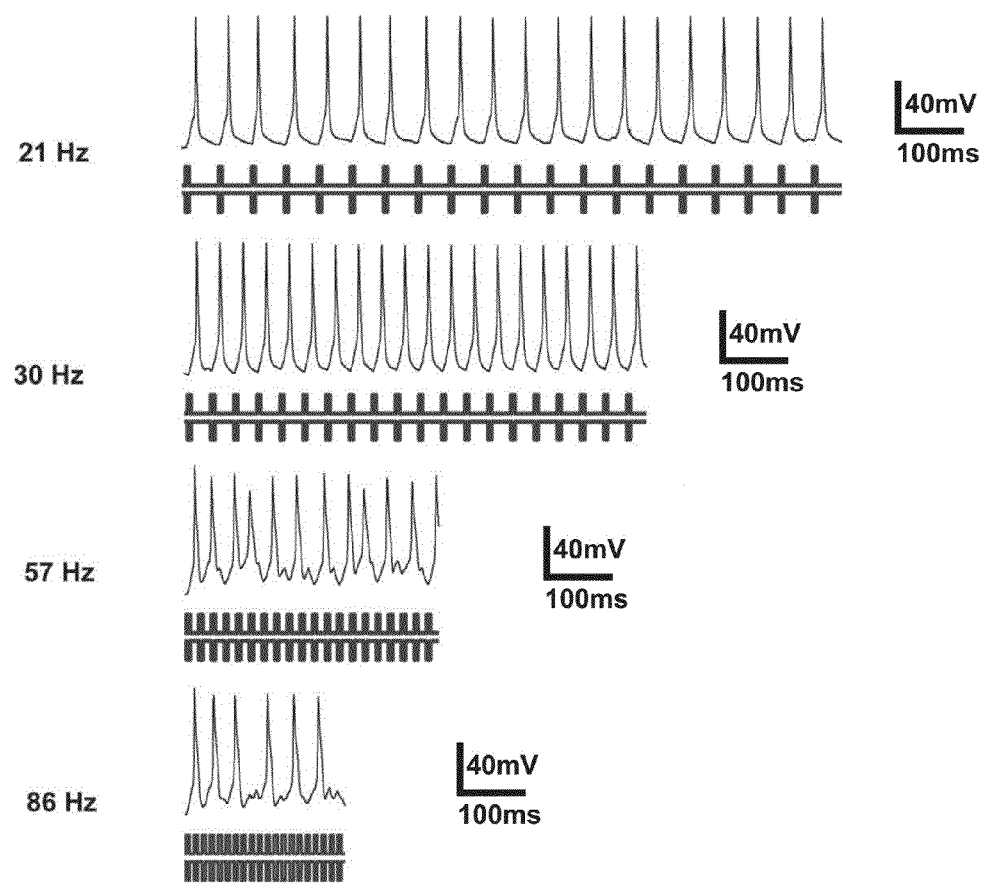
FIG. 26 depicts photo-stimulation of LiGluR up to at various frequencies.

FIG. 26. Neurons can Follow Photo-Stimulation of LiGluR Up to 30 Hz.

Trains of 5 ms laser pulses at 374 nm can reliably trigger action potentials up to a rate of 30 Hz. At 57 Hz only 12 action potentials are evoked by 20 stimuli, while at 86 Hz only 6 action potentials are evoked by 20 stimuli.

Figure 27:
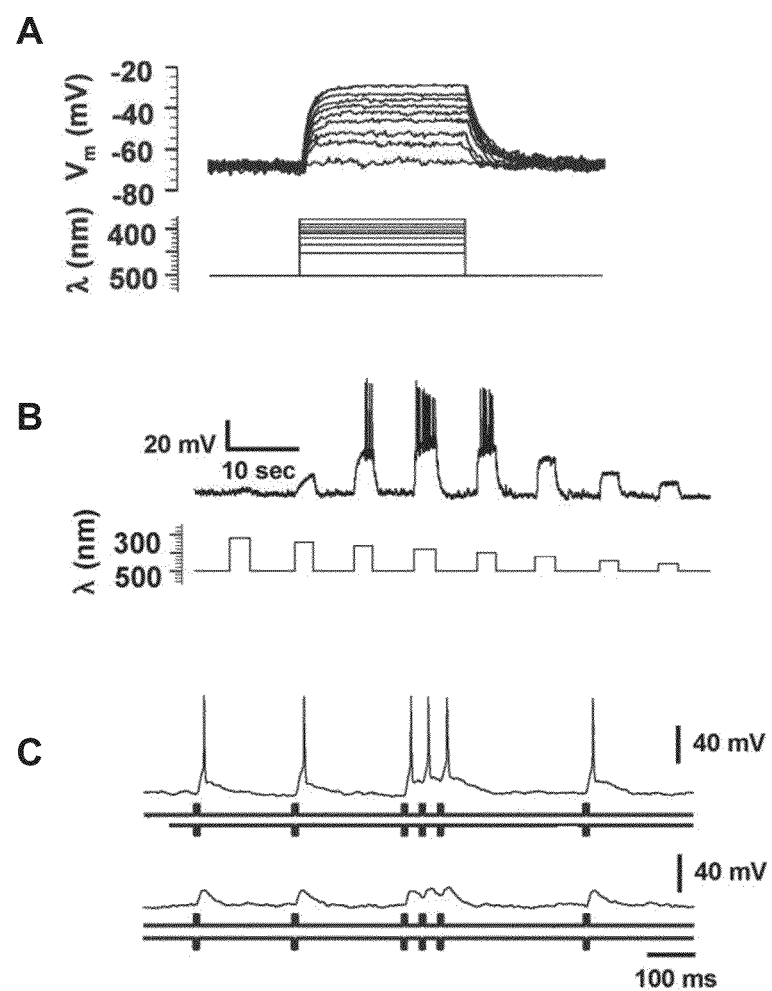
FIGS. 27A-C depict wavelength-dependent depolarization.

Light Evokes Depolarization and Action Potential Firing in a Wavelength Dependent Manner To characterize the amplitude of depolarization evoked by steady illumination at different wavelengths iGluR6(439C) in HEK293 cells labeled with MAG was examined under whole-cell current clamp. Channel opening by light evoked large steady-state depolarizations. By taking advantage of the fact that the photo-stationary state of MAG (i.e. the relative proportion of azobenzene in cis and trans) can be precisely varied by illumination wavelength, it was possible to produce steady-state depolarizations whose amplitudes depended on wavelength (FIG. 27a). Similar graded depolarizations could be evoked in cultured postnatal hippocampal neurons that were transfected with iGluR6(439C) and exposed to MAG. As seen in the HEK cells, the amplitude of depolarization depended on wavelength, with a maximum at ~380 nm. The largest depolarizations evoked a train of action potentials (FIG. 27b). The wavelength dependence was used to adjust the size of EPSP-like waveforms that were triggered by brief pulses of light, so that, for example, pulses of light at 380 nm generated super-threshold depolarizations and evoked action potentials, while EPSP-like responses were induced in the same cell by pulses of light of the same duration, but at 430 nm (FIG. 27c). Thus, the amplitude of brief excitatory events evoked by pulses of light can be controlled either by modifying the intensity of illumination at 380 nm, or by adjusting wavelength.

FIGS. 27A-C. Wavelength-Dependent Depolarization.

(a) In current-clamped

HEK cells expressing LiGluR, light induces depolarizations whose amplitude depend on illumination wavelength. In this way, the cell membrane potential can be accurately controlled across a wide range. (b) Illumination at a range of wavelengths depolarizes neurons. Some depolarizations are large enough to reach threshold and trigger action potentials. (c) Patterned illumination with 380 nm light evokes action potentials while 430 nm light induces sub-threshold, EPSP-like responses in the same cell. Illumination was with a monochromator.

Protracted Excitation in the Dark

We find that our azobenzene photoswitch is very robust, yielding reproducible responses for many minutes in HEK293 cells under prolonged illumination [Volgraf et al., 2006]. Hippocampal neurons also tolerated tens of minutes of continuous illumination, alternating between 380 nm and 500 nm at intensities of 1 mW/mm$^2$ or more. These recordings typically ended only upon loss of the seal, and recordings were equally stable with and without illumination. However, behavioral experiments may require activity to be manipulated over a much longer time scale, where photo-destruction of MAG or photo-toxicity to cells could become a concern. To reduce this problem we explored the property of bi-stability of azobenzene in attempt to generate sustained trains of firing in the dark.

Figure 28:
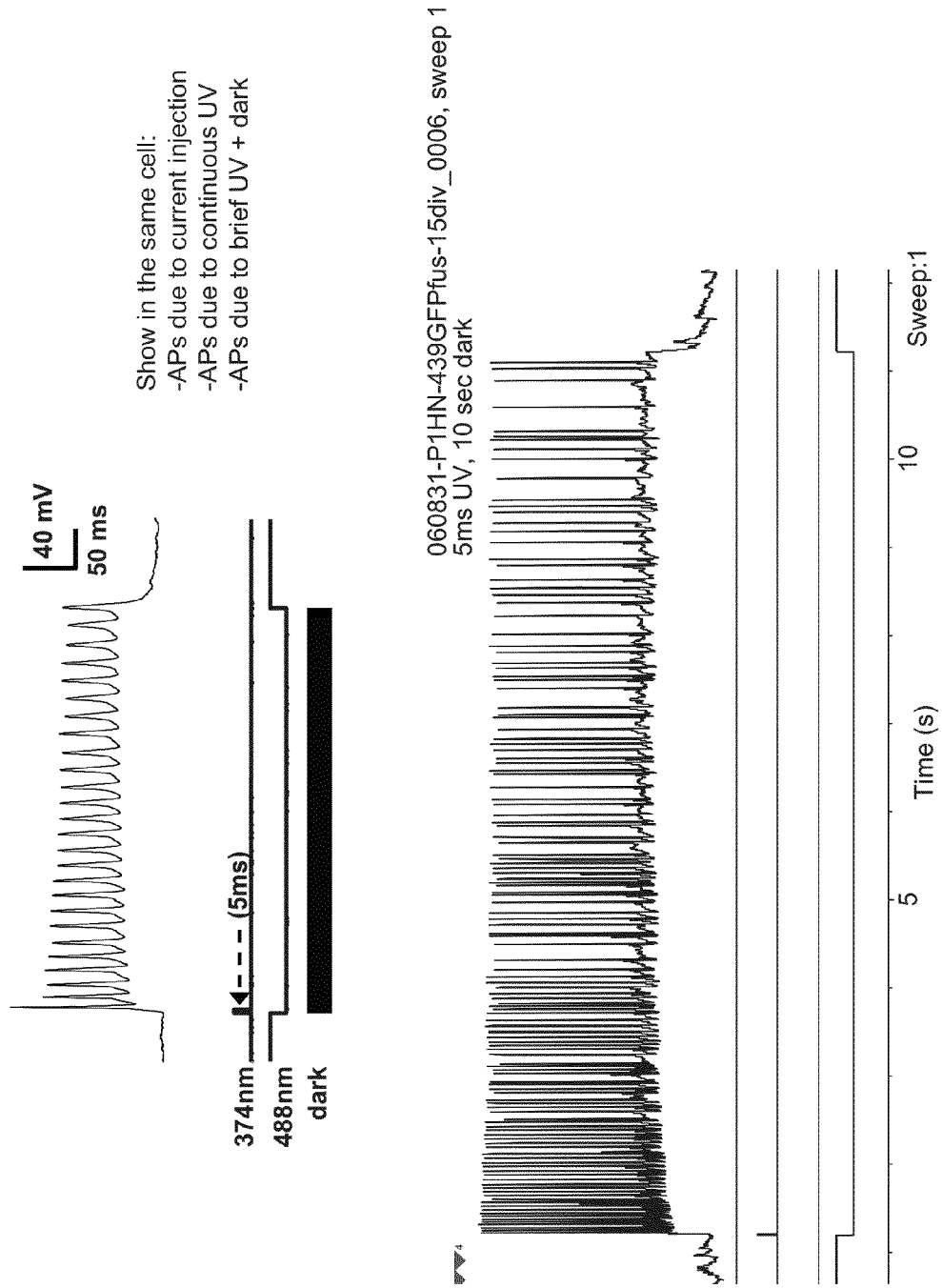
FIG. 28 depicts sustained firing at intrinsic frequency of the cell using brief pulses of illumination followed by dark.

Depending on how azobenzene is derivatized, its higher energy cis conformation is stable for seconds to minutes in the dark [Pozhidaeva et al., 2004]. For MAG, the half-life is 17.65±0.03 minutes [Gorostiza et al., in preparation]. Thus, depolarization induced by a brief pulse of 374 nm light is followed by sustained excitation in an ensuing period during which there is no illumination (FIG. 28, top). This sustained excitation in the dark can then be rapidly extinguished by a brief pulse of 488 nm light (FIG. 28, bottom). This molecular memory of MAG makes it possible to trigger extended periods of excitation with minimal irradiation, during which time the cell fires at its characteristic frequency. This is an advantageous property of LiGluR compared to ChR2.

FIG. 28. Brief Pulses of Illumination Followed by Dark Evoke Sustained Firing at Intrinsic Frequency of the Cell.

Due to the stability of the cis state of MAG, LiGluR activation by a short pulse of 374 nm light yields a long-lasting depolarization that can trigger sustained trains of action potentials in the dark, which can be then turned off with a short pulse of light at 488 nm. (top) Sustained excitation of hippocampal neurons occurs under continuous 374 nm light (top trace) or when a brief pulse of 374 nm light is followed by darkness (bottom trace). (bottom) After a 5 ms pulse of 374 nm light, excitation is sustained for 10 seconds in the dark before being turned off by 488 nm light.

REFERENCES

1. Eder M, Zieglgansberger W, Dodt H U. (2004) Shining light on neurons—elucidation of neuronal functions by photostimulation. Rev Neurosci 15, 167-83.
2. Svoboda K, and Yasuda R. (2006). Principles of Two-Photon Excitation Microscopy and Its Applications to Neuroscience. Neuron, June 15; 50(6):823-39.
3. Callaway E M. (2005). A molecular and genetic arsenal for systems neuroscience. Trends Neurosci 28, 196-201.
4. Lima S Q, Miesenbock G. (2005). Remote control of behavior through genetically targeted photostimulation of neurons. Cell 121, 141-152.
5. Nagel G, Ollig D, Fuhrmann M, Kateriya S, Musti A M, Bamberg E, Hegemann P. (2003). Channelrhodopsin-2, a directly light-gated cation-selective membrane channel. Proc Natl Acad Sci USA 100, 13940-5.
6. Boyden E S, Zhang F, Bamberg E, Nagel G, Deisseroth K. (2005). Millisecond-timescale, genetically targeted optical control of neural activity. Nat Neurosci 8, 1263-8.
7. Nagel G, Brauner M, Liewald J F, Adeishvili N, Bamberg E, Gottschalk A. (2005). Light activation of Channelrhodopsin-2 in excitable cells of *Caenorhabditis elegans* triggers rapid behavioral responses. Curr Biol 15, 2279-84.
8. Schroll C, Riemensperger T, Bucher D, Ehmer J, Voller T, Erbguth K, Gerber B, Hendel T, Nagel G, Buchner E, Fiala A. (2006). Light-induced activation of distinct modulatory neurons triggers appetitive or aversive learning in *Drosophila* larvae. Current Biology 16, 1741-1747.
9. Li X, Gutierrez D, Hanson M, Han J, Mark M, Chiel H, Hegemann P, Landmesser L, Herlitze S. (2005). Fast non-invasive activation and inhibition of neural and network activity by vertebrate rhodopsin and green algae channelrhodopsin. Proc Natl Acad Sci USA 102(49), 17816-21.
10. Bi A, Cui J, Ma Y P, Olshevskaya E, Pu M, Dizhoor A M, Pan Z H. (2006). Ectopic expression of a microbial-type rhodopsin restores visual responses in mice with photoreceptor degeneration. Neuron 50, 23-33.
11. Lester H A, Krouse M E, Nass M M, Wassermann N H, Erlanger B F. (1980). A covalently bound photoisomerizable agonist: comparison with reversibly bound agonists at Electrophorus electroplaques. J Gen Physiol 75, 207-32.
12. Chabala L D, Gurney A M, Lester H A. (1986). Dose-response of acetylcholine receptor channels opened by a flash-activated agonist in voltage-clamped rat myoballs. J Physiol 371, 407-33.
13. Banghart M, Borges K, Isacoff E, Trauner D, Kramer R H. (2004). Light-activated ion channels for remote control of neuronal firing. Nat Neurosci 7, 1381-1386.
14. Volgraf M, Gorostiza P, Numano R, Kramer R H, Isacoff E Y, Trauner D. (2006). Allosteric control of an ionotropic glutamate receptor with an optical switch. Nat Chem Biol 2, 47-52.
15. Kohler M, Burnashev N, Sakmann B, Seeburg P H. (1993). Determinants of $Ca^{2+}$ permeability in both TM1 and TM2 of high-affinity kainate receptor channels: diversity by RNA editing. Neuron 10, 491-500.
16. Lippincott-Schwartz J, Altan-Bonnet N, Patterson G H. (2003). Photobleaching and photoactivation: following protein dynamics in living cells. Nat Cell Biol, Suppl S7-14.
17. Shoham S, O'Connor D H, Sarkisov D V, Wang S S H. (2005). Rapid neurotransmitter uncaging in spatially defined patterns. Nat Methods 2, 837-843.
18. Pedregal C, Collado I, Escribano A, Ezquerra J, Dominguez C, Mateo A I, Rubio A, Baker S R, Goldsworthy J, Kamboj R K, Ballyk B A, Hoo K, Bleakman D. (2000). 4-alkyl- and 4-cinnamylglutamic acid analogues are potent GluR5 kainate receptor agonists. J Med Chem 43, 1958-1968.

Example 6

Conferring Light Sensitivity to a Retina

Methods
Imaging Protocols
Flatmounts

Rats were sacrificed and the eyes were removed intact and placed in paraformaldehyde. After 1-2 hours the eyes were cut open, and the retina was gently separated from the pigment epithelium. Small cuts were made around the perimeter of the retina so that it can be flattened onto a microscope slide. Images were taken with a large-field microscope (such as a Zeiss Lumar Epifluorescence stereo microscope). The tissue was illuminated with 488 nm light, which excites GFP. This lets one see the distribution of our GFP-tagged channels throughout the entire retina.

Cryosections

Rats were sacrificed and the eyes are removed intact and placed in paraformaldehyde. After 1-2 hours the eyes were transferred to a saturated sucrose solution in order to dehydrate overnight. The next morning, eyes were imbedded in a mounting agent and rapidly frozen with dry ice. They were then sectioned in 10-20 µm slices using a standard cryostat. The sections were mounted on microscope slides and imaged on a confocal microscope (such as the Zeiss 510 Meta UV/Vis confocal laser scanning microscope). The tissue was illuminated with 488 nm light, which excites GFP. This lets one see the distribution of our GFP-tagged channels within individual cells.

Retcam

The Retcam is a digital fiber-optic camera developed for imaging retinae in vivo. Rats were anesthetized and laid flat on a lab bench. Their eyes were dilated and then covered with a viscous gel, which acts as an interface between the camera lens and the eye. The retina was imaged with white light or with 488 nm light, which allows for the viewing of GFP. This technique was used to monitor the expression of our GFP-tagged channel without sacrificing the rat.

Physiology

Rats were sacrificed and the eyes were removed intact and placed in a NaCl-based saline solution. Eyes were then cut open in a gelatin-bottomed petri dish, while being continually perfused with oxygenated saline. The retina was gently separated from the pigment epithelium and cut into quadrants. These pieces were then incubated in a papain solution for 10-20 min at 37° C., transferred to an ovomucoid solution (containing bovine serum albumin and trypsin inhibitor) for 5 min, and a DNase solution for 10 min. The retina pieces were then rinsed and placed in a holding chamber containing oxygenated Ames medium until used.

Prior to recording, each piece of retina was incubated in 100-300 µM AAQ (acrylamide-azobenzene-quaternary ammonium ion) for 30 min, removed, rinsed, then mounted flat in a recording chamber. Retinae were continually perfused with oxygenated saline during recordings, except when neurotransmitter blockers are used.

Recordings were done on an Olympus upright microscope. For data acquisition, signals were amplified with an Axon Instruments amplifier and sent through an analog-to-digital converter to a computer running ClampEx (Axon Instruments). Signals were filtered at 2-5 kHz and sampled at 50 kHz. Illumination at 380 nm and 500 nm is provided by a monochrometer (Polychrome V, Till Photonics).

Micropipettes of borosilicate glass were pulled on a two-stage vertical puller to obtain a resistance of 3-6 MΩ. These were filled with the same saline as used in the bath. Loose-seal recordings are made by applying firm suction to the membrane of an identifiable retinal ganglion cell. During recording, all lights except that from the monochrometer were turned off and the filter wheel was set to a 100% mirror to deflect the light completely to the tissue. Recordings typically lasted 10-30 min.

ERGs

Rats were dark-adapted overnight, and the entire procedure was done under very dim red light. Rats were anesthetized and placed in a standard electroretinogram (ERG) setup. Recording electrodes were embedded in contact-like cups, which were mounted onto each eye with a conductive adherent fluid. Reference electrodes were placed in the mouth. A light source emitted brief flashes of white light at various intensities. The electrical response of the retina to each light flash was recorded; three trials per intensity were averaged together. Under normal conditions, the ERG will consist of a small downward deflection (A-wave), which reflects the activity of photoreceptors, and a larger upward deflection (B-wave), which reflects the activity of bipolar cells.

Results

Figure 29A:
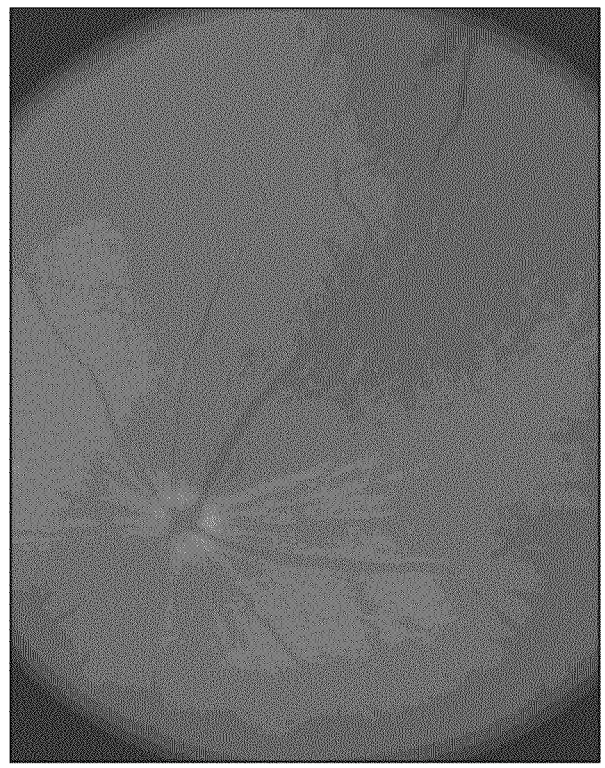
FIGS. 29A and 29B depict retcam images of rat eyes injected with a recombinant adeno-associated virus (rAAV) vector comprising a nucleotide sequence encoding a potassium channel-green fluorescent protein (SPARK-GFP) fusion protein under the control of a synapsin promoter (AAV-SYN-SPARK-GFP).
Figure 29B:
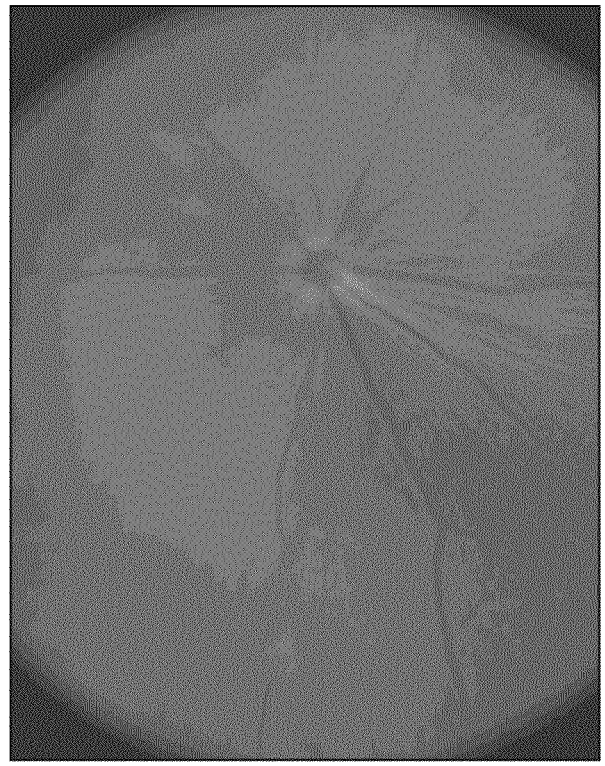
Figure 30:
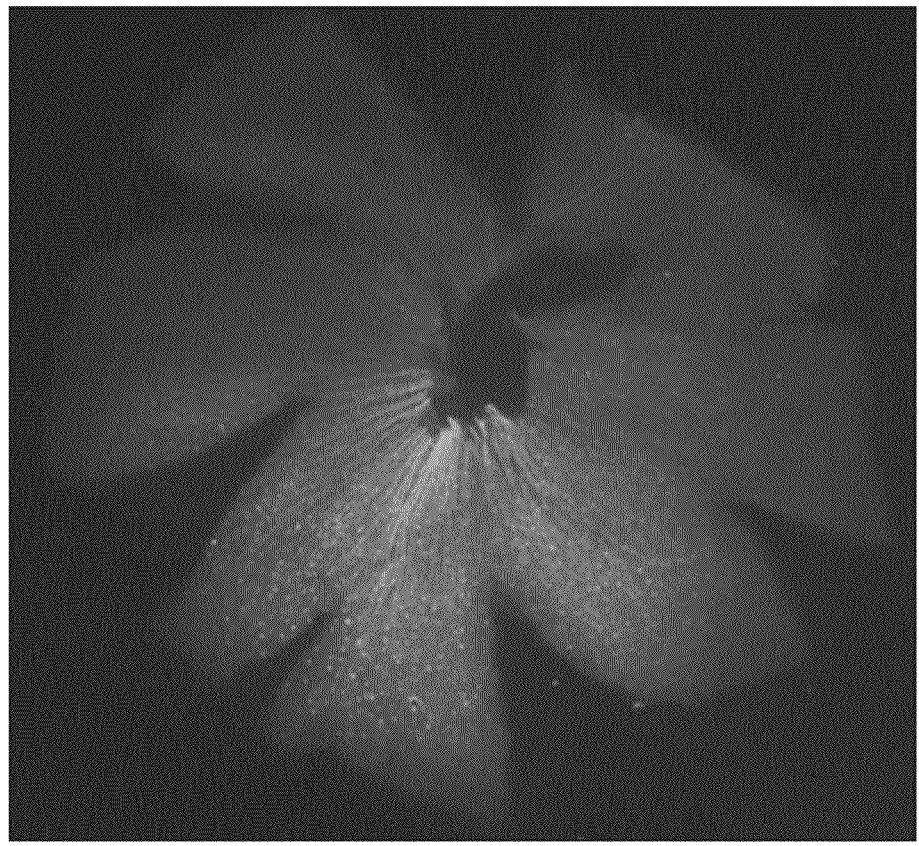
FIG. 30 depicts a flatmount of a rat eye injected with AAV-SYN-SPARK-GFP.
Figure 31:
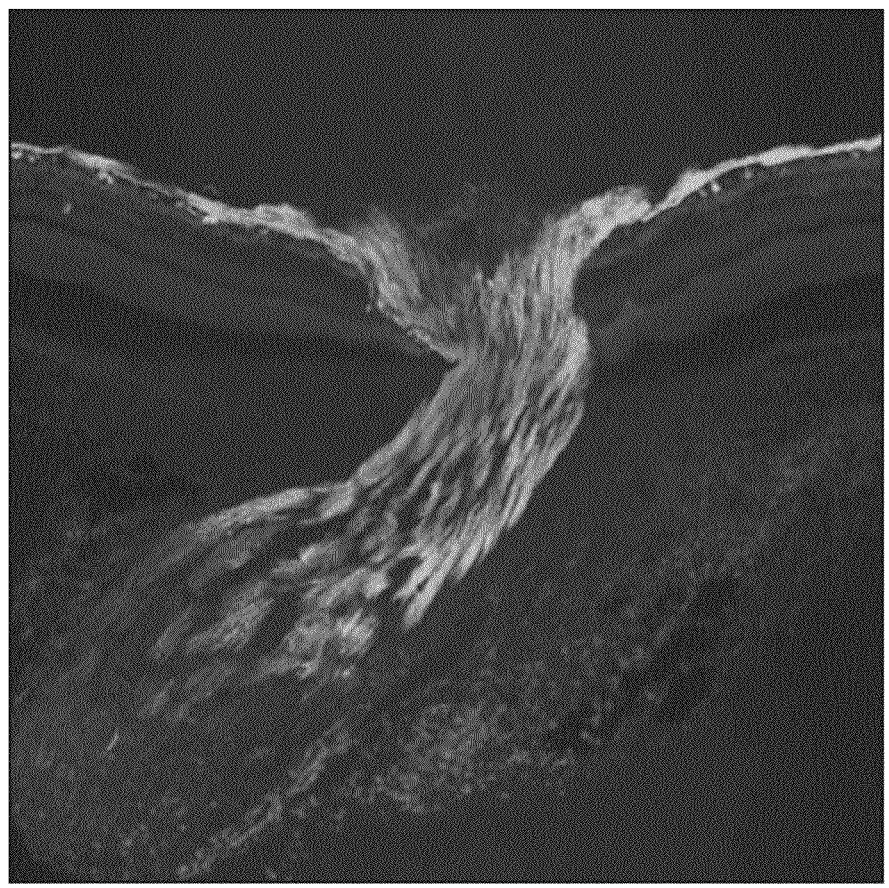
FIG. 31 depicts in vivo expression of SPARK.
Figure 32:
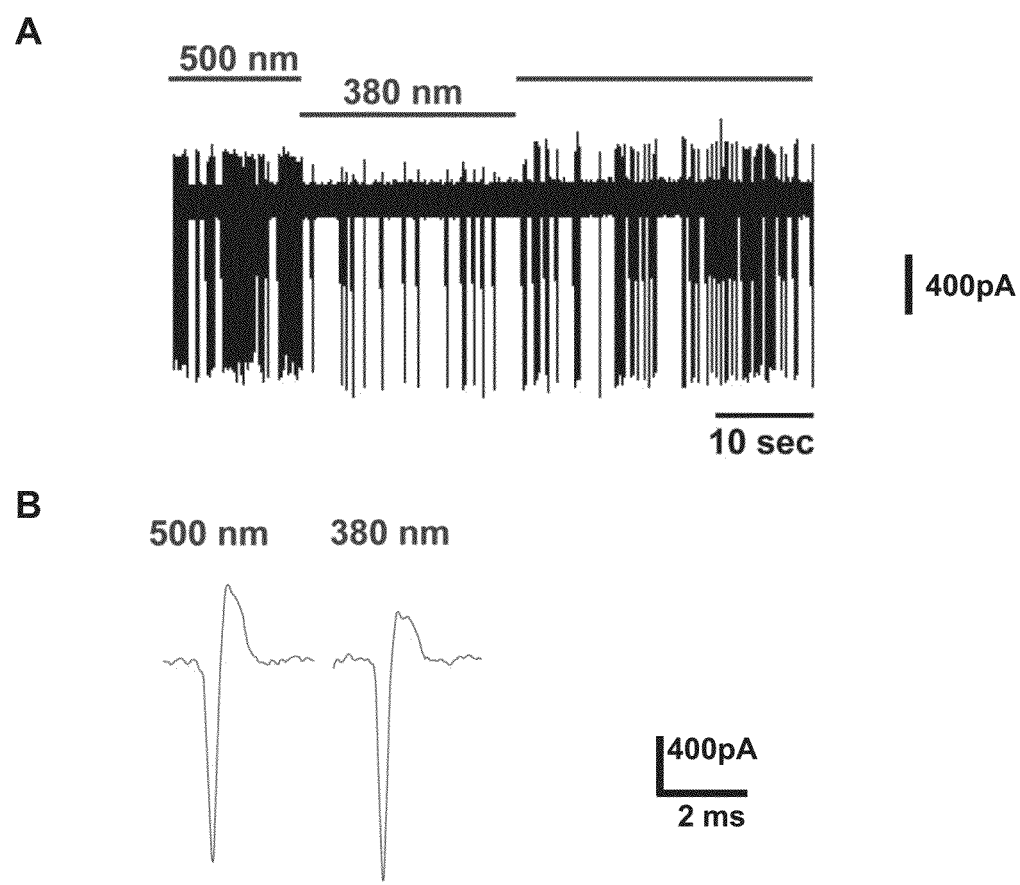
FIGS. 32A and 32B depict inhibition by light of spontaneous firing of SPARK-expressing retinal ganglion cells in intact retina.
Figure 33:
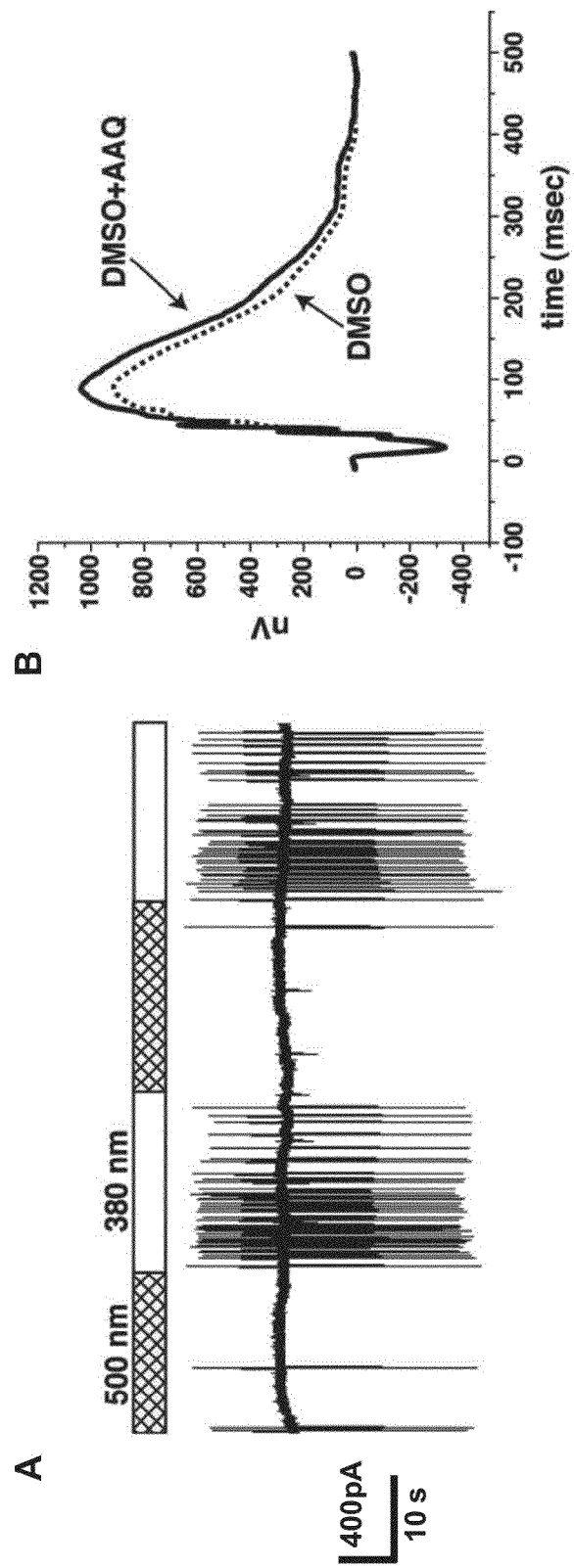
FIGS. 33A and 33B depict light sensitivity imparted on rat retina by PAL.

The data are presented in FIGS. 29-33. FIG. 29 depicts a retcam image of an eye injected with a recombinant adeno-associated virus (rAAV) vector comprising a nucleotide sequence encoding a SPARK-GFP fusion protein under the control of a synapsin promoter (AAV-SYN-SPARK-GFP). FIG. 30 depicts a flatmount of an eye injected with AAV-SYN-SPARK-GFP. FIG. 31 depicts in vivo SPARK expression. FIG. 32 depicts data showing that light inhibits spontaneous firing of SPARK-expressing retinal ganglion cells in intact retina. Thus, the SPARK channel turns neurons into virtual "off" cells.

FIG. 33A depicts extracellular recording from a PAL-treated retinal ganglion cell showing optical control of firing. FIG. 33B depicts ERG recordings from control (DMSO alone) and PAL-treated (DMSO+AAQ) rat eyes, 7 days post injection. Thus, PAL imparts light sensitivity on rat retina without toxic consequences.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An in vitro method of identifying an agent that modulates an activity of a non-light-regulated polypeptide, the method comprising:
   a) contacting a cell with a test agent which is a candidate agent for modulating the activity of the non-light-regulated polypeptide which is a calcium channel or a sodium channel, wherein the cell expresses:
   i) the non-light-regulated polypeptide; and
   ii) a light-regulated polypeptide that regulates the activity of the non-light-regulated polypeptide, wherein the light-regulated polypeptide comprises a photoreactive synthetic regulator of protein function, wherein the photoreactive synthetic regulator comprises:
   a-i) a linker domain comprising a binding moiety that provides for stable association with covalent linkage to the light-regulated polypeptide, wherein the binding moiety is other than a bromomethyl moiety;
   a-ii) a photoisomerizable group; and
   a-iii) a ligand that binds to a ligand binding site of the light-regulated polypeptide;
   b) exposing the cell to light of a wavelength such that the ligand binds to a ligand binding site of the light-regulated polypeptide, wherein, in the absence of the test agent, exposure of the cell to light results in activation of the non-light-regulated polypeptide by the light-regulated polypeptide; and
   c) determining the effect, if any, of the test agent on the activity of the non-light-regulated polypeptide wherein a test agent that modulates activity of the non-light-regulated polypeptide following said light exposure is a candidate agent for modulating the activity of the non-light-regulated polypeptide.

2. The method of claim 1, wherein the non-light-regulated polypeptide is a sodium channel.

3. The method of claim 2, wherein the non-light-regulated polypeptide is a calcium channel.

4. The method of claim 1, wherein step (c) comprises detecting a change in the intracellular concentration of an ion.

5. The method of claim 1, wherein step (c) comprises detecting a change in the membrane potential of the cell.

6. The method of claim 1, wherein the cell is a mammalian cell.

7. The method of claim 1, wherein the mammalian cell is a cell line.

8. The method of claim 7, wherein the mammalian cell is selected from a 293 cell, a 3T3 cell, a COS cell, and a PC12 cell.

9. The method of claim 1, wherein the ligand-binding polypeptide is selected from an ion channel, a cation channel, a ligand-gated ion channel, and a voltage-gated ion channel.

10. The method of claim 1, wherein the ligand-binding polypeptide is a sodium channel, is a potassium channel, a chloride channel, a GABA receptor, or a serotonin receptor.

* * * * *